United States Patent
Watanabe et al.

(10) Patent No.: US 10,870,676 B2
(45) Date of Patent: *Dec. 22, 2020

(54) ANTISENSE NUCLEIC ACIDS

(71) Applicants: NIPPON SHINYAKU CO., LTD., Kyoto-shi, Kyoto (JP); NATIONAL CENTER OF NEUROLOGY AND PSYCHIATRY, Kodaira-shi, Tokyo (JP)

(72) Inventors: Naoki Watanabe, Tsukuba (JP); Youhei Satou, Tsukuba (JP); Shin'ichi Takeda, Kodaira (JP); Tetsuya Nagata, Kodaira (JP)

(73) Assignees: NIPPON SHINYAKU CO., LTD., Kyoto (JP); NATIONAL CENTER OF NEUROLOGY AND PSYCHIATRY, Kodaira (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/408,529

(22) Filed: May 10, 2019

(65) Prior Publication Data

US 2020/0115411 A1 Apr. 16, 2020

Related U.S. Application Data

(63) Continuation of application No. 15/619,996, filed on Jun. 12, 2017, now Pat. No. 10,329,319, which is a continuation of application No. 14/615,504, filed on Feb. 6, 2015, now Pat. No. 9,708,361, which is a continuation of application No. 13/819,520, filed as application No. PCT/JP2011/070318 on Aug. 31, 2011, now Pat. No. 9,079,934.

(30) Foreign Application Priority Data

Sep. 1, 2010 (JP) .................................. 2010-196032

(51) Int. Cl.
| | | |
|---|---|---|
| C07H 21/04 | (2006.01) | |
| C12N 15/11 | (2006.01) | |
| C12N 15/113 | (2010.01) | |
| C07H 21/00 | (2006.01) | |
| C12Q 1/68 | (2018.01) | |

(52) U.S. Cl.
CPC ............ *C07H 21/04* (2013.01); *C07H 21/00* (2013.01); *C12N 15/111* (2013.01); *C12N 15/113* (2013.01); *C12N 2310/11* (2013.01); *C12N 2310/315* (2013.01); *C12N 2310/3145* (2013.01); *C12N 2310/321* (2013.01); *C12N 2310/3525* (2013.01); *C12N 2320/33* (2013.01)

(58) Field of Classification Search
None
See application file for complete search history.

(56) References Cited

U.S. PATENT DOCUMENTS

| | | |
|---|---|---|
| 6,653,467 B1 | 11/2003 | Matsuo et al. |
| 6,727,355 B2 | 4/2004 | Matsuo et al. |
| 8,084,601 B2 | 12/2011 | Popplewell et al. |
| 8,455,636 B2 | 6/2013 | Wilton et al. |
| 8,871,918 B2 | 10/2014 | Sazani et al. |
| 9,024,007 B2 | 5/2015 | Wilton et al. |
| 9,994,851 B2 | 6/2018 | Wilton et al. |
| 10,227,590 B2 | 3/2019 | Wilton et al. |
| 10,266,827 B2 | 4/2019 | Wilton et al. |
| 2006/0147952 A1 | 7/2006 | van Ommen et al. |
| 2010/0168212 A1 | 7/2010 | Popplewell et al. |
| 2012/0190728 A1 | 7/2012 | Bennett et al. |
| 2013/0072541 A1 | 3/2013 | Garcia |
| 2013/0109091 A1 | 5/2013 | Baker et al. |
| 2019/0127738 A1 | 5/2019 | Sazani et al. |

FOREIGN PATENT DOCUMENTS

| | | |
|---|---|---|
| CA | 2507125 A1 | 6/2004 |
| EP | 1054058 A1 | 11/2000 |
| EP | 1160318 A2 | 12/2001 |
| EP | 1191097 A1 | 3/2002 |
| EP | 1191098 A2 | 3/2002 |
| EP | 1568769 A1 | 8/2005 |
| EP | 2206781 A2 | 7/2010 |
| EP | 2602322 A1 | 6/2013 |
| EP | 2594640 B1 | 12/2015 |
| EP | 2602322 B1 | 3/2016 |
| EP | 3404100 A1 | 11/2018 |
| JP | 2000-325085 A | 11/2000 |
| JP | 2002-10790 A | 1/2002 |
| JP | 2002-325582 A | 11/2002 |
| JP | 6406782 B2 | 10/2018 |
| WO | WO-99/053101 A1 | 10/1999 |
| WO | WO-02/24906 A1 | 3/2002 |
| WO | WO-03/095647 A2 | 11/2003 |
| WO | WO-2004/048570 A1 | 6/2004 |

(Continued)

OTHER PUBLICATIONS

Declaration by Judith C. van Deutekom executed Oct. 10, 2019, submitted in Invalidation Trial of JP6126983, on Oct. 10, 2019.
Vickers, Timothy A., et al., "Effects of RNA secondary structure on cellular antisense activity," Nucleic Acids Research, 2000, vol. 28, No. 6, pp. 1340-1347.
Johansson, Hans E., et al., "Target-specific arrest of mRNA translation by antisense 2'-O-alkyloligoribonucleotides," Nucleic Acids Research, 1994, vol. 22, No. 22, pp. 4591-4598.
Peyman, Anusch, et al., "Inhibition of Viral Growth by Antisense Oligonucleotides Directed against the IE110 and the UL30 mRNA of Herpes Simplex Virus Type-1," Biol. Chem. Hoppe-Seyler, Mar. 1995, vol. 376, pp. 195-198.

(Continued)

*Primary Examiner* — Sean McGarry
(74) *Attorney, Agent, or Firm* — Faegre Drinker Biddle & Reath LLP

(57) ABSTRACT

The present invention provides an oligomer which efficiently enables to cause skipping of the 53rd exon in the human dystrophin gene. Also provided is a pharmaceutical composition which causes skipping of the 53rd exon in the human dystrophin gene with a high efficiency.

18 Claims, 19 Drawing Sheets

Specification includes a Sequence Listing.

(56) References Cited

FOREIGN PATENT DOCUMENTS

| WO | WO-2004/083432 A1 | 9/2004 |
|---|---|---|
| WO | WO-2004/083446 A2 | 9/2004 |
| WO | WO-2006/000057 A1 | 1/2006 |
| WO | WO-2006/017522 A2 | 2/2006 |
| WO | WO-2006/112705 A2 | 10/2006 |
| WO | WO-2007/135105 A1 | 11/2007 |
| WO | WO-2008/036127 A2 | 3/2008 |
| WO | WO-2009/054725 A2 | 4/2009 |
| WO | WO-2009/139630 A2 | 11/2009 |
| WO | WO-2010/048586 A1 | 4/2010 |
| WO | WO-2010/050801 A1 | 5/2010 |
| WO | WO-2010/050802 A2 | 5/2010 |
| WO | WO-2010/123369 A1 | 10/2010 |
| WO | WO-2011/057350 A1 | 5/2011 |
| WO | WO-2012/109296 A1 | 8/2012 |
| WO | WO-2012/150960 A1 | 11/2012 |
| WO | WO-2013/112053 A1 | 8/2013 |
| WO | WO-2014/007620 A2 | 1/2014 |
| WO | WO-2014/100714 A1 | 6/2014 |
| WO | WO-2014/144978 A2 | 9/2014 |
| WO | WO-2014/153220 A2 | 9/2014 |
| WO | WO-2014/153240 A2 | 9/2014 |
| WO | WO-2016/025339 A2 | 2/2016 |
| WO | WO-2017/059131 A1 | 4/2017 |
| WO | WO-2017/062835 A2 | 4/2017 |
| WO | WO-2017/205496 A1 | 11/2017 |
| WO | WO-2017/205513 A1 | 11/2017 |
| WO | WO-2017/205879 A2 | 11/2017 |
| WO | WO-2017/205880 A1 | 11/2017 |
| WO | WO-2017/213854 A1 | 12/2017 |
| WO | WO-2017/205879 A3 | 1/2018 |
| WO | WO-2018/005805 A1 | 1/2018 |
| WO | WO-2018/091544 A1 | 5/2018 |
| WO | WO-2018/118599 A1 | 6/2018 |
| WO | WO-2018/118627 A1 | 6/2018 |
| WO | WO-2018/118662 A1 | 6/2018 |
| WO | WO-2019/046755 A1 | 3/2019 |
| WO | WO-2019/067975 A1 | 4/2019 |
| WO | WO-2019/067979 A1 | 4/2019 |
| WO | WO-2019/067981 A1 | 4/2019 |

OTHER PUBLICATIONS

Monia, Brett, P., et al., "Antitumor activity of a phosphorothioate antisense oligodeoxynucleotide targeted against C-raf kinase," Nature Medicine, Jun. 1996, vol. 2, No. 6, pp. 668-675.
Errington, Stephen J., et al., "Target selection for antisense oligonucleotide induced exon skipping in the dystrophin gene," J. Gene Med. 2003, vol. 5, pp. 518-527.
Morita, Koji, et al., "Synthesis and Properties of 2'-O,4'-C-Ethylene-Bridged Nucleic Acids (ENA) as Effective Antisense Oligonucleotides," Bioorganic & Medicinal Chemistry 2003, vol. 11, pp. 2211-2226.
Summerton, James E., "Morpholinos and PNAs compared," Letters in Peptide Science 2003, vol. 10, pp. 215-236.
Linda J. Popplewell et al., "Design of Phosphorodiamidate Morpholino Oligomers (PMOs) for the Induction of Exon Skipping of the Human DMD Gene," Mol. Ther., vol. 17, No. 3, Mar. 2009, pp. 554-561.
Linda J. Popplewell et al., "Comparative analysis of antisense oligonucleotide sequences targeting exon 53 of the human DMD gene: Implications for future clinical trials," Neuromuscular Disorders, vol. 20, No. 2, Feb. 2010, pp. 102-110.
Annemieke Aartsma-Rus et al., "Targeted exon skipping as a potential gene correction therapy for Duchenne muscular dystrophy," Neuromuscular Disorders, vol. 12, 2002, pp. S71-S77.
Steve D. Wilton et al., "Antisense Oligonucleotide-induced Exon Skipping Across the Human Dystrophin Gene Transcript," Mol Ther., vol. 15, No. 7, Jul. 2007, pp. 1288-1296.
Anthony P. Monaco et al., "An Explanation for the Phenotypic Differences between Patients Bearing Partial Deletions of the DMD Locus," Genomics, 1988; 2, pp. 90-95.
Masafumi Matsuo, "Duchenne / Becker muscular dystrophy: from molecular diagnosis to gene therapy," Brain & Development, 1996; 18, pp. 167-172.
International Search Report dated Oct. 11, 2011 in PCT/JP2011/070318 filed Aug. 31, 2011.
Mitrpant, et al., "By-passing the nonsense mutation in the $4^{CV}$ mouse model of muscular dystrophy by induced exon skipping", The Journal of Gene Medicine, Jan. 2009, vol. 11, No. 1, pp. 46-56.
Ito, et al., "Purine-Rich Exon Sequences Are Not Necessarily Splicing Enhancer Sequence in the Dystrophin Gene," Kobe J. Med. Sci. 47, Oct. 2001, pp. 193-202.
Muntoni, et al., "Dystrophin and mutations: one gene, several proteins, multiple phenotypes," The Lancet Neurology, Dec. 2003, vol. 2, pp. 731-740.
Muntoni, et al., "128th ENMC International Workshop on 'Preclinical optimization and Phase I/II Clinical Trials Using Antisense Oligonucleotides in Duchenne Muscular Dystrophy' Oct. 22-24, 2004, Naarden, The Netherlands," Neuromuscular Disorders, 2005, vol. 15, pp. 450-457.
Pramono et al BBRC 226 (1996) 445-449.
Tanaka et al Mol Cell Biol 1994, 1347-54.
Arechavala-Gomeza et al Hum Gen Thr 2007 798-810.
Aartsma-Rus et al Mol Ther 2009 17(3): 548-553.
Wu et al PLoS One 2011 e19906.
Declaration by Matthew J.A. Wood executed Nov. 18, 2014 in U.S. Patent Interference Nos. 106,007, 106,008, 106,113.
Sherratt et al Am J Hum Genet 1193 1007-15.
Roberts et al Lancet 1990 1523-26.
Roberts et al Hum Mut 1994 1-11.
Roberts et al Genomics 1993 536-538.
Dunckley et al Hum Mol Genet 1995, 1083-90.
Shiga et al J Clin Invest 1997 2204-10.
Wilton et al Neuromuscul Disord 1999, 330-8.
Coulter et al Mol Cell Biol 1997 2143-50.
Tian and Kole Mol Cell Biol 1995 6291-98.
Liu et al Gen&Dev 1998 1998-2012.
Applicant's letter to EPO in EP Application No. 12198517.0, dated Dec. 9, 2013.
Applicant's letter to EPO in EP Application No. 10177969.2, dated Mar. 7, 2016.
Ito et al., Journal of Japanese Society for Inherited Metabolic Diseases, vol. 15, No. 2, Nov. 1999, p. 162 (w/ English translation).
Annex B of Applicant's letter to EPO in EP Application No. 10177969.2, dated Mar. 7, 2016.
Patentee's letter in EPO Opposition of EP 1619249, T1383/13-3.3.08, dated Jun. 10, 2014.
Patentee's letter in EPO Opposition of EP 1619249, T1383/13-3.3.08, dated Jan. 8, 2014.
Deposition of Judith van Deutekom dated Mar. 11, 2015, in U.S. Patent Interference Nos. 106,007, 106,008.
FDA Briefing Document, Nov. 24, 2015.
Artsma-Rus et al Hum Mol Genet 2003, 907-14.
Van Deutekom N Eng J Med 2007 2677-86.
Van Deutekom et al Hum Mol Genet 2001, 1547-54.
Takeshima et al, JSHG 1999, the 44th Annual Meeting of the Japan Society of Human Genetics, Abstract, p. 83 (WC9) (w/ English translation).
Takeshima et al, Journal of Japanese Society for Inherited Metabolic Diseases, vol. 15, No. 2, No. 1999, p. 163 (101) (w/ English translation).
English Translation of JP2000-125448 filed Apr. 26, 2000, Priority document of EP1160318.
EPO register for EP1160318, obtained Nov. 14, 2016.
Mann et al J Gen Med 2002 644-54.
Declaration by Judith van Deutekom executed Feb. 16, 2015 in U.S. Patent Interference No. 106,007.
BioMarin Press Release, May 31, 2016.
Wilton & Fletcher Acta Myol 2005 222-9.
Aartsma-Rus & Ommen 2007 1609-24.
Heemskerk et al J Gen Med 2009 257-66.
Chan et al Clin Exp Phar Phys 2006 533-540.
Jarver et al Nuc Acid Ther 2014 37-47.
Aartsma-Rus et al Gen Thr 2004 1391-8.

(56) References Cited

OTHER PUBLICATIONS

Decision in U.S. Patent Interference No. 106,007, entered May 12, 2016.
Withdrawal and Reissue of Decision on Motions in U.S. Patent Interference No. 106,007, entered May 12, 2016.
Errata in U.S. Patent Interference No. 106,007, entered May 23, 2016.
English Translation of JP2000-256547, filed Aug. 25, 2000, Priority document of EP1191098.
Interlocutory decision in Opposition proceedings for EP1619249B, issued Apr. 15, 2013.
EPO Office Action issued in EP Application No. 01979073.2 (EP 1320597) Jan. 7, 2015.
Takeshima et al J Clin Invest 1995, 515-20.
Experimental Report submitted in EP Opposition Proceeding of EP 2602322, Nov. 28, 2016.
Takeshima et al Brain Dev 2001, 788-90.
Karras et al, Mol Pharm 2000, 380-7.
Wang et al PNAS 2000, 13714-9.
Watakabe et al Genes&Dev 1993, 407-18.
Lehninger, Principles of Biochemistry, 2000 3rd Edition, pp. 330-331.
Artsma-Rus et al Oligonucleotides 2010, 1-9.
Statement of Grounds of Appeal submitted in EP 1619249 B1, Aug. 23, 2013.
Artsma-Rus et al Oligonucleotides 2005, 284-97.
Letter submitted to EPO in EP 12198485.0, dated Oct. 23, 2014.
Experimental Report (comparative analysis of AONs for inducing the skipping exon 45) submitted in EP Opposition Proceeding of EP 2602322, May 22, 2017.
Decision of Opposition Division in EP 1619249 (EP Application No. 05076770.6), issued Apr. 15, 2013.
Reply to the Grounds of Appeal in EP 1619249 (EP Application No. 05076770.6), dated Jan. 8, 2014.
Experimental Report (in Silico-Wilton sequence) submitted in EP Opposition Proceeding of EP 2602322, May 22, 2017.
Comparative study on exon 44 submitted in Opposition Proceeding of EP 2602322, May 22, 2017.
Comparative study on exon 45 submitted in Opposition Proceeding of EP 2602322, May 22, 2017.
Comparative study on exon 52 submitted in Opposition Proceeding of EP 2602322, May 22, 2017.
Comparative study on exon 53 submitted in Opposition Proceeding of EP 2602322, May 22, 2017.
CV of Judith van Deutekom submitted in Opposition Proceeding of EP 2602322, May 22, 2017.
Letter to EPO in EP 2602322 (EP Application No. 12198517.0) dated Oct. 21, 2014.
Declaration by Judith van Deutekom submitted in Opposition Proceeding of EP 2602322, May 22, 2017.
Declaration by Judith van Deutekom submitted in Opposition Proceeding of EP 2602322, Apr. 20, 2018.
EPO Office Action in EP Application No. 12198517.0, dated Feb. 25, 2015.
Expert declaration by Judith van Deutekom submitted in Opposition Proceeding of EP 2602322, Apr. 20, 2018.
Map of AONs and Exon 53, submitted in Opposition Proceeding of EP 2602322, Apr. 20, 2018.
Evidence regarding inventorship assignment, screenshot search in the online Business Register of the Netherlands Chamber of Commerce for Leids Universitair Medisch Centrum, submitted in EP Opposition.
Evidence regarding inventorship assignment, screenshot search in the online Business Register of the Netherlands Chamber of Commerce for Academisch Ziekenhuis Leiden, submitted in EP Opposition.
Evidence regarding inventorship assignment, digitally certified extract from the Business Register of the Netherlands Chamber of Commerce, submitted in EP Opposition Proceeding of EP 2602322, May 23, 2018.
Declaration by Huibert Jacob Houtkooper, submitted in Opposition Proceeding of EP 2602322, Mar. 14, 2019.
Declaration of Lambert Oosting, submitted in Opposition Proceeding of EP 2602322, Mar. 14, 2019.
JPO Decision to maintain JP Patent No. 6126983 (w/ partial English translation), submitted in Opposition Proceeding of EP 2602322, Mar. 15, 2019.
Matsuo et al BBRC 170 (1990) 963-967.
Matsuo "Molecular biological study to establish the treatment for Duchenne muscular dystrophy" Research Report of Grants-in-Aid for Scientific Research, Ministry of Education, Mar. 1997 p. 1, 5-13 (w/ English translation).
Nakajima et al J Neurol (1991) 238:6-8.
Matsuo et al J Clin Invest. 1991;87(6):2127-2131.
Narita et al J Clin Invest. 1993;91(5):1862-1867.
Suryono et al Proceedings of the Association of American Physicians 108 308-314 (1996).
JP Patent application No. 2000-125448, filed Apr. 26, 2000 (w/ English translation).
Alan et al Hum Genet (1990) 86:45-48.
Matsuo "Establishment of treatment of Duchenne muscular dystrophy" Research Report of Grants-in-Aid for Scientific Research, Ministry of Education, Mar. 2000 p. 1, 5-11 (w/ English translation).
Marcusson et al., Molecular Biotechnology, vol. 12, 1999, 1-11.
Patentee's argument filed with JPO in JP Appl'n 2013-260728 on Apr. 13, 2015.
Decision of Rejection by JPO in JP Appl'n 2011-098952 on Aug. 21, 2013.
Patentee's argument filed with the JPO in Opposition of JP6126983 on Mar. 23, 2016 (w/ English translation).
David R Corey et al Genome Biology 2001 2(5) 1015.1-1015.3.
AU 2004903474 filed Jun. 28, 2004, priority document for PCT/AU05/000943.
Experimental report submitted in EPO Opposition in EP 2206781, Aug. 25, 2016.
Experimental report (D 8-1) submitted in EPO Opposition in EP 2206781, Sep. 29, 2017.
Map of target region, submitted in EPO Opposition in EP 2206781, Feb. 22, 2017.
Experimental report, submitted in EPO Opposition in EP 2206781, Feb. 22, 2017.
Declaration by Fred Schnell, dated Sep. 28, 2017, submitted in EPO Opposition in EP 2206781, Sep. 29, 201756.
Summerton et al Antisense&Nucleic acid drug development 7:187-195(1997).
Experimental report (D13), submitted in EPO Opposition in EP 2206781, Sep. 29, 2017.
Declaration by Fred Schnell submitted in EP2206781 Opposition on Apr. 25, 2018.
Amendment in response to Non-Final Office Action in U.S. Appl. No. 15/705,172, filed Jan. 5, 2018.
University of Western Australia Motion 1 filed in U.S. Patent Interference No. 106,007 (RES), on Nov. 18, 2014.
Prior et al., Human Genetics 92: 302-304 (1992).
Abstracts: 32nd European Muscle Conference, 'A link between fundamental research and therapeutic trials,' The Annual Meeting of the European Society for Muscle Research, Journal of Muscle Research and Cell.
Wells et al., FEBS Lett. 2003 vol. 552 145-149.
Cagliani et al., Human Genetics Jun. 2004 vol. 115 13-18.
Bremmer-Bout et al., Molecular Therapy 2004 vol. 10 232-240.
Abstracts of the Australasian Gene Therapy Society 4th Society Meeting, Journal of Gene Medicine Aug. 2005 vol. 7, 1113-1143.
Editorial by Wilton et al., Neuromuscular Disorders 2005 vol. 15, 399-402.
Specification of EP 12198465.2 filed Sep. 21, 2001.
Applicant's letter mailed Nov. 18, 2013 in EP 12198465.2.
Observations by third parties submitted in EP3018211 Jun. 13, 2018.
Communication from the Examining Division and Annex to the Communication issued in EP 3018211 on Nov. 9, 2018.
Harding et al., Molecular Therapy, vol. 15, No. 1, 157-166 (2007).

(56) References Cited

OTHER PUBLICATIONS

U.S. Appl. No. 61/108,416, filed Oct. 24, 2008, priority document of WO 2010/048586.
Nishida et al., Nature Communications, vol. 2, Article No. 308 (2011).
Appellant University of Western Australia's Statement of Grounds for Appeal submitted in EP 2 206 781, dated Apr. 27, 2018.
Nippon Shinyaku Co., Ltd.'s Reply to the Grounds of Appeal in EP 2 206 781, dated Sep. 6, 2018.
Opposition filed by Nippon Shinyaku Co., Ltd. in EP 2 206 781, dated Aug. 25, 2016.
The University of Western Australia's reply to Opposition in EP 2 206 781, dated Feb. 22, 2017.
EPO's Opposition Division's Preliminary Opinion in EP 2 206 781 B1, dated Mar. 30, 2017.
EPO's Decision on Opposition in EP 2 206 781 B1, dated Dec. 19, 2017.
Final Office Action in U.S. Appl. No. 16/243,926, dated May 15, 2019.
Amendments in EP 3 404 100, dated May 13, 2019.
Search opinion in EP 3 404 100, dated Oct. 24, 2018.

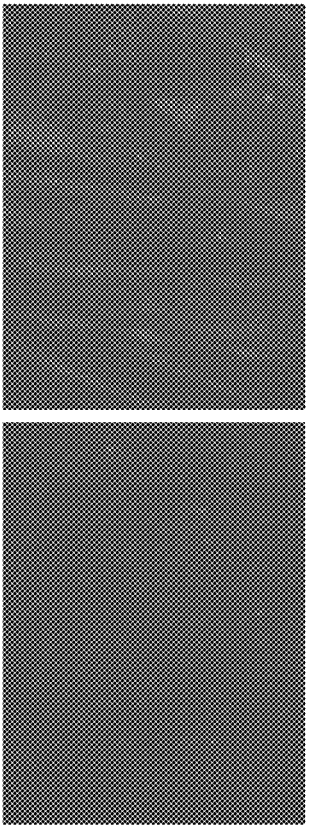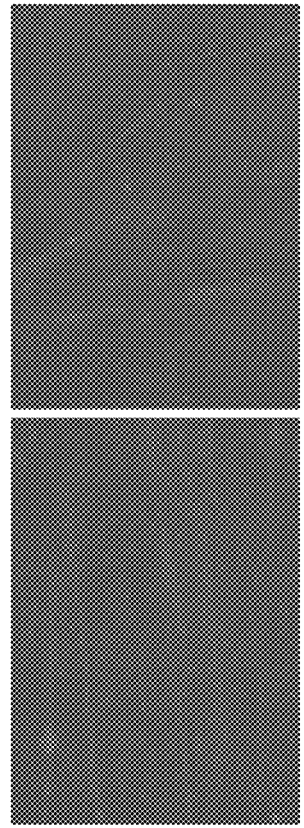
FIG. 7

SEQUENCE LISTING

```
<160> NUMBER OF SEQ ID NOS: 123

<210> SEQ ID NO 1
<211> LENGTH: 212
<212> TYPE: DNA
<213> ORGANISM: Homo sapiens

<400> SEQUENCE: 1
ttgaaagaat tcagaatcag tgggatgaag tacaagaaca ccttcagaac cggaggcaac      60
agttgaatga aatgttaaag gattcaacac aatggctgga agctaaggaa gaagctgagc     120
aggtcttagg acaggccaga gccaagcttg agtcatggaa ggagggtccc tatacagtag     180
atgcaatcca aagaaaatc acagaaacca ag                                    212

<210> SEQ ID NO 2
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 2
ccggttctga aggtgttctt gta                                              23

<210> SEQ ID NO 3
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 3
tccggttctg aaggtgttct tgta                                             24

<210> SEQ ID NO 4
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 4
ctccggttct gaaggtgttc ttgta                                            25

<210> SEQ ID NO 5
<211> LENGTH: 26
```

```
<212> TYPE: DNA
<213> ORGANISM: Artificial
<220> FEATURE:
<223> OTHER INFORMATION: Synthetic Nucleic Acid

<400> SEQUENCE: 5
cctccggttc tgaaggtgtt cttgta                                          26

<210> SEQ ID NO 6
<211> LENGTH: 27
<212> TYPE: DNA
<213> ORGANISM: Artificial
<220> FEATURE:
<223> OTHER INFORMATION: Synthetic Nucleic Acid

<400> SEQUENCE: 6
gcctccggtt ctgaaggtgt tcttgta                                         27

<210> SEQ ID NO 7
<211> LENGTH: 28
<212> TYPE: DNA
<213> ORGANISM: Artificial
<220> FEATURE:
<223> OTHER INFORMATION: Synthetic Nucleic Acid

<400> SEQUENCE: 7
tgcctccggt tctgaaggtg ttcttgta                                        28

<210> SEQ ID NO 8
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 8
ccggttctga aggtgttctt gt                                              22

<210> SEQ ID NO 9
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 9
tccggttctg aaggtgttct tgt                                             23

<210> SEQ ID NO 10
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 10
ctccggttct gaaggtgttc ttgt                                            24

<210> SEQ ID NO 11
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 11
```
cctccggttc tgaaggtgtt cttgt                                              25

<210> SEQ ID NO 12
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 12
gcctccggtt ctgaaggtgt tcttgt                                             26

<210> SEQ ID NO 13
<211> LENGTH: 27
<212> TYPE: DNA
<213> ORGANISM: Artificial
<220> FEATURE:
<223> OTHER INFORMATION: Synthetic Nucleic Acid

<400> SEQUENCE: 13
tgcctccggt tctgaaggtg ttcttgt                                            27

<210> SEQ ID NO 14
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 14
ccggttctga aggtgttctt g                                                  21

<210> SEQ ID NO 15
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 15
tccggttctg aaggtgttct tg                                                 22

<210> SEQ ID NO 16
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 16
ctccggttct gaaggtgttc ttg                                                23

<210> SEQ ID NO 17
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 17
cctccggttc tgaaggtgtt cttg                                               24

<210> SEQ ID NO 18
<211> LENGTH: 25
<212> TYPE: DNA
<213> ORGANISM: Artificial

```
<220> FEATURE:
<223> OTHER INFORMATION: Synthetic Nucleic Acid

<400> SEQUENCE: 18
gcctccggtt ctgaaggtgt tcttg                                            25

<210> SEQ ID NO 19
<211> LENGTH: 26
<212> TYPE: DNA
<213> ORGANISM: Artificial
<220> FEATURE:
<223> OTHER INFORMATION: Synthetic Nucleic Acid

<400> SEQUENCE: 19
tgcctccggt tctgaaggtg ttcttg                                           26

<210> SEQ ID NO 20
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 20
ccggttctga aggtgttctt                                                  20

<210> SEQ ID NO 21
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 21
tccggttctg aaggtgttct t                                                21

<210> SEQ ID NO 22
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 22
ctccggttct gaaggtgttc tt                                               22

<210> SEQ ID NO 23
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 23
cctccggttc tgaaggtgtt ctt                                              23

<210> SEQ ID NO 24
<211> LENGTH: 24
<212> TYPE: DNA
<213> ORGANISM: Artificial
<220> FEATURE:
<223> OTHER INFORMATION: Synthetic Nucleic Acid

<400> SEQUENCE: 24
gcctccggtt ctgaaggtgt tctt                                             24
```

<210> SEQ ID NO 25
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 25
tgcctccggt tctgaaggtg ttctt    25

<210> SEQ ID NO 26
<211> LENGTH: 19
<212> TYPE: DNA
<213> ORGANISM: Artificial
<220> FEATURE:
<223> OTHER INFORMATION: Synthetic Nucleic Acid

<400> SEQUENCE: 26
ccggttctga aggtgttct    19

<210> SEQ ID NO 27
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 27
tccggttctg aaggtgttct    20

<210> SEQ ID NO 28
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 28
ctccggttct gaaggtgttc t    21

<210> SEQ ID NO 29
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 29
cctccggttc tgaaggtgtt ct    22

<210> SEQ ID NO 30
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 30
gcctccggtt ctgaaggtgt tct    23

<210> SEQ ID NO 31
<211> LENGTH: 24
<212> TYPE: DNA
<213> ORGANISM: Artificial
<220> FEATURE:
<223> OTHER INFORMATION: Synthetic Nucleic Acid

```
<400> SEQUENCE: 31
tgcctccggt tctgaaggtg ttct                                          24

<210> SEQ ID NO 32
<211> LENGTH: 18
<212> TYPE: DNA
<213> ORGANISM: Artificial
<220> FEATURE:
<223> OTHER INFORMATION: Synthetic Nucleic Acid

<400> SEQUENCE: 32
ccggttctga aggtgttc                                                 18

<210> SEQ ID NO 33
<211> LENGTH: 19
<212> TYPE: DNA
<213> ORGANISM: Artificial
<220> FEATURE:
<223> OTHER INFORMATION: Synthetic Nucleic Acid

<400> SEQUENCE: 33
tccggttctg aaggtgttc                                                19

<210> SEQ ID NO 34
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 34
ctccggttct gaaggtgttc                                               20

<210> SEQ ID NO 35
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 35
cctccggttc tgaaggtgtt c                                             21

<210> SEQ ID NO 36
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 36
gcctccggtt ctgaaggtgt tc                                            22

<210> SEQ ID NO 37
<211> LENGTH: 23
<212> TYPE: DNA
<213> ORGANISM: Artificial
<220> FEATURE:
<223> OTHER INFORMATION: Synthetic Nucleic Acid

<400> SEQUENCE: 37
tgcctccggt tctgaaggtg ttc                                           23

<210> SEQ ID NO 38
```

```
<211> LENGTH: 31
<212> TYPE: DNA
<213> ORGANISM: Artificial
<220> FEATURE:
<223> OTHER INFORMATION: Synthetic Nucleic Acid

<400> SEQUENCE: 38
cattcaactg ttgcctccgg ttctgaaggt g                                    31

<210> SEQ ID NO 39
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 39
ttgcctccgg ttctgaaggt gttcttgtac                                     30

<210> SEQ ID NO 40
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 40
aggatttgga acagaggcgt c                                              21

<210> SEQ ID NO 41
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 41
gtctgccact ggcggaggtc                                                20

<210> SEQ ID NO 42
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 42
catcaagcag aaggcaacaa                                                20

<210> SEQ ID NO 43
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 43
gaagtttcag ggccaagtca                                                20

<210> SEQ ID NO 44
<211> LENGTH: 963
<212> TYPE: DNA
<213> ORGANISM: Homo sapiens

<400> SEQUENCE: 44
atggagctac tgtcgccacc gctccgcgac gtagacctga cggccccga cggctctctc     60
```

```
tgctcctttg ccacaacgga cgacttctat gacgacccgt gtttcgactc cccggacctg    120
cgcttcttcg aagacctgga cccgcgcctg atgcacgtgg gcgcgctcct gaaacccgaa    180
gagcactcgc acttccccgc ggcggtgcac ccggccccgg gcgcacgtga ggacgagcat    240
gtgcgcgcgc ccagcgggca ccaccaggcg ggccgctgcc tactgtgggc ctgcaaggcg    300
tgcaagcgca agaccaccaa cgccgaccgc gcaaggccg ccaccatgcg cgagcggcgc    360
cgcctgagca agtaaatga ggcctttgag acactcaagc gctgcacgtc gagcaatcca    420
aaccagcggt tgcccaaggt ggagatcctg cgcaacgcca tccgctatat cgagggcctg    480
caggctctgc tgcgcgacca ggacgccgcg ccccctggcg ccgcagccgc cttctatgcg    540
ccgggcccgc tgccccgggg ccgcggcggc gagcactaca gcggcgactc cgacgcgtcc    600
agcccgcgct ccaactgctc cgacggcatg atggactaca cggcccccc gagcggcgcc    660 cggcggcgga actgctacga aggcgcctac tacaacgagg cgcccagcga acccaggccc    720
gggaagagtg cggcggtgtc gagcctagac tgcctgtcca gcatcgtgga gcgcatctcc    780
accgagagcc ctgcggcgcc cgccctcctg ctggcggacg tgccttctga gtcgcctccg    840
cgcaggcaag aggctgccgc ccccagcgag ggagagagca gcggcgaccc cacccagtca    900
ccggacgccg ccccgcagtg ccctgcgggt gcgaacccca acccgatata ccaggtgctc    960
tga                                                                   963
```

<210> SEQ ID NO 45
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 45

```
cgggcttgga cagaacttac                                                  20
```

<210> SEQ ID NO 46
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 46

```
tccttacggg tagcatcctg                                                  20
```

<210> SEQ ID NO 47
<211> LENGTH: 25
<212> TYPE: DNA
<213> ORGANISM: Artificial
<220> FEATURE:
<223> OTHER INFORMATION: Synthetic DNA

<400> SEQUENCE: 47

```
ctgaaggtgt tcttgtactt catcc                                            25
```

<210> SEQ ID NO 48
<211> LENGTH: 19
<212> TYPE: DNA
<213> ORGANISM: Artificial
<220> FEATURE:
<223> OTHER INFORMATION: Synthetic DNA

<400> SEQUENCE: 48

```
tgttgagaaa tggcggcgt                                                    19
```

<210> SEQ ID NO 49
<211> LENGTH: 31
<212> TYPE: RNA
<213> ORGANISM: Artificial
<220> FEATURE:
<223> OTHER INFORMATION: Synthetic Nucleic Acid

<400> SEQUENCE: 49

```
cauucaacug uugccuccgg uucugaaggu g                                      31
```

<210> SEQ ID NO 50
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 50

```
ucccacugau ucugaauucu uucaa                                             25
```

<210> SEQ ID NO 51
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 51

```
cuucauccca cugauucuga auucu                                             25
```

<210> SEQ ID NO 52
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 52

```
uuguacuuca ucccacugau ucuga                                             25
```

<210> SEQ ID NO 53
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 53

```
uguucuugua cuucauccca cugau                                             25
```

<210> SEQ ID NO 54
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 54

```
gaagguguuc uuguacuuca uccca                                             25
```

<210> SEQ ID NO 55
<211> LENGTH: 25
<212> TYPE: RNA
<213> ORGANISM: Artificial

<220> FEATURE:
<223> OTHER INFORMATION: Synthetic Nucleic Acid

<400> SEQUENCE: 55
guucugaagg uguucuugua cuuca        25

<210> SEQ ID NO 56
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 56
cuccgguucu gaagguguuc uugua        25

<210> SEQ ID NO 57
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 57
guugccuccg guucugaagg uguuc        25

<210> SEQ ID NO 58
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 58
caacuguugc cuccgguucu gaagg        25

<210> SEQ ID NO 59
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 59
ucauucaacu guugccuccg guucu        25

<210> SEQ ID NO 60
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 60
acauuucauu caacuguugc cuccg        25

<210> SEQ ID NO 61
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 61
cuuuaacauu ucauucaacu guugc        25

```
<210> SEQ ID NO 62
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 62
gaauccuuua acauuucauu caacu                                              25

<210> SEQ ID NO 63
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 63
guguugaauc cuuuaacauu ucauu                                              25

<210> SEQ ID NO 64
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 64
ccauuguguu gaauccuuua acauu                                              25

<210> SEQ ID NO 65
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 65
uccagccauu guugaauc cuuua                                                25

<210> SEQ ID NO 66
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 66
uagcuuccag ccauuguguu gaauc                                              25

<210> SEQ ID NO 67
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 67
uuccuuagcu uccagccauu guguu                                              25

<210> SEQ ID NO 68
<211> LENGTH: 25
<212> TYPE: RNA
<213> ORGANISM: Artificial
<220> FEATURE:
<223> OTHER INFORMATION: Synthetic Nucleic Acid
```

<400> SEQUENCE: 68
gcuucuuccu uagcuuccag ccauu                                  25

<210> SEQ ID NO 69
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 69
gcucagcuuc uuccuuagcu uccag                                  25

<210> SEQ ID NO 70
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 70
gaccugcuca gcuucuuccu uagcu                                  25

<210> SEQ ID NO 71
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 71
ccuaagaccu gcucagcuuc uuccu                                  25

<210> SEQ ID NO 72
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 72
ccuguccuaa gaccugcuca gcuuc                                  25

<210> SEQ ID NO 73
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 73
ucuggccugu ccuaagaccu gcuca                                  25

<210> SEQ ID NO 74
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 74
uuggcucugg ccuguccuaa gaccu                                  25

<210> SEQ ID NO 75

```
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 75
caagcuuggc ucuggccugu ccuaa                                              25

<210> SEQ ID NO 76
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 76
ugacucaagc uuggcucugg ccugu                                              25

<210> SEQ ID NO 77
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 77
uuccaugacu caagcuuggc ucugg                                              25

<210> SEQ ID NO 78
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 78
ccuccuucca ugacucaagc uuggc                                              25

<210> SEQ ID NO 79
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 79
gggacccucc uuccaugacu caagc                                              25

<210> SEQ ID NO 80
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 80
guauagggac ccuccuucca ugacu                                              25

<210> SEQ ID NO 81
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 81
```

```
cuacuguaua gggacccucc uucca                                    25

<210> SEQ ID NO 82
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 82
ugcaucuacu guauagggac ccucc                                    25

<210> SEQ ID NO 83
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 83
uggauugcau cuacuguaua gggac                                    25

<210> SEQ ID NO 84
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 84
ucuuuuggau ugcaucuacu guaua                                    25

<210> SEQ ID NO 85
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 85
gauuuucuuu uggauugcau cuacu                                    25

<210> SEQ ID NO 86
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 86
ucugugauuu ucuuuuggau ugcau                                    25

<210> SEQ ID NO 87
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 87
ugguuucugu gauuucuuu uggau                                     25

<210> SEQ ID NO 88
<211> LENGTH: 25
<212> TYPE: RNA
```

```
<213> ORGANISM: Artificial
<220> FEATURE:
<223> OTHER INFORMATION: Synthetic Nucleic Acid

<400> SEQUENCE: 88
ccuuagcuuc cagccauugu guuga                                         25

<210> SEQ ID NO 89
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 89
ucuuccuuag cuuccagcca uugug                                         25

<210> SEQ ID NO 90
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 90
ggcucuggcc uguccuaaga ccugc                                         25

<210> SEQ ID NO 91
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 91
agcuuggcuc uggccugucc uaaga                                         25

<210> SEQ ID NO 92
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 92
cucaagcuug gcucuggccu guccu                                         25

<210> SEQ ID NO 93
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 93
gacccuccuu ccaugacuca agcuu                                         25

<210> SEQ ID NO 94
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 94
auagggaccc uccuuccaug acuca                                         25
```

```
<210> SEQ ID NO 95
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 95
cuguauaggg acccuccuuc cauga                                   25

<210> SEQ ID NO 96
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 96
ugugauuuuc uuuggauug caucu                                    25

<210> SEQ ID NO 97
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 97
guuucuguga uuucuuuug gauug                                    25

<210> SEQ ID NO 98
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 98
cuugguuucu gugauuuucu uuugg                                   25

<210> SEQ ID NO 99
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 99
ccgguucuga agguguucuu guacu                                   25

<210> SEQ ID NO 100
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 100
uccgguucug aagguguucu uguac                                   25

<210> SEQ ID NO 101
<211> LENGTH: 25
<212> TYPE: RNA
<213> ORGANISM: Artificial
<220> FEATURE:
```

<223> OTHER INFORMATION: Synthetic Nucleic Acid

<400> SEQUENCE: 101
ccuccgguuc ugaaggucuu cuugu        25

<210> SEQ ID NO 102
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 102
gccuccgguu cugaaggugu ucuug        25

<210> SEQ ID NO 103
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 103
ugccuccggu ucugaaggug uucuu        25

<210> SEQ ID NO 104
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 104
uugccuccgg uucugaaggu guucu        25

<210> SEQ ID NO 105
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 105
uguugccucc gguucugaag guguu        25

<210> SEQ ID NO 106
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 106
cuguugccuc cgguucugaa ggugu        25

<210> SEQ ID NO 107
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 107
acuguugccu ccgguucuga aggug        25

```
<210> SEQ ID NO 108
<211> LENGTH: 25
<212> TYPE: RNA
<213> ORGANISM: Artificial
<220> FEATURE:
<223> OTHER INFORMATION: Synthetic Nucleic Acid

<400> SEQUENCE: 108
aacuguugcc uccgguucug aaggu                                              25

<210> SEQ ID NO 109
<211> LENGTH: 30
<212> TYPE: RNA
<213> ORGANISM: Artificial
<220> FEATURE:
<223> OTHER INFORMATION: Synthetic Nucleic Acid

<400> SEQUENCE: 109
uguugccucc gguucugaag guguucuugu                                         30

<210> SEQ ID NO 110
<211> LENGTH: 20
<212> TYPE: RNA
<213> ORGANISM: Artificial
<220> FEATURE:
<223> OTHER INFORMATION: Synthetic Nucleic Acid

<400> SEQUENCE: 110
gguucugaag guguucuugu                                                    20

<210> SEQ ID NO 111
<211> LENGTH: 20
<212> TYPE: RNA
<213> ORGANISM: Artificial
<220> FEATURE:
<223> OTHER INFORMATION: Synthetic Nucleic Acid

<400> SEQUENCE: 111
uccgguucug aagguguucu                                                    20

<210> SEQ ID NO 112
<211> LENGTH: 20
<212> TYPE: RNA
<213> ORGANISM: Artificial
<220> FEATURE:
<223> OTHER INFORMATION: Synthetic Nucleic Acid

<400> SEQUENCE: 112
ccuccgguuc ugaagguguu                                                    20

<210> SEQ ID NO 113
<211> LENGTH: 20
<212> TYPE: RNA
<213> ORGANISM: Artificial
<220> FEATURE:
<223> OTHER INFORMATION: Synthetic Nucleic Acid

<400> SEQUENCE: 113
uugccuccgg uucugaaggu                                                    20

<210> SEQ ID NO 114
<211> LENGTH: 20
<212> TYPE: RNA
<213> ORGANISM: Artificial
<220> FEATURE:
<223> OTHER INFORMATION: Synthetic Nucleic Acid
```

<400> SEQUENCE: 114
uguugccucc gguucugaag                                          20

<210> SEQ ID NO 115
<211> LENGTH: 18
<212> TYPE: RNA
<213> ORGANISM: Artificial
<220> FEATURE:
<223> OTHER INFORMATION: Synthetic Nucleic Acid

<400> SEQUENCE: 115
uucugaaggu guucuugu                                            18

<210> SEQ ID NO 116
<211> LENGTH: 18
<212> TYPE: RNA
<213> ORGANISM: Artificial
<220> FEATURE:
<223> OTHER INFORMATION: Synthetic Nucleic Acid

<400> SEQUENCE: 116
cgguucugaa gguguucu                                            18

<210> SEQ ID NO 117
<211> LENGTH: 18
<212> TYPE: RNA
<213> ORGANISM: Artificial
<220> FEATURE:
<223> OTHER INFORMATION: Synthetic Nucleic Acid

<400> SEQUENCE: 117
cuccgguucu gaaggugu                                            18

<210> SEQ ID NO 118
<211> LENGTH: 18
<212> TYPE: RNA
<213> ORGANISM: Artificial
<220> FEATURE:
<223> OTHER INFORMATION: Synthetic Nucleic Acid

<400> SEQUENCE: 118
ugccuccggu ucugaagg                                            18

<210> SEQ ID NO 119
<211> LENGTH: 18
<212> TYPE: RNA
<213> ORGANISM: Artificial
<220> FEATURE:
<223> OTHER INFORMATION: Synthetic Nucleic Acid

<400> SEQUENCE: 119
uguugccucc gguucuga                                            18

<210> SEQ ID NO 120
<211> LENGTH: 15
<212> TYPE: RNA
<213> ORGANISM: Artificial
<220> FEATURE:
<223> OTHER INFORMATION: Synthetic Nucleic Acid

<400> SEQUENCE: 120
uucugaaggu guucu                                               15

<210> SEQ ID NO 121
<211> LENGTH: 15

```
<212> TYPE: RNA
<213> ORGANISM: Artificial
<220> FEATURE:
<223> OTHER INFORMATION: Synthetic Nucleic Acid

<400> SEQUENCE: 121
uccgguucug aaggu                                                    15

<210> SEQ ID NO 122
<211> LENGTH: 15
<212> TYPE: RNA
<213> ORGANISM: Artificial
<220> FEATURE:
<223> OTHER INFORMATION: Synthetic Nucleic Acid

<400> SEQUENCE: 122
uugccuccgg uucug                                                    15

<210> SEQ ID NO 123
<211> LENGTH: 18
<212> TYPE: RNA
<213> ORGANISM: Artificial
<220> FEATURE:
<223> OTHER INFORMATION: Synthetic Nucleic Acid

<400> SEQUENCE: 123
cuguugccuc cgguucug                                                 18
```

ANTISENSE NUCLEIC ACIDS

CROSS REFERENCE TO RELATED APPLICATIONS

This is a Continuation of copending application Ser. No. 15/619,996, filed Jun. 12, 2017, which is a Continuation of application Ser. No. 14/615,504, filed Feb. 6, 2015 (now U.S. Pat. No. 9,708,361 issued Jul. 18, 2017), which is a Continuation of application Ser. No. 13/819,520, filed Apr. 10, 2013 (now U.S. Pat. No. 9,079,934 issued Jul. 14, 2015), which is a PCT National Stage of PCT/JP2011/070318 filed Aug. 31, 2011, which claims priority to JP Application No. 2010-196032 filed Sep. 1, 2010, all of which are incorporated by reference in their entireties.

SEQUENCE LISTING

The instant application contains a Sequence Listing which has been submitted in ASCII format via EFS-Web and is hereby incorporated by reference in its entirety. Said ASCII copy, created on Apr. 9, 2019, is named 209658_0001_06_US_588192_ST25.txt and is 24,722 bytes in size.

TECHNICAL FIELD

The present invention relates to an antisense oligomer which causes skipping of exon 53 in the human dystrophin gene, and a pharmaceutical composition comprising the oligomer.

BACKGROUND ART

Duchenne muscular dystrophy (DMD) is the most frequent form of hereditary progressive muscular dystrophy that affects one in about 3,500 newborn boys. Although the motor functions are rarely different from healthy humans in infancy and childhood, muscle weakness is observed in children from around 4 to 5 years old. Then, muscle weakness progresses to the loss of ambulation by about 12 years old and death due to cardiac or respiratory insufficiency in the twenties. DMD is such a severe disorder. At present, there is no effective therapy for DMD available, and it has been strongly desired to develop a novel therapeutic agent.

DMD is known to be caused by a mutation in the dystrophin gene. The dystrophin gene is located on X chromosome and is a huge gene consisting of 2.2 million DNA nucleotide pairs. DNA is transcribed into mRNA precursors, and introns are removed by splicing to synthesize mRNA in which 79 exons are joined together. This mRNA is translated into 3,685 amino acids to produce the dystrophin protein. The dystrophin protein is associated with the maintenance of membrane stability in muscle cells and necessary to make muscle cells less fragile. The dystrophin gene from patients with DMD contains a mutation and hence, the dystrophin protein, which is functional in muscle cells, is rarely expressed. Therefore, the structure of muscle cells cannot be maintained in the body of the patients with DMD, leading to a large influx of calcium ions into muscle cells. Consequently, an inflammation-like response occurs to promote fibrosis so that muscle cells can be regenerated only with difficulty.

Becker muscular dystrophy (BMD) is also caused by a mutation in the dystrophin gene. The symptoms involve muscle weakness accompanied by atrophy of muscle but are typically mild and slow in the progress of muscle weakness, when compared to DMD. In many cases, its onset is in adulthood. Differences in clinical symptoms between DMD and BMD are considered to reside in whether the reading frame for amino acids on the translation of dystrophin mRNA into the dystrophin protein is disrupted by the mutation or not (Non-Patent Document 1). More specifically, in DMD, the presence of mutation shifts the amino acid reading frame so that the expression of functional dystrophin protein is abolished, whereas in BMD the dystrophin protein that functions, though imperfectly, is produced because the amino acid reading frame is preserved, while a part of the exons are deleted by the mutation.

Exon skipping is expected to serve as a method for treating DMD. This method involves modifying splicing to restore the amino acid reading frame of dystrophin mRNA and induce expression of the dystrophin protein having the function partially restored (Non-Patent Document 2). The amino acid sequence part, which is a target for exon skipping, will be lost. For this reason, the dystrophin protein expressed by this treatment becomes shorter than normal one but since the amino acid reading frame is maintained, the function to stabilize muscle cells is partially retained. Consequently, it is expected that exon skipping will lead DMD to the similar symptoms to that of BMD which is milder. The exon skipping approach has passed the animal tests using mice or dogs and now is currently assessed in clinical trials on human DMD patients.

The skipping of an exon can be induced by binding of antisense nucleic acids targeting either 5' or 3' splice site or both sites, or exon-internal sites. An exon will only be included in the mRNA when both splice sites thereof are recognized by the spliceosome complex. Thus, exon skipping can be induced by targeting the splice sites with antisense nucleic acids. Furthermore, the binding of an SR protein to an exonic splicing enhancer (ESE) is considered necessary for an exon to be recognized by the splicing mechanism. Accordingly, exon skipping can also be induced by targeting ESE.

Since a mutation of the dystrophin gene may vary depending on DMD patients, antisense nucleic acids need to be desined based on the site or type of respective genetic mutation. In the past, antisense nucleic acids that induce exon skipping for all 79 exons were produced by Steve Wilton, et al., University of Western Australia (Non-Patent Document 3), and the antisense nucleic acids which induce exon skipping for 39 exons were produced by Annemieke Aartsma-Rus, et al., Netherlands (Non-Patent Document 4).

It is considered that approximately 8% of all DMD patients may be treated by skipping the 53rd exon (hereinafter referred to as "exon 53"). In recent years, a plurality of research organizations reported on the studies where exon 53 in the dystrophin gene was targeted for exon skipping (Patent Documents 1 to 4; Non-Patent Document 5). However, a technique for skipping exon 53 with a high efficiency has not yet been established.

Patent Document 1: International Publication WO 2006/000057
Patent Document 2: International Publication WO 2004/048570
Patent Document 3: US 2010/0168212
Patent Document 4: International Publication WO 2010/048586
Non-Patent Document 1: Monaco A. P. et al., Genomics 1988; 2: p. 90-95
Non-Patent Document 2: Matsuo M., Brain Dev 1996; 18: p. 167-172

Non-Patent Document 3: Wilton S. D., e t al., Molecular Therapy 2007: 15: p. 1288-96

Non-Patent Document 4: Annemieke Aartsma-Rus et al., (2002) Neuromuscular Disorders 12: S71-S77

Non-Patent Document 5: Linda J. Popplewell et al., (2010) Neuromuscular Disorders, vol. 20, no. 2, p. 102-10

DISCLOSURE OF THE INVENTION

Under the foregoing circumstances, antisense oligomers that strongly induce exon 53 skipping in the dystrophin gene and muscular dystrophy therapeutics comprising oligomers thereof have been desired.

As a result of detailed studies of the structure of the dystrophin gene, the present inventors have found that exon 53 skipping can be induced with a high efficiency by targeting the sequence consisting of the 32nd to the 56th nucleotides from the 5' end of exon 53 in the mRNA precursor (hereinafter referred to as "pre-mRNA") in the dystrophin gene with antisense oligomers. Based on this finding, the present inventors have accomplished the present invention.

That is, the present invention is as follows.

[1] An antisense oligomer which causes skipping of the 53rd exon in the human dystrophin gene, consisting of a nucleotide sequence complementary to any one of the sequences consisting of the 31st to the 53rd, the 31st to the 54th, the 31st to the 55th, the 31st to the 56th, the 31st to the 57th, the 31st to the 58th, the 32nd to the 53rd, the 32nd to the 54th, the 32nd to the 55th, the 32nd to the 56th, the 32nd to the 57th, the 32nd to the 58th, the 33rd to the 53rd, the 33rd to the 54th, the 33rd to the 55th, the 33rd to the 56th, the 33rd to the 57th, the 33rd to the 58th, the 34th to the 53rd, the 34th to the 54th, the 34th to the 55th, the 34th to the 56th, the 34th to the 57th, the 34th to the 58th, the 35th to the 53rd, the 35th to the 54th, the 35th to the 55th, the 35th to the 56th, the 35th to the 57th, the 35th to the 58th, the 36th to the 53rd, the 36th to the 54th, the 36th to the 55th, the 36th to the 56th, the 36th to the 57th, or the 36th to the 58th nucleotides, from the 5' end of the 53rd exon in the human dystrophin gene.

[2] The antisense oligomer according to [1] above, which is an oligonucleotide.

[3] The antisense oligomer according to [2] above, wherein the sugar moiety and/or the phosphate-binding region of at least one nucleotide constituting the oligonucleotide is modified.

[4] The antisense oligomer according to [3] above, wherein the sugar moiety of at least one nucleotide constituting the oligonucleotide is a ribose in which the 2'-OH group is replaced by any one selected from the group consisting of OR, R, R'OR, SH, SR, $NH_2$, NHR, $NR_2$, $N_3$, CN, F, Cl, Br and I (wherein R is an alkyl or an aryl and R' is an alkylene).

[5] The antisense oligomer according to [3] or [4] above, wherein the phosphate-binding region of at least one nucleotide constituting the oligonucleotide is any one selected from the group consisting of a phosphorothioate bond, a phosphorodithioate bond, an alkylphosphonate bond, a phosphoramidate bond and a boranophosphate bond.

[6] The antisense oligomer according to [1] above, which is a morpholino oligomer.

[7] The antisense oligomer according to [6] above, which is a phosphorodiamidate morpholino oligomer.

[8] The antisense oligomer according to any one of [1] to [7] above, wherein the 5' end is any one of the groups of chemical formulae (1) to (3) below:

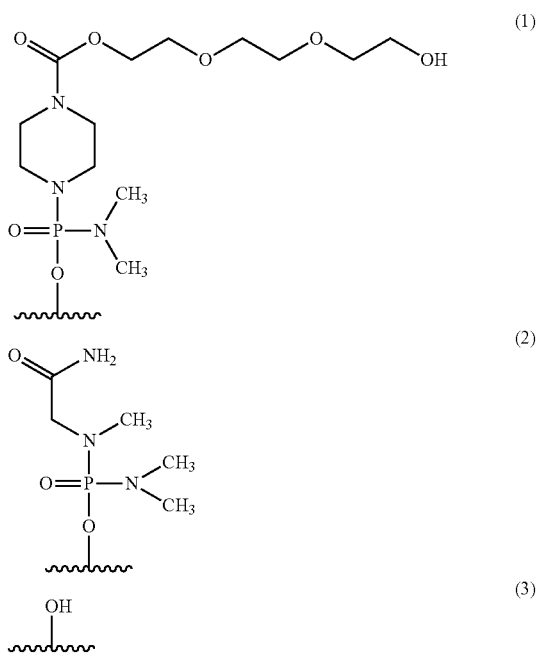

[9] The antisense oligomer according to any one of [1] to [8] above, consisting of a nucleotide sequence complementary to the sequences consisting of the 32nd to the 56th or the 36th to the 56th nucleotides from the 5' end of the 53rd exon in the human dystrophin gene.

[10] The antisense oligomer according to any one of [1] to [8] above, consisting of the nucleotide sequence shown by any one selected from the group consisting of SEQ ID NOS: 2 to 37.

[11] The antisense oligomer according to any one of [1] to [8] above, consisting of the nucleotide sequence shown by any one selected from the group consisting of SEQ ID NOS: 11, 17, 23, 29 and 35.

[12] The antisense oligomer according to any one of [1] to [8] above, consisting of the nucleotide sequence shown by SEQ ID NO: 11 or 35.

[13] A pharmaceutical composition for the treatment of muscular dystrophy, comprising as an active ingredient the antisense oligomer according to any one of [1] to [12] above, or a pharmaceutically acceptable salt or hydrate thereof.

The antisense oligomer of the present invention can induce exon 53 skipping in the human dystrophin gene with a high efficiency. In addition, the symptoms of Duchenne muscular dystrophy can be effectively alleviated by administering the pharmaceutical composition of the present invention.

BRIEF DESCRIPTION OF DRAWINGS

FIG. 7 shows the efficiency of exon 53 skipping in the human dystrophin gene in the cells where human myoD gene is introduced into fibroblasts from human DMD patient (with deletion of exons 45-52 or deletion of exons 48-52) to induce differentiation into muscle cells.

BEST MODE FOR CARRYING OUT THE INVENTION

Figure 1:
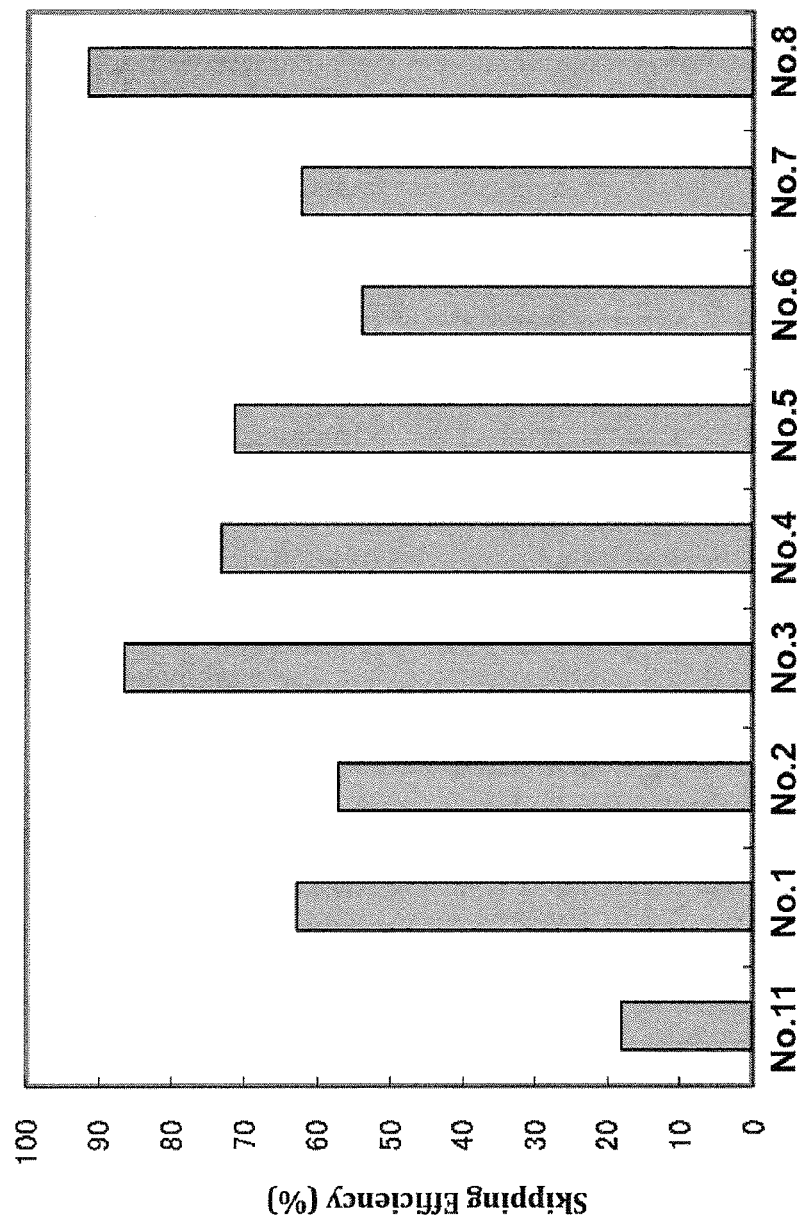
FIG. 1 shows the efficiency of exon 53 skipping in the human dystrophin gene in human rhabdomyosarcoma cell line (RD cells).

Hereinafter, the present invention is described in detail. The embodiments described below are intended to be presented by way of example merely to describe the invention but not limited only to the following embodiments. The present invention may be implemented in various ways without departing from the gist of the invention.

All of the publications, published patent applications, patents and other patent documents cited in the specification are herein incorporated by reference in their entirety. The specification hereby incorporates by reference the contents of the specification and drawings in the Japanese Patent Application (No. 2010-196032) filed Sep. 1, 2010, from which the priority was claimed.

1. Antisense Oligomer

The present invention provides the antisense oligomer (hereinafter referred to as the "oligomer of the present invention") which causes skipping of the 53rd exon in the human dystrophin gene, consisting of a nucleotide sequence complementary to any one of the sequences (hereinafter also referred to as "target sequences") consisting of the 31st to the 53rd, the 31st to the 54th, the 31st to the 55th, the 31st to the 56th, the 31st to the 57th, the 31st to the 58th, the 32nd to the 53rd, the 32nd to the 54th, the 32nd to the 55th, the 32nd to the 56th, the 32nd to the 57th, the 32nd to the 58th, the 33rd to the 53rd, the 33rd to the 54th, the 33rd to the 55th, the 33rd to the 56th, the 33rd to the 57th, the 33rd to the 58th, the 34th to the 53rd, the 34th to the 54th, the 34th to the 55th, the 34th to the 56th, the 34th to the 57th, the 34th to the 58th, the 35th to the 53rd, the 35th to the 54th, the 35th to the 55th, the 35th to the 56th, the 35th to the 57th, the 35th to the 58th, the 36th to the 53rd, the 36th to the 54th, the 36th to the 55th, the 36th to the 56th, the 36th to the 57th, or the 36th to the 58th nucleotides, from the 5' end of the 53rd exon in the human dystrophin gene.

[Exon 53 in Human Dystrophin Gene]

In the present invention, the term "gene" is intended to mean a genomic gene and also include cDNA, mRNA precursor and mRNA. Preferably, the gene is mRNA precursor, i.e., pre-mRNA.

In the human genome, the human dystrophin gene locates at locus Xp21.2. The human dystrophin gene has a size of 3.0 Mbp and is the largest gene among known human genes. However, the coding regions of the human dystrophin gene are only 14 kb, distributed as 79 exons throughout the human dystrophin gene (Roberts, R G., et al., Genomics, 16: 536-538 (1993)). The pre-mRNA, which is the transcript of the human dystrophin gene, undergoes splicing to generate mature mRNA of 14 kb. The nucleotide sequence of human wild-type dystrophin gene is known (GenBank Accession No. NM_004006).

The nucleotide sequence of exon 53 in the human wild-type dystrophin gene is represented by SEQ ID NO: 1.

The oligomer of the present invention is designed to cause skipping of exon 53 in the human dystrophin gene, thereby modifying the protein encoded by DMD type of dystrophin gene into the BMD type of dystrophin protein. Accordingly, exon 53 in the dystrophin gene that is the target of exon skipping by the oligomer of the present invention includes both wild and mutant types.

Specifically, exon 53 mutants of the human dystrophin gene include the polynucleotides defined in (a) or (b) below.

(a) A polynucleotide that hybridizes under stringent conditions to a polynucleotide consisting of a nucleotide sequence complementary to the nucleotide sequence of SEQ ID NO: 1; and, (b) A polynucleotide consisting of a nucleotide sequence having at least 90% identity with the nucleotide sequence of SEQ ID NO: 1.

As used herein, the term "polynucleotide" is intended to mean DNA or RNA.

As used herein, the term "polynucleotide that hybridizes under stringent conditions" refers to, for example, a polynucleotide obtained by colony hybridization, plaque hybridization, Southern hybridization or the like, using as a probe all or part of a polynucleotide consisting of a nucleotide sequence complementary to the nucleotide sequence of, e.g., SEQ ID NO: 1. The hybridization method which may be used includes methods described in, for example, "Sambrook & Russell, Molecular Cloning: A Laboratory Manual Vol. 3, Cold Spring Harbor, Laboratory Press 2001," "Ausubel, Current Protocols in Molecular Biology, John Wiley & Sons 1987-1997," etc.

As used herein, the term "complementary nucleotide sequence" is not limited only to nucleotide sequences that form Watson-Crick pairs with target nucleotide sequences, but is intended to also include nucleotide sequences which form Wobble base pairs. As used herein, the term Watson-Crick pair refers to a pair of nucleobases in which hydrogen bonds are formed between adenine-thymine, adenine-uracil or guanine-cytosine, and the term Wobble base pair refers to a pair of nucleobases in which hydrogen bonds are formed between guanine-uracil, inosine-uracil, inosine-adenine or inosine-cytosine. As used herein, the term "complementary nucleotide sequence" does not only refers to a nucleotide sequence 100% complementary to the target nucleotide sequence but also refers to a complementary nucleotide sequence that may contain, for example, 1 to 3, 1 or 2, or one nucleotide non-complementary to the target nucleotide sequence.

As used herein, the term "stringent conditions" may be any of low stringent conditions, moderate stringent conditions or high stringent conditions. The term "low stringent conditions" are, for example, 5×SSC, 5×Denhardt's solution, 0.5% SDS, 50% formamide at 32° C. The term "moderate stringent conditions" are, for example, 5×SSC, 5×Denhardt's solution, 0.5% SDS, 50% formamide at 42° C., or 5×SSC, 1% SDS, 50 mM Tris-HCl (pH 7.5), 50% formamide at 42° C. The term "high stringent conditions" are, for example, 5×SSC, 5×Denhardt's solution, 0.5% SDS, 50% formamide at 50° C. or 0.2×SSC, 0.1% SDS at 65° C. Under these conditions, polynucleotides with higher homology are expected to be obtained efficiently at higher temperatures, although multiple factors are involved in hybridization stringency including temperature, probe concentration, probe length, ionic strength, time, salt concentration and others, and those skilled in the art may appropriately select these factors to achieve similar stringency.

When commercially available kits are used for hybridization, for example, an Alkphos Direct Labeling and Detection System (GE Healthcare) may be used. In this case, according to the attached protocol, after cultivation with a labeled probe overnight, the membrane is washed with a primary wash buffer containing 0.1% (w/v) SDS at 55° C., thereby detecting hybridized polynucleotides. Alternatively, in producing a probe based on the entire or part of the nucleotide sequence complementary to the nucleotide sequence of SEQ ID NO: 1, hybridization can be detected with a DIG Nucleic Acid Detection Kit (Roche Diagnostics) when the probe is labeled with digoxigenin (DIG) using a commercially available reagent (e.g., a PCR Labeling Mix (Roche Diagnostics), etc.).

In addition to the polynucleotides described above, other polynucleotides that can be hybridized include polynucleotides having 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity with the polynucleotide of SEQ ID NO: 1, as calculated by homology search software BLAST using the default parameters.

The identity between nucleotide sequences may be determined using algorithm BLAST (Basic Local Alignment Search Tool) by Karlin and Altschul (Proc. Natl. Acad. Sci. USA 872264-2268, 1990; Proc. Natl. Acad. Sci. USA 90: 5873, 1993). Programs called BLASTN and BLASTX based on the BLAST algorithm have been developed (Altschul S F, et al: J. Mol. Biol. 215: 403, 1990). When a nucleotide sequence is sequenced using BLASTN, the parameters are, for example, score=100 and wordlength=12. When BLAST and Gapped BLAST programs are used, the default parameters for each program are employed.

Examples of the nucleotide sequences complementary to the sequences consisting of the 31st to the 53rd, the 31st to the 54th, the 31st to the 55th, the 31st to the 56th, the 31st to the 57th, the 31st to the 58th, the 32nd to the 53rd, the 32nd to the 54th, the 32nd to the 55th, the 32nd to the 56th, the 32nd to the 57th, the 32nd to the 58th, the 33rd to the 53rd, the 33rd to the 54th, the 33rd to the 55th, the 33rd to the 56th, the 33rd to the 57th, the 33rd to the 58th, the 34th to the 53rd, the 34th to the 54th, the 34th to the 55th, the 34th to the 56th, the 34th to the 57th, the 34th to the 58th, the 35th to the 53rd, the 35th to the 54th, the 35th to the 55th, the 35th to the 56th, the 35th to the 57th, the 35th to the 58th, the 36th to the 53rd, the 36th to the 54th, the 36th to the 55th, the 36th to the 56th, the 36th to the 57th and the 36th to the 58th nucleotides, from the 5' end of exon 53.

TABLE 1

| Target sequence in exon 53 | Complementary nucleotide sequence | SEQ ID NO: |
|---|---|---|
| 31-53 | 5'-CCGGTTCTGAAGGT GTTCTTGTA-3' | SEQ ID NO: 2 |
| 31-54 | 5'-TCCGGTTCTGAAGG TGTTCTTGTA-3' | SEQ ID NO: 3 |
| 31-55 | 5'-CTCCGGTTCTGAAG GTGTTCTTGTA-3' | SEQ ID NO: 4 |
| 31-56 | 5'-CCTCCGGTTCTGAA GGTGTTCTTGTA-3' | SEQ ID NO: 5 |
| 31-57 | 5'-GCCTCCGGTTCTGA AGGTGTTCTTGTA-3' | SEQ ID NO: 6 |
| 31-58 | 5'-TGCCTCCGGTTCTG AAGGTGTTCTTGTA-3' | SEQ ID NO: 7 |
| 32-53 | 5'-CCGGTTCTGAAGGT GTTCTTGT-3' | SEQ ID NO: 8 |
| 32-54 | 5'-TCCGGTTCTGAAGG TGTTCTTGT-3' | SEQ ID NO: 9 |
| 32-55 | 5'-CTCCGGTTCTGAAG GTGTTCTTGT-3' | SEQ ID NO: 10 |
| 32-56 | 5'-CCTCCGGTTCTGAA GGTGTTCTTGT-3' | SEQ ID NO: 11 |
| 32-57 | 5'-GCCTCCGGTTCTGA AGGTGTTCTTGT-3' | SEQ ID NO: 12 |
| 32-58 | 5'-TGCCTCCGGTTCTG AAGGTGTTCTTGT-3' | SEQ ID NO: 13 |

TABLE 1-continued

| Target sequence in exon 53 | Complementary nucleotide sequence | SEQ ID NO: |
|---|---|---|
| 33-53 | 5'-CCGGTTCTGAAGGT GTTCTTG-3' | SEQ ID NO: 14 |
| 33-54 | 5'-TCCGGTTCTGAAGG TGTTCTTG-3' | SEQ ID NO: 15 |
| 33-55 | 5'-CTCCGGTTCTGAAG GTGTTCTTG-3' | SEQ ID NO: 16 |
| 33-56 | 5'-CCTCCGGTTCTGAA GGTGTTCTTG-3' | SEQ ID NO: 17 |
| 33-57 | 5'-GCCTCCGGTTCTGA AGGTGTTCTTG-3' | SEQ ID NO: 18 |
| 33-58 | 5'-TGCCTCCGGTTCTG AAGGTGTTCTTG-3' | SEQ ID NO: 19 |
| 34-53 | 5'-CCGGTTCTGAAGGT GTTCTT-3' | SEQ ID NO: 20 |
| 34-54 | 5'-TCCGGTTCTGAAGG TGTTCTT-3' | SEQ ID NO: 21 |
| 34-55 | 5'-CTCCGGTTCTGAAG GTGTTCTT-3' | SEQ ID NO: 22 |
| 34-56 | 5'-CCTCCGGTTCTGAA GGTGTTTCTT-3' | SEQ ID NO: 23 |
| 34-57 | 5'-GCCTCCGGTTCTGA AGGTGTTCTT-3' | SEQ ID NO: 24 |
| 34-58 | 5'-TGCCTCCGGTTCTG AAGGTGTTCTT-3' | SEQ ID NO: 25 |
| 35-53 | 5'-CCGGTTCTGAAGGT GTTCT-3' | SEQ ID NO: 26 |
| 35-54 | 5'-TCCGGTTCTGAAGG TGTTCT-3' | SEQ ID NO: 27 |
| 35-55 | 5'-CTCCGGTTCTGAAG GTGTTCT-3' | SEQ ID NO: 28 |
| 35-56 | 5'-CCTCCGGTTCTGAA GGTGTTCT-3' | SEQ ID NO: 29 |
| 35-57 | 5'-GCCTCCGGTTCTGA AGGTGTTCT-3' | SEQ ID NO: 30 |
| 35-58 | 5'-TGCCTCCGGTTCTG AAGGTGTTCT-3' | SEQ ID NO: 31 |
| 36-53 | 5'-CCGGTTCTGAAGGT GTTC-3' | SEQ ID NO: 32 |
| 36-54 | 5'-TCCGGTTCTGAAGG TGTTC-3' | SEQ ID NO: 33 |
| 36-55 | 5'-CTCCGGTTCTGAAG GTGTTC-3' | SEQ ID NO: 34 |
| 36-56 | 5'-CCTCCGGTTCTGAA GGTGTTC-3' | SEQ ID NO: 35 |
| 36-57 | 5'-GCCTCCGGTTCTGA AGGTGTTC-3' | SEQ ID NO: 36 |
| 36-58 | 5'-TGCCTCCGGTTCTG AAGGTGTTC-3' | SEQ ID NO: 37 |

It is preferred that the oligomer of the present invention consists of a nucleotide sequence complementary to any one of the sequences consisting of the 32nd to the 56th, the 33rd to the 56th, the 34th to the 56th, the 35th to the 56th or the 36th to the 56th nucleotides (e.g., SEQ ID NO: 11, SEQ ID NO: 17, SEQ ID NO: 23, SEQ ID NO: 29 or SEQ ID NO: 35), from the 5' end of the 53rd exon in the human dystrophin gene.

Preferably, the oligomer of the present invention consists of a nucleotide sequence complementary to any one of the sequences consisting of the 32nd to the 56th or the 36th to the 56th nucleotides (e.g., SEQ ID NO: 11 or SEQ ID NO: 35), from the 5' end of the 53rd exon in the human dystrophin gene.

The term "cause skipping of the 53rd exon in the human dystrophin gene" is intended to mean that by binding of the oligomer of the present invention to the site corresponding to exon 53 of the transcript (e.g., pre-mRNA) of the human dystrophin gene, for example, the nucleotide sequence corresponding to the 5' end of exon 54 is spliced at the 3' side of the nucleotide sequence corresponding to the 3' end of exon 51 in DMD patients with deletion of, exon 52 when the transcript undergoes splicing, thus resulting in formation of mature mRNA which is free of codon frame shift.

Accordingly, it is not required for the oligomer of the present invention to have a nucleotide sequence 100% complementary to the target sequence, as far as it causes exon 53 skipping in the human dystrophin gene. The oligomer of the present invention may include, for example, 1 to 3, 1 or 2, or one nucleotide non-complementary to the target sequence.

Herein, the term "binding" described above is intended to mean that when the oligomer of the present invention is mixed with the transcript of human dystrophin gene, both are hybridized under physiological conditions to form a double strand nucleic acid. The term "under physiological conditions" refers to conditions set to mimic the in vivo environment in terms of pH, salt composition and temperature. The conditions are, for example, 25 to 40° C., preferably 37° C., pH 5 to 8, preferably pH 7.4 and 150 mM of sodium chloride concentration.

Whether the skipping of exon 53 in the human dystrophin gene is caused or not can be confirmed by introducing the oligomer of the present invention into a dystrophin expression cell (e.g., human rhabdomyosarcoma cells), amplifying the region surrounding exon 53 of mRNA of the human dystrophin gene from the total RNA of the dystrophin expression cell by RT-PCR and performing nested PCR or sequence analysis on the PCR amplified product.

The skipping efficiency can be determined as follows. The mRNA for the human dystrophin gene is collected from test cells; in the mRNA, the polynucleotide level "A" of the band where exon 53 is skipped and the polynucleotide level "B" of the band where exon 53 is not skipped are measured. Using these measurement values of "A" and "B," the efficiency is calculated by the following equation:

$$\text{Skipping efficiency}(\%) = A/(A+B) \times 100$$

The oligomer of the present invention includes, for example, an oligonucleotide, morpholino oligomer or peptide nucleic acid (PNA), having a length of 18 to 28 nucleotides. The length is preferably from 21 to 25 nucleotides and morpholino oligomers are preferred.

The oligonucleotide described above (hereinafter referred to as "the oligonucleotide of the present invention") is the oligomer of the present invention composed of nucleotides as constituent units. Such nucleotides may be any of ribonucleotides, deoxyribonucleotides and modified nucleotides.

The modified nucleotide refers to one having fully or partly modified nucleobases, sugar moieties and/or phosphate-binding regions, which constitute the ribonucleotide or deoxyribonucleotide.

The nucleobase includes, for example, adenine, guanine, hypoxanthine, cytosine, thymine, uracil, and modified bases thereof. Examples of such modified nucleobases include, but not limited to, pseudouracil, 3-methyluracil, dihydrouracil, 5-alkylcytosines (e.g., 5-methylcytosine), 5-alkyluracils (e.g., 5-ethyluracil), 5-halouracils (5-bromouracil), 6-azapyrimidine, 6-alkylpyrimidines (6-methyluracil), 2-thiouracil, 4-thiouracil, 4-acetylcytosine, 5-(carboxyhydroxymethyl) uracil, 5'-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, N6-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-N6-isopentenyladenine, uracil-5-oxyacetic acid, 2-thiocytosine, purine, 2,6-diaminopurine, 2-aminopurine, isoguanine, indole, imidazole, xanthine, etc.

Modification of the sugar moiety may include, for example, modifications at the 2'-position of ribose and modifications of the other positions of the sugar. The modification at the 2'-position of ribose includes replacement of the 2'-OH of ribose with OR, R, R'OR, SH, SR, NH$_2$, NHR, NR$_2$, N$_3$, CN, F, Cl, Br or I, wherein R represents an alkyl or an aryl and R' represents an alkylene.

The modification for the other positions of the sugar includes, for example, replacement of O at the 4' position of ribose or deoxyribose with S, bridging between 2' and 4' positions of the sugar, e.g., LNA (locked nucleic acid) or ENA (2'-O,4'-C-ethylene-bridged nucleic acids), but is not limited thereto.

A modification of the phosphate-binding region includes, for example, a modification of replacing phosphodiester bond with phosphorothioate bond, phosphorodithioate bond, alkyl phosphonate bond, phosphoroamidate bond or boranophosphate bond (Enya et al: Bioorganic & Medicinal Chemistry, 2008, 18, 9154-9160) (cf., e.g., Japan Domestic Re-Publications of PCT Application Nos. 2006/129594 and 2006/038608).

The alkyl is preferably a straight or branched alkyl having 1 to 6 carbon atoms. Specific examples include methyl, ethyl, n-propyl, isopropyl, n-butyl, isobutyl, sec-butyl, tert-butyl, n-pentyl, isopentyl, neopentyl, tert-pentyl, n-hexyl and isohexyl. The alkyl may optionally be substituted. Examples of such substituents are a halogen, an alkoxy, cyano and nitro. The alkyl may be substituted with 1 to 3 substituents.

The cycloalkyl is preferably a cycloalkyl having 5 to 12 carbon atoms. Specific examples include cyclopentyl, cyclohexyl, cycloheptyl, cyclooctyl, cyclodecyl and cyclododecyl.

The halogen includes fluorine, chlorine, bromine and iodine.

The alkoxy is a straight or branched alkoxy having 1 to 6 carbon atoms such as methoxy, ethoxy, n-propoxy, isopropoxy, n-butoxy, isobutoxy, sec-butoxy, tert-butoxy, n-pentyloxy, isopentyloxy, n-hexyloxy, isohexyloxy, etc. Among others, an alkoxy having 1 to 3 carbon atoms is preferred.

The aryl is preferably an aryl having 6 to 10 carbon atoms. Specific examples include phenyl, α-naphthyl and β-naphthyl. Among others, phenyl is preferred. The aryl may optionally be substituted. Examples of such substituents are an alkyl, a halogen, an alkoxy, cyano and nitro. The aryl may be substituted with one to three of such substituents.

The alkylene is preferably a straight or branched alkylene having 1 to 6 carbon atoms. Specific examples include methylene, ethylene, trimethylene, tetramethylene, pentamethylene, hexamethylene, 2-(ethyl) trimethylene and 1-(methyl) tetramethylene.

The acyl includes a straight or branched alkanoyl or aroyl. Examples of the alkanoyl include formyl, acetyl, 2-methylacetyl, 2,2-dimethylacetyl, propionyl, butyryl, isobutyryl, pentanoyl, 2,2-dimethylpropionyl, hexanoyl, etc. Examples of the aroyl include benzoyl, toluoyl and naphthoyl. The aroyl may optionally be substituted at substitutable positions and may be substituted with an alkyl(s).

Preferably, the oligonucleotide of the present invention is the oligomer of the present invention containing a constituent unit represented by general formula below wherein the —OH group at position 2' of ribose is substituted with methoxy and the phosphate-binding region is a phosphorothioate bond:

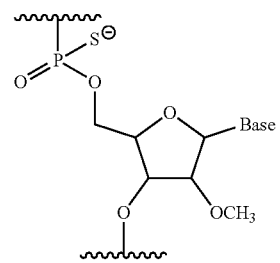

wherein Base represents a nucleobase.

The oligonucleotide of the present invention may be easily synthesized using various automated synthesizer (e.g., AKTA oligopilot plus 10/100 (GE Healthcare)). Alternatively, the synthesis may also be entrusted to a third-party organization (e.g., Promega Inc., or Takara Co.), etc.

The morpholino oligomer of the present invention is the oligomer of the present invention comprising the constituent unit represented by general formula below:

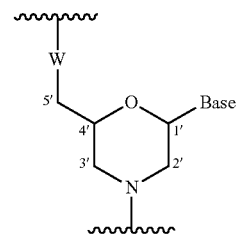

wherein Base has the same significance as defined above, and,
W represents a group shown by any one of the following groups:

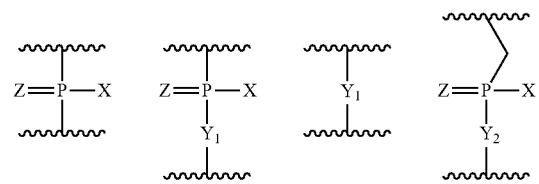

wherein X represents —CH$_2$R$^1$, —O—CH$_2$R$^1$, —S—CH$_2$R$^1$, —NR$_2$R$^3$ or F;

R$^1$ represents H or an alkyl;

R$^2$ and R$^3$, which may be the same or different, each represents H, an alkyl, a cycloalkyl or an aryl;

Y$_1$ represents O, S, CH$_2$ or NR$^1$;

Y$_2$ represents O, S or NR$^1$;

Z represents O or S.

Preferably, the morpholino oligomer is an oligomer comprising a constituent unit represented by general formula below (phosphorodiamidate morpholino oligomer (hereinafter referred to as "PMO")).

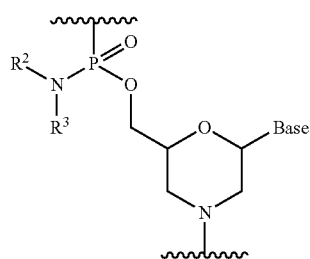

wherein Base, R$^2$ and R$^3$ have the same significance as defined above.

The morpholino oligomer may be produced in accordance with, e.g., WO 1991/009033 or WO 2009/064471. In particular, PMO can be produced by the procedure described in WO 2009/064471 or produced by the process shown below.

[Method for Producing PMO]

An embodiment of PMO is, for example, the compound represented by general formula (I) below (hereinafter PMO (I)).

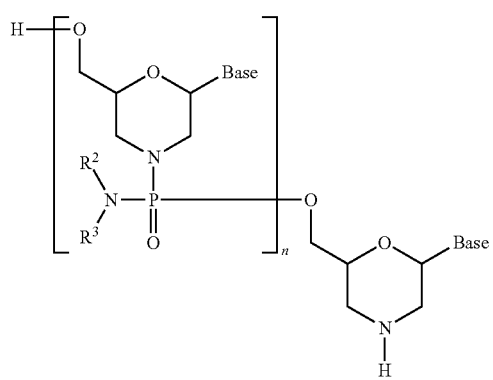

(I)

wherein Base, R$^2$ and R$^3$ have the same significance as defined above; and, n is a given integer of 1 to 99, preferably a given integer of 18 to 28.

PMO (I) can be produced in accordance with a known method, for example, can be produced by performing the procedures in the following steps.

The compounds and reagents used in the steps below are not particularly limited so long as they are commonly used to prepare PMO.

Also, the following steps can all be carried out by the liquid phase method or the solid phase method (using manuals or commercially available solid phase automated synthesizers). In producing PMO by the solid phase method, it is desired to use automated synthesizers in view of simple operation procedures and accurate synthesis.

(1) Step A:

The compound represented by general formula (II) below (hereinafter referred to as Compound (II)) is reacted with an acid to prepare the compound represented by general formula (III) below (hereinafter referred to as Compound (III)):

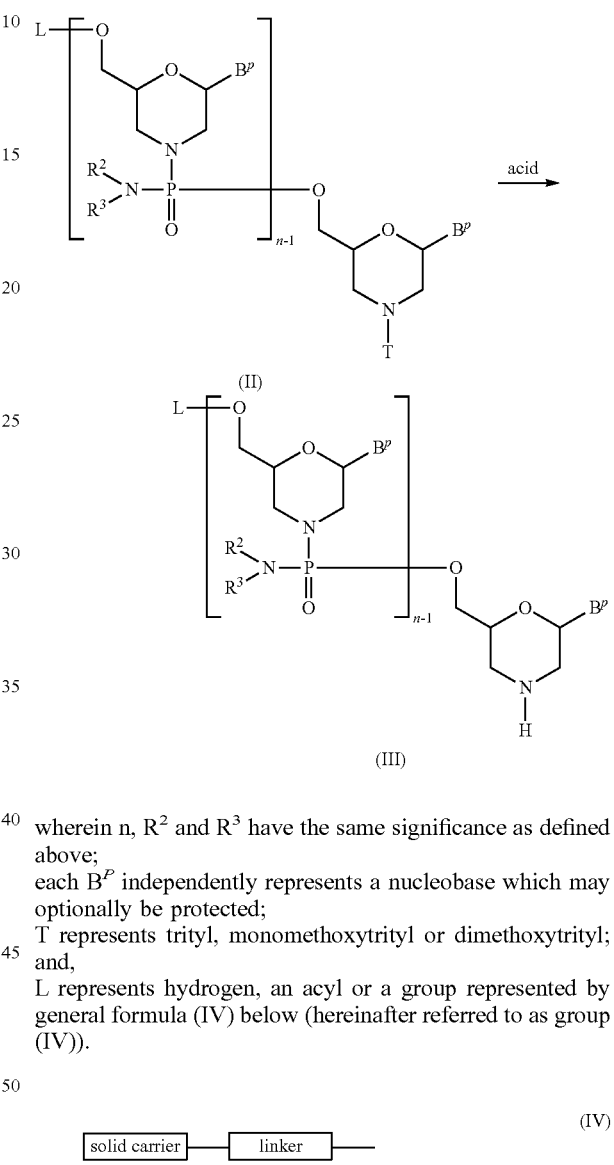

wherein n, R$^2$ and R$^3$ have the same significance as defined above;

each B$^P$ independently represents a nucleobase which may optionally be protected;

T represents trityl, monomethoxytrityl or dimethoxytrityl; and,

L represents hydrogen, an acyl or a group represented by general formula (IV) below (hereinafter referred to as group (IV)).

(IV)

The "nucleobase" for B$^P$ includes the same "nucleobase" as in Base, provided that the amino or hydroxy group in the nucleobase shown by B$^P$ may be protected.

Such protective group for amino is not particularly limited so long as it is used as a protective group for nucleic acids. Specific examples include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene. Specific examples of the protective group for the hydroxy group include 2-cyanoethyl, 4-nitrophenethyl, phenylsulfonylethyl, methylsulfonylethyl and trimethylsilylethyl, and phenyl, which may be substituted by 1 to 5 electron-withdrawing group at optional substitutable positions, diphenylcarbamoyl, dimethylcarbamoyl, diethylcarbamoyl, methylphenylcarbamoyl, 1-pyrolidinylcarbamoyl, morpholinocarbamoyl, 4-(tert-butylcarboxy) benzyl, 4-[(dimethylamino)carboxy]benzyl and 4-(phenylcarboxy)benzyl, (cf., e.g., WO 2009/064471).

The "solid carrier" is not particularly limited so long as it is a carrier usable for the solid phase reaction of nucleic acids. It is desired for the solid carrier to have the following properties: e.g., (i) it is sparingly soluble in reagents that can be used for the synthesis of morpholino nucleic acid derivatives (e.g., dichloromethane, acetonitrile, tetrazole, N-methylimidazole, pyridine, acetic anhydride, lutidine, trifluoroacetic acid); (ii) it is chemically stable to the reagents usable for the synthesis of morpholino nucleic acid derivatives; (iii) it can be chemically modified; (iv) it can be charged with desired morpholino nucleic acid derivatives; (v) it has a strength sufficient to withstand high pressure through treatments; and (vi) it has a uniform particle diameter range and distribution. Specifically, swellable polystyrene (e.g., aminomethyl polystyrene resin 1% dibenzylbenzene crosslinked (200-400 mesh) (2.4-3.0 mmol/g) (manufactured by Tokyo Chemical Industry), Aminomethylated Polystyrene Resin.HCl [dibenzylbenzene 1%, 100-200 mesh] (manufactured by Peptide Institute, Inc.)), non-swellable polystyrene (e.g., Primer Support (manufactured by GE Healthcare)), PEG chain-attached polystyrene (e.g., $NH_2$-PEG resin (manufactured by Watanabe Chemical Co.), TentaGel resin), controlled pore glass (controlled pore glass; CPG) (manufactured by, e.g., CPG), oxalyl-controlled pore glass (cf., e.g., Alul et al., Nucleic Acids Research, Vol. 19, 1527 (1991)), TentaGel support-aminopolyethylene glycol-derivatized support (e.g., Wright et al., cf., Tetrahedron Letters, Vol. 34, 3373 (1993)), and a copolymer of Poros-polystyrene/divinylbenzene.

A "linker" which can be used is a known linker generally used to connect nucleic acids or morpholino nucleic acid derivatives. Examples include 3-aminopropyl, succinyl, 2,2'-diethanolsulfonyl and a long chain alkyl amino (LCAA).

This step can be performed by reacting Compound (11) with an acid.

The "acid" which can be used in this step includes, for example, trifluoroacetic acid, dichloroacetic acid and trichloroacetic acid. The acid used is appropriately in a range of, for example, 0.1 mol equivalent to 1000 mol equivalents based on 1 mol of Compound (II), preferably in a range of 1 mol equivalent to 100 mol equivalents based on 1 mol of Compound (II).

An organic amine can be used in combination with the acid described above. The organic amine is not particularly limited and includes, for example, triethylamine. The amount of the organic amine used is appropriately in a range of, e.g., 0.01 mol equivalent to 10 mol equivalents, and preferably in a range of 0.1 mol equivalent to 2 mol equivalents, based on 1 mol of the acid.

When a salt or mixture of the acid and the organic amine is used in this step, the salt or mixture includes, for example, a salt or mixture of trifluoroacetic acid and triethylamine, and more specifically, a mixture of 1 equivalent of triethylamine and 2 equivalents of trifluoroacetic acid.

The acid which can be used in this step may also be used in the form of a dilution with an appropriate solvent in a concentration of 0.1% to 30%. The solvent is not particularly limited as far as it is inert to the reaction, and includes, for example, dichloromethane, acetonitrile, an alcohol (ethanol, isopropanol, trifluoroethanol, etc.), water, or a mixture thereof.

The reaction temperature in the reaction described above is preferably in a range of, e.g., 10° C. to 50° C., more preferably, in a range of 20° C. to 40° C., and most preferably, in a range of 25° C. to 35° C.

The reaction time may vary depending upon kind of the acid used and reaction temperature, and is appropriately in a range of 0.1 minute to 24 hours in general, and preferably in a range of 1 minute to 5 hours.

After completion of this step, a base may be added, if necessary, to neutralize the acid remained in the system. The "base" is not particularly limited and includes, for example, diisopropylamine. The base may also be used in the form of a dilution with an appropriate solvent in a concentration of 0.1% (v/v) to 30% (v/v).

The solvent used in this step is not particularly limited so long as it is inert to the reaction, and includes dichloromethane, acetonitrile, an alcohol (ethanol, isopropanol, trifluoroethanol, etc.), water, and a mixture thereof. The reaction temperature is preferably in a range of, e.g., 10° C. to 50° C., more preferably, in a range of 20° C. to 40° C., and most preferably, in a range of 25° C. to 35° C.

The reaction time may vary depending upon kind of the base used and reaction temperature, and is appropriately in a range of 0.1 minute to 24 hours in general, and preferably in a range of 1 minute to 5 hours.

In Compound (II), the compound of general formula (IIa) below (hereinafter Compound (IIa)), wherein n is 1 and L is a group (IV), can be produced by the following procedure.

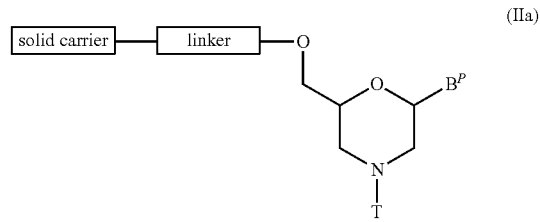

(IIa)

wherein $B^P$, T, linker and solid carrier have the same significance as defined above.

Step 1:

The compound represented by general formula (V) below is reacted with an acylating agent to prepare the compound represented by general formula (VI) below (hereinafter referred to as Compound (VI)).

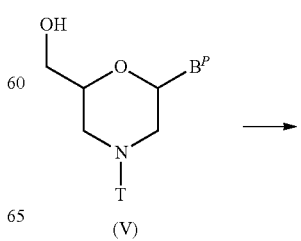

(V)

-continued

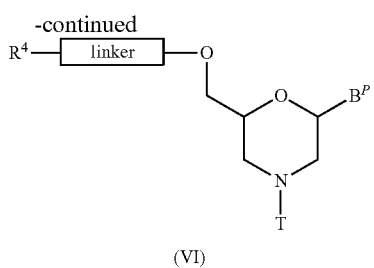

(VI)

wherein $B^P$, T and linker have the same significance as defined above; and,
$R^4$ represents hydroxy, a halogen or amino.

This step can be carried out by known procedures for introducing linkers, using Compound (V) as the starting material.

In particular, the compound represented by general formula (VIa) below can be produced by performing the method known as esterification, using Compound (V) and succinic anhydride.

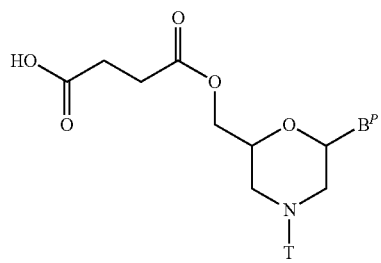

(VIa)

wherein $B^P$ and T have the same significance as defined above.

Step 2:

Compound (VI) is reacted with a solid career by a condensing agent to prepare Compound (IIa).

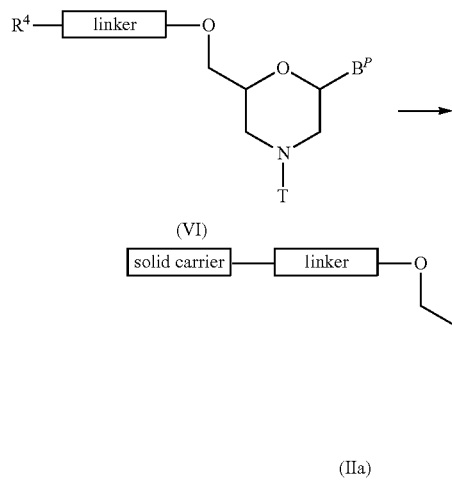

(IIa)

wherein $B^P$, $R^4$, T, linker and solid carrier have the same significance as defined above.

This step can be performed using Compound (VI) and a solid carrier in accordance with a process known as condensation reaction.

In Compound (II), the compound represented by general formula (IIa2) below wherein n is 2 to 99 and L is a group represented by general formula (IV) can be produced by using Compound (IIa) as the starting material and repeating step A and step B of the PMO production method described in the specification for a desired number of times.

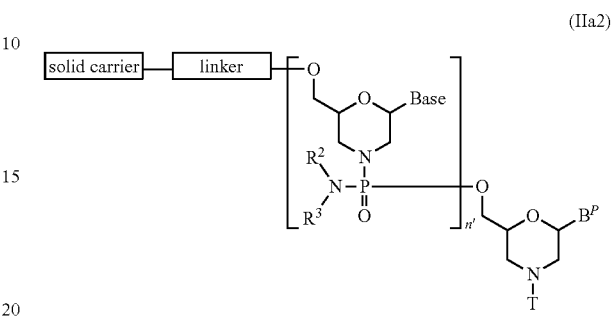

(IIa2)

wherein $B^P$, $R^2$, $R^3$, T, linker and solid carrier have the same significance as defined above; and,
n' represents 1 to 98.

In Compound (II), the compound of general formula (IIb) below wherein n is 1 and L is hydrogen can be produced by the procedure described in, e.g., WO 1991/009033.

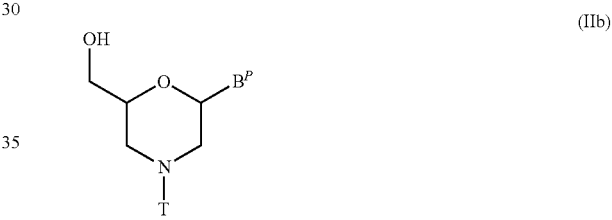

(IIb)

wherein $B^P$ and T have the same significance as defined above.

In Compound (II), the compound represented by general formula (IIb2) below wherein n is 2 to 99 and L is hydrogen can be produced by using Compound (IIb) as the starting material and repeating step A and step B of the PMO production method described in the specification for a desired number of times.

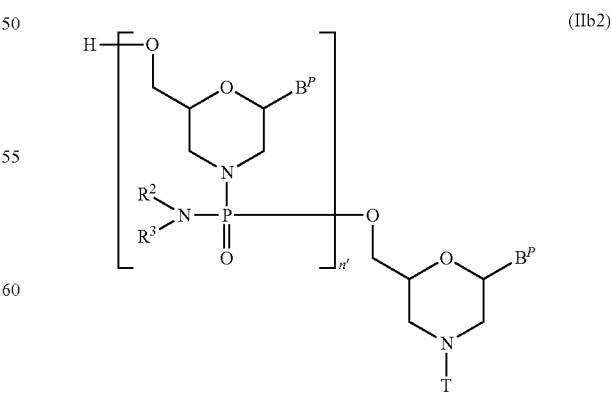

(IIb2)

wherein $B^P$, n', $R^2$, $R^3$ and T have the same significance as defined above.

In Compound (II), the compound represented by general formula (IIc) below wherein n is 1 and L is an acyl can be produced by performing the procedure known as acylation reaction, using Compound (IIb).

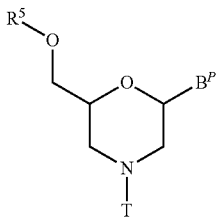

(IIc)

wherein $B^P$ and T have the same significance as defined above; and,
$R^5$ represents an acyl.

In Compound (II), the compound represented by general formula (IIc2) below wherein n is 2 to 99 and L is an acyl can be produced by using Compound (IIc) as the starting material and repeating step A and step B of the PMO production method described in the specification for a desired number of times.

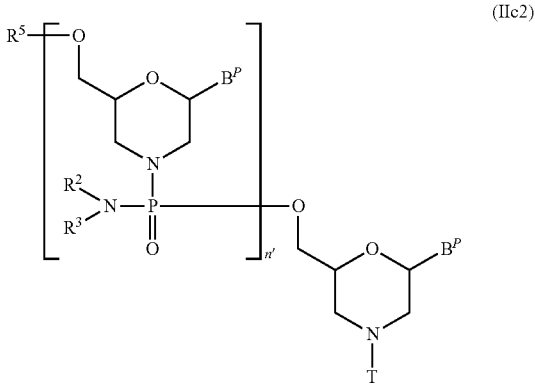

(IIc2)

wherein $B^P$, n', $R^2$, $R^3$, $R^5$ and T have the same significance as defined above.

(2) Step B

Compound (III) is reacted with a morpholino monomer compound in the presence of a base to prepare the compound represented by general formula (VII) below (hereinafter referred to as Compound (VII)):

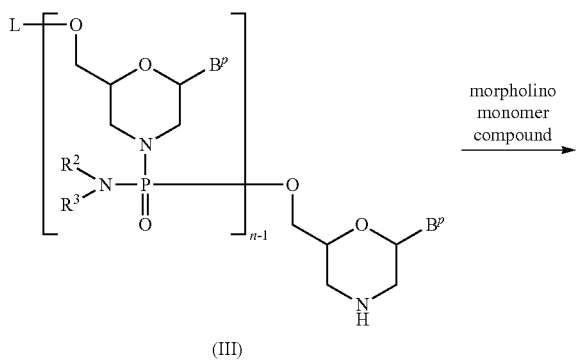

(III)

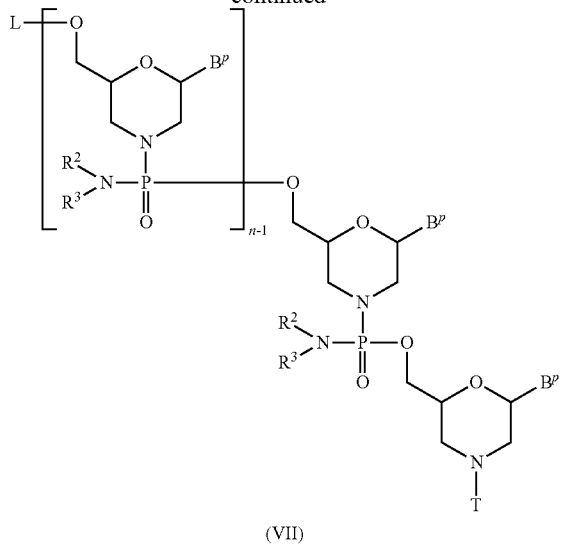

(VII)

wherein $B^P$, L, n, $R^2$, $R^3$ and T have the same significance as defined above.

This step can be performed by reacting Compound (III) with the morpholino monomer compound in the presence of a base.

The morpholino monomer compound includes, for example, compounds represented by general formula (VIII) below:

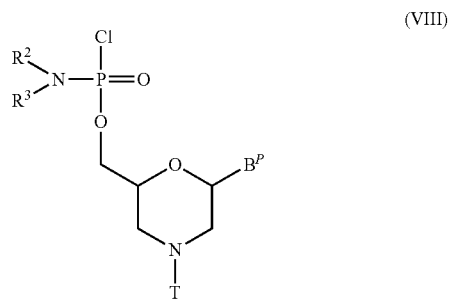

(VIII)

wherein $B^P$, $R^2$, $R^3$ and T have the same significance as defined above.

The "base" which can be used in this step includes, for example, diisopropylamine, triethylamine and N-ethylmorpholine. The amount of the base used is appropriately in a range of 1 mol equivalent to 1000 mol equivalents based on 1 mol of Compound (III), preferably, 10 mol equivalents to 100 mol equivalents based on 1 mol of Compound (III).

The morpholino monomer compound and base which can be used in this step may also be used as a dilution with an appropriate solvent in a concentration of 0.1% to 30%. The solvent is not particularly limited as far as it is inert to the reaction, and includes, for example, N,N-dimethylimidazolidone, N-methylpiperidone, DMF, dichloromethane, acetonitrile, tetrahydrofuran, or a mixture thereof.

The reaction temperature is preferably in a range of, e.g., 0° C. to 100° C., and more preferably, in a range of 10° C. to 50° C.

The reaction time may vary depending upon kind of the base used and reaction temperature, and is appropriately in a range of 1 minute to 48 hours in general, and preferably in a range of 30 minutes to 24 hours.

Furthermore, after completion of this step, an acylating agent can be added, if necessary. The "acylating agent" includes, for example, acetic anhydride, acetyl chloride and phenoxyacetic anhydride. The acylating agent may also be used as a dilution with an appropriate solvent in a concentration of 0.1% to 30%. The solvent is not particularly limited as far as it is inert to the reaction, and includes, for example, dichloromethane, acetonitrile, an alcohol(s) (ethanol, isopropanol, trifluoroethanol, etc.), water, or a mixture thereof.

If necessary, a base such as pyridine, lutidine, collidine, triethylamine, diisopropylethylamine, N-ethylmorpholine, etc. may also be used in combination with the acylating agent. The amount of the acylating agent is appropriately in a range of 0.1 mol equivalent to 10000 mol equivalents, and preferably in a range of 1 mol equivalent to 1000 mol equivalents. The amount of the base is appropriately in a range of, e.g., 0.1 mol equivalent to 100 mol equivalents, and preferably in a range of 1 mol equivalent to 10 mol equivalents, based on 1 mol of the acylating agent.

The reaction temperature in this reaction is preferably in a range of 10° C. to 50° C., more preferably, in a range of 10° C. to 50° C., much more preferably, in a range of 20° C. to 40° C., and most preferably, in a range of 25° C. to 35° C. The reaction time may vary depending upon kind of the acylating agent used and reaction temperature, and is appropriately in a range of 0.1 minute to 24 hours in general, and preferably in a range of 1 minute to 5 hours.

(3) Step C:

In Compound (VII) produced in Step B, the protective group is removed using a deprotecting agent to prepare the compound represented by general formula (IX).

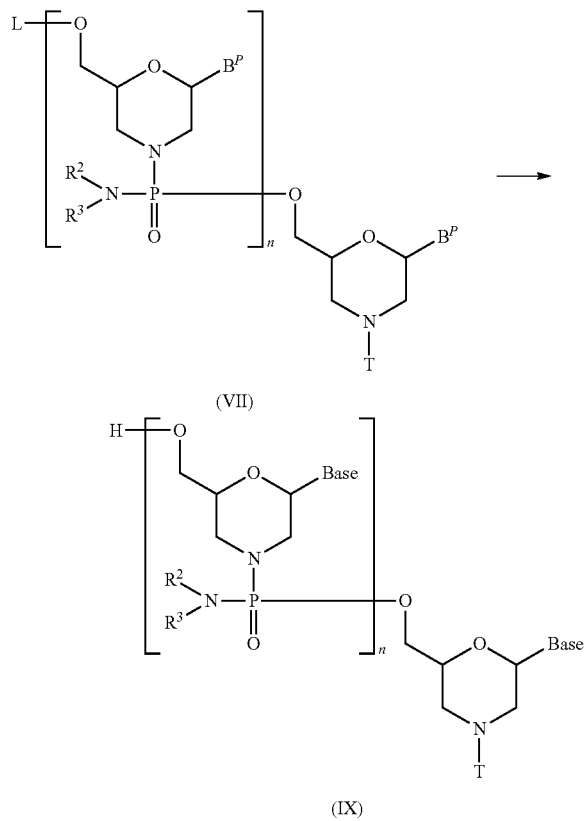

(IX)

wherein Base, $B^P$, L, n, $R^2$, $R^3$ and T have the same significance as defined above.

This step can be performed by reacting Compound (VII) with a deprotecting agent.

The "deprotecting agent" includes, e.g., conc. ammonia water and methylamine. The "deprotecting agent" used in this step may also be used as a dilution with, e.g., water, methanol, ethanol, isopropyl alcohol, acetonitrile, tetrahydrofuran, DMF, N,N-dimethylimidazolidone, N-methylpiperidone, or a mixture of these solvents. Among others, ethanol is preferred. The amount of the deprotecting agent used is appropriately in a range of, e.g., 1 mol equivalent to 100000 mol equivalents, and preferably in a range of 10 mol equivalents to 1000 mol equivalents, based on 1 mol of Compound (VII).

The reaction temperature is appropriately in a range of 15° C. to 75° C., preferably, in a range of 40° C. to 70° C., and more preferably, in a range of 50° C. to 60° C. The reaction time for deprotection may vary depending upon kind of Compound (VII), reaction temperature, etc., and is appropriately in a range of 10 minutes to 30 hours, preferably 30 minutes to 24 hours, and more preferably in a range of 5 hours to 20 hours.

(4) Step D:

PMO (I) is produced by reacting Compound (IX) produced in step C with an acid:

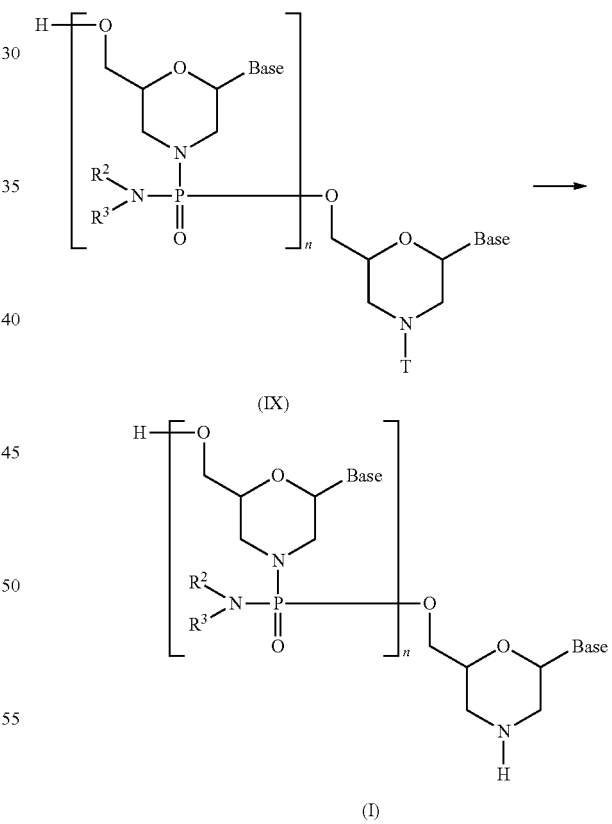

wherein Base, n, $R^2$, $R^3$ and T have the same significance as defined above.

This step can be performed by adding an acid to Compound (IX).

The "acid" which can be used in this step includes, for example, trichloroacetic acid, dichloroacetic acid, acetic acid, phosphoric acid, hydrochloric acid, etc. The acid used is appropriately used to allow the solution to have a pH range of 0.1 to 4.0, and more preferably, in a range of pH 1.0 to 3.0. The solvent is not particularly limited so long as it is inert to the reaction, and includes, for example, acetonitrile, water, or a mixture of these solvents thereof.

The reaction temperature is appropriately in a range of 10° C. to 50° C., preferably, in a range of 20° C. to 40° C., and more preferably, in a range of 25° C. to 35° C. The reaction time for deprotection may vary depending upon kind of Compound (IX), reaction temperature, etc., and is appropriately in a range of 0.1 minute to 5 hours, preferably 1 minute to 1 hour, and more preferably in a range of 1 minute to 30 minutes.

PMO (I) can be obtained by subjecting the reaction mixture obtained in this step to conventional means of separation and purification such as extraction, concentration, neutralization, filtration, centrifugal separation, recrystallization, reversed phase column chromatography $C_8$ to $C_{18}$, cation exchange column chromatography, anion exchange column chromatography, gel filtration column chromatography, high performance liquid chromatography, dialysis, ultrafiltration, etc., alone or in combination thereof. Thus, the desired PMO (I) can be isolated and purified (cf., e.g., WO 1991/09033).

In purification of PMO (I) using reversed phase chromatography, e.g., a solution mixture of 20 mM triethylamine/acetate buffer and acetonitrile can be used as an elution solvent.

In purification of PMO (I) using ion exchange chromatography, e.g., a solution mixture of 1 M saline solution and 10 mM sodium hydroxide aqueous solution can be used as an elution solvent.

A peptide nucleic acid is the oligomer of the present invention having a group represented by the following general formula as the constituent unit:

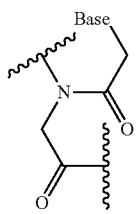

wherein Base has the same significance as defined above.

Peptide nucleic acids can be prepared by referring to, e.g., the following literatures.

1) P. E. Nielsen, M. Egholm, R. H. Berg, I. Buchardt, Science, 254, 1497 (1991)
2) M. Egholm, O. Buchardt, P. E. Nielsen, R. H. Berg, Jacs., 114, 1895 (1992)
3) K. L. Dueholm, M. Egholm, C. Behrens, L. Christensen, H. F. Hansen, T. Vulpius, K. H. Petersen, R. H. Berg, P. E. Nielsen, O. Buchardt, J. Org. Chem., 59, 5767 (1994)
4) L. Christensen, R. Fitzpatrick, B. Gildea, K. H. Petersen, H. E Hansen, T. Koch, M. Egholm, O. Buchardt, P. E. Nielsen, J. Coull, R. H. Berg, J. Pept. Sci., 1, 175 (1995)
5) T. Koch, H. F. Hansen, P. Andersen, T. Larsen, H. G Batz, K. Otteson, H. Orum, J. Pept. Res., 49, 80 (1997)

In the oligomer of the present invention, the 5' end may be any of chemical structures (1) to (3) below, and preferably is (3)-OH.

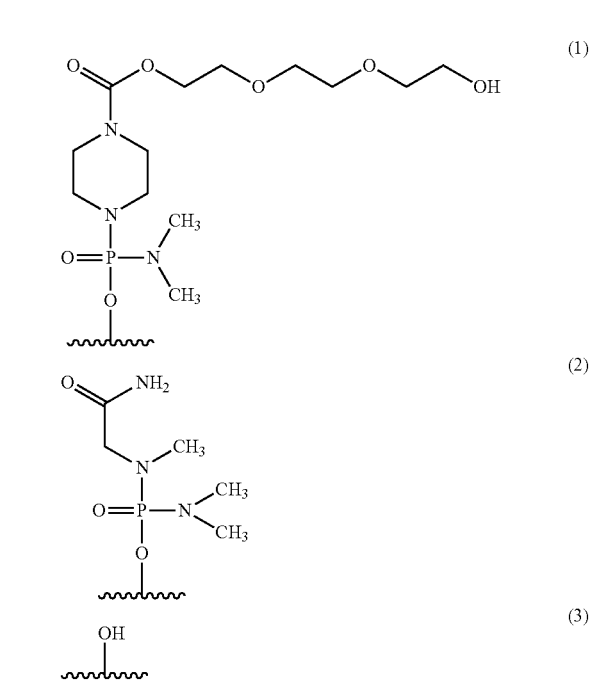

Hereinafter, the groups shown by (1), (2) and (3) above are referred to as "Group (1)," "Group (2)" and "Group (3)," respectively.

2. Pharmaceutical Composition

The oligomer of the present invention causes exon 53 skipping with a higher efficiency as compared to the prior art antisense oligomers. It is thus expected that conditions of muscular dystrophy can be relieved with high efficiency by administering the pharmaceutical composition comprising the oligomer of the present invention to DMD patients. For example, when the pharmaceutical composition comprising the oligomer of the present invention is used, the same therapeutic effects can be achieved even in a smaller dose than that of the oligomers of the prior art. Accordingly, side effects can be alleviated and such is economical.

In another embodiment, the present invention provides the pharmaceutical composition for the treatment of muscular dystrophy, comprising as an active ingredient the oligomer of the present invention, a pharmaceutically acceptable salt or hydrate thereof (hereinafter referred to as "the composition of the present invention").

Examples of the pharmaceutically acceptable salt of the oligomer of the present invention contained in the composition of the present invention are alkali metal salts such as salts of sodium, potassium and lithium; alkaline earth metal salts such as salts of calcium and magnesium; metal salts such as salts of aluminum, iron, zinc, copper, nickel, cobalt, etc.; ammonium salts; organic amine salts such as salts of t-octylamine, dibenzylamine, morpholine, glucosamine, phenylglycine alkyl ester, ethylenediamine, N-methylglucamine, guanidine, diethylamine, triethylamine, dicyclohexylamine, N, N'-dibenzylethylenediamine, chloroprocaine, procaine, diethanolamine, N-benzylphenethylamine, piperazine, tetramethylammonium, tris(hydroxymethyl)aminomethane; hydrohalide salts such as salts of hydrofluorates, hydrochlorides, hydrobromides and hydroiodides; inorganic acid salts such as nitrates, perchlorates, sulfates, phosphates, etc.; lower alkane sulfonates such as methanesulfonates, trifluoromethanesulfonates and ethanesulfonates; arylsulfonates such as benzenesulfonates and p-toluenesulfonates; organic acid salts such as acetates, malates, fumarates, succinates, citrates, tartarates, oxalates, maleates, etc.; and, amino acid salts such as salts of glycine, lysine, arginine, ornithine, glutamic acid and aspartic acid. These salts may be produced by known methods. Alternatively, the oligomer of the present invention contained in the composition of the present invention may be in the form of a hydrate thereof.

Administration route for the composition of the present invention is not particularly limited so long as it is pharmaceutically acceptable route for administration, and can be chosen depending upon method of treatment. In view of easiness in delivery to muscle tissues, preferred are intravenous administration, intraarterial administration, intramuscular administration, subcutaneous administration, oral administration, tissue administration, transdermal administration, etc. Also, dosage forms which are available for the composition of the present invention are not particularly limited, and include, for example, various injections, oral agents, drips, inhalations, ointments, lotions, etc.

In administration of the oligomer of the present invention to patients with muscular dystrophy, the composition of the present invention preferably contains a carrier to promote delivery of the oligomer to muscle tissues. Such a carrier is not particularly limited as far as it is pharmaceutically acceptable, and examples include cationic carriers such as cationic liposomes, cationic polymers, etc., or carriers using viral envelope. The cationic liposomes are, for example, liposomes composed of 2-O-(2-diethylaminoethyl)carabamoyl-1,3-O-dioleoylglycerol and phospholipids as the essential constituents (hereinafter referred to as "liposome A"), Oligofectamine (registered trademark) (manufactured by Invitrogen Corp.), Lipofectin (registered trademark) (manufactured by Invitrogen Corp.), Lipofectamine (registered trademark) (manufactured by Invitrogen Corp.), Lipofectamine 2000 (registered trademark) (manufactured by Invitrogen Corp.), DMRIE-C (registered trademark) (manufactured by Invitrogen Corp.), GeneSilencer (registered trademark) (manufactured by Gene Therapy Systems), TransMessenger (registered trademark) (manufactured by QIAGEN, Inc.), TransIT TKO (registered trademark) (manufactured by Mirus) and Nucleofector II (Lonza). Among others, liposome A is preferred. Examples of cationic polymers are JetSI (registered trademark) (manufactured by Qbiogene, Inc.) and Jet-PEI (registered trademark) (polyethylenimine, manufactured by Qbiogene, Inc.). An example of carriers using viral envelop is GenomeOne (registered trademark) (HVJ-E liposome, manufactured by Ishihara Sangyo). Alternatively, the medical devices described in Japanese Patent No. 2924179 and the cationic carriers described in Japanese Domestic Re-Publication PCT Nos. 2006/129594 and 2008/096690 may be used as well.

A concentration of the oligomer of the present invention contained in the composition of the present invention may vary depending on kind of the carrier, etc., and is appropriately in a range of 0.1 nM to 100 µM, preferably in a range of 1 nM to 10 µM, and more preferably in a range of 10 nM to 1 µM. A weight ratio of the oligomer of the present invention contained in the composition of the present invention and the carrier (carrier/oligomer of the present invention) may vary depending on property of the oligomer, type of the carrier, etc., and is appropriately in a range of 0.1 to 100, preferably in a range of 1 to 50, and more preferably in a range of 10 to 20.

In addition to the oligomer of the present invention and the carrier described above, pharmaceutically acceptable additives may also be optionally formulated in the composition of the present invention. Examples of such additives are emulsification aids (e.g., fatty acids having 6 to 22 carbon atoms and their pharmaceutically acceptable salts, albumin and dextran), stabilizers (e.g., cholesterol and phosphatidic acid), isotonizing agents (e.g., sodium chloride, glucose, maltose, lactose, sucrose, trehalose), and pH controlling agents (e.g., hydrochloric acid, sulfuric acid, phosphoric acid, acetic acid, sodium hydroxide, potassium hydroxide and triethanolamine). One or more of these additives can be used. The content of the additive in the composition of the present invention is appropriately 90 wt % or less, preferably 70 wt % or less and more preferably, 50 wt % or less.

The composition of the present invention can be prepared by adding the oligomer of the present invention to a carrier dispersion and adequately stirring the mixture. Additives may be added at an appropriate step either before or after addition of the oligomer of the present invention. An aqueous solvent that can be used in adding the oligomer of the present invention is not particularly limited as far as it is pharmaceutically acceptable, and examples are injectable water or injectable distilled water, electrolyte fluid such as physiological saline, etc., and sugar fluid such as glucose fluid, maltose fluid, etc. A person skilled in the art can appropriately choose conditions for pH and temperature for such matter.

The composition of the present invention may be prepared into, e.g., a liquid form and its lyophilized preparation. The lyophilized preparation can be prepared by lyophilizing the composition of the present invention in a liquid form in a conventional manner. The lyophilization can be performed, for example, by appropriately sterilizing the composition of the present invention in a liquid form, dispensing an aliquot into a vial container, performing preliminary freezing for 2 hours at conditions of about −40 to −20° C., performing a primary drying at 0 to 10° C. under reduced pressure, and then performing a secondary drying at about 15 to 25° C. under reduced pressure. In general, the lyophilized preparation of the composition of the present invention can be obtained by replacing the content of the vial with nitrogen gas and capping.

The lyophilized preparation of the composition of the present invention can be used in general upon reconstitution by adding an optional suitable solution (reconstitution liquid) and redissolving the preparation. Such a reconstitution liquid includes injectable water, physiological saline and other infusion fluids. A volume of the reconstitution liquid may vary depending on the intended use, etc., is not particularly limited, and is suitably 0.5 to 2-fold greater than the volume prior to lyophilization or no more than 500 mL.

It is desired to control a dose of the composition of the present invention to be administered, by taking the following factors into account: the type and dosage form of the oligomer of the present invention contained; patients' conditions including age, body weight, etc.; administration route; and the characteristics and extent of the disease. A daily dose calculated as the amount of the oligomer of the present invention is generally in a range of 0.1 mg to 10 g/human, and preferably 1 mg to 1 g/human. This numerical range may vary occasionally depending on type of the target disease, administration route and target molecule. Therefore, a dose lower than the range may be sufficient in some occasion and conversely, a dose higher than the range may be required occasionally. The composition can be administered from once to several times daily or at intervals from one day to several days.

In still another embodiment of the composition of the present invention, there is provided a pharmaceutical composition comprising a vector capable of expressing the oligonucleotide of the present invention and the carrier described above. Such an expression vector may be a vector capable of expressing a plurality of the oligonucleotides of the present invention. The composition may be formulated with pharmaceutically acceptable additives as in the case with the composition of the present invention containing the oligomer of the present invention. A concentration of the expression vector contained in the composition may vary depending upon type of the career, etc., and is appropriately in a range of 0.1 nM to 100 μM, preferably in a range of 1 nM to 10 μM, and more preferably in a range of 10 nM to 1 μM. A weight ratio of the expression vector contained in the composition and the carrier (carrier/expression vector) may vary depending on property of the expression vector, type of the carrier, etc., and is appropriately in a range of 0.1 to 100, preferably in a range of 1 to 50, and more preferably in a range of 10 to 20. The content of the carrier contained in the composition is the same as in the case with the composition of the present invention containing the oligomer of the present invention, and a method for producing the same is also the same as in the case with the composition of the present invention.

Hereinafter, the present invention will be described in more detail with reference to EXAMPLES and TEST EXAMPLES below, but is not deemed to be limited thereto.

EXAMPLES

Reference Example 1

4-{[(2S,6R)-6-(4-Benzamido-2-oxopyrimidin-1-yl)-4-tritylmorpholin-2-yl]methoxy}-4-oxobutanoic Acid Loaded onto Aminomethyl Polystyrene Resin Step 1: Production of 4-{[(2S,6R)-6-(4-benzamido-2-oxopyrimidin-1(2H)-yl)-4-tritylmorpholin-2-yl] meth oxy}-4-oxobutanoic Acid Under argon atmosphere, 22.0 g of N-{1-[(2R,6S)-6-(hydroxymethyl)-4-tritylmorpholin-2-yl]-2-oxo-1,2-dihydropyrimidin-4-yl}benzamide and 7.04 g of 4-dimethylaninopyridine (4-DMAP) were suspended in 269 mL of dichloromethane, and 5.76 g of succinic anhydride was added to the suspension, followed by stirring at room temperature for 3 hours. To the reaction solution was added 40 mL of methanol, and the mixture was concentrated under reduced pressure. The residue was extracted using ethyl acetate and 0.5M aqueous potassium dihydrogenphosphate solution. The resulting organic layer was washed sequentially with 0.5M aqueous potassium dihydrogenphosphate solution, water and brine in the order mentioned. The resulting organic layer was dried over sodium sulfate and concentrated under reduced pressure to give 25.9 g of the product.

Step 2: Production of 4-{[(2S,6R)-6-(4-benzamido-2-oxopyrimidin-1-yl)-4-tritylmorpholin-2-yl] methoxy}-4-oxobutanoic Acid Loaded onto Aminomethyl Polystyrene Resin After 23.5 g of 4-{[(2S,6R)-6-(4-benzamido-2-oxopyrimidin-1(2H)-yl)-4-tritylmorpholin-2-yl]meth oxy}-4-oxobutanoic acid was dissolved in 336 mL of pyridine (dehydrated), 4.28 g of 4-DMAP and 40.3 g of 1-ethyl-3-(3-dimethylaminopropyl)carbodiimide hydrochloride were added to the solution. Then, 25.0 g of Aminomethyl Polystyrene Resin cross-linked with 1% DVB (manufactured by Tokyo Chemical Industry Co., Ltd., A1543) and 24 mL of triethylamine were added to the mixture, followed by shaking at room temperature for 4 days. After completion of the reaction, the resin was taken out by filtration. The resulting resin was washed sequentially with pyridine, methanol and dichloromethane in the order mentioned, and dried under reduced pressure. To the resulting resin were added 150 mL of tetrahydrofuran (dehydrate), 15 mL of acetic anhydride and 15 mL of 2,6-lutidine, and the mixture was shaken at room temperature for 2 hours. The resin was taken out by filtration, washed sequentially with pyridine, methanol and dichloromethane in the order mentioned, and dried under reduced pressure to give 33.7 g of the product.

The loading amount of the product was determined by measuring UV absorbance at 409 nm of the molar amount of the trityl per g resin using a known method. The loading amount of the resin was 397.4 μmol/g.

Conditions of UV Measurement
  Device: U-2910 (Hitachi, Ltd.)
  Solvent: methanesulfonic acid
  Wavelength: 265 nm
  ε Value: 45000

Reference Example 2

4-Oxo-4-{[(2S,6R)-6-(6-oxo-2-[2-phenoxyacetamido]-1H-purin-9-yl)-4-tritylmorpholin-2-yl] methoxy}butanoic acid loaded onto 2-aminomethylpolystyrene Resin Step 1: Production of $N^2$-(phenoxyacetyl)guanosine Guanosine, 100 g, was dried at 80° C. under reduced pressure for 24 hours. After 500 mL of pyridine (anhydrous) and 500 mL of dichloromethane (anhydrous) were added thereto, 401 mL of chlorotrimethylsilane was dropwise added to the mixture under an argon atmosphere at 0° C., followed by stirring at room temperature for 3 hours. The mixture was again ice-cooled and 66.3 g of phenoxyacetyl chloride was dropwise added thereto. Under ice cooling, the mixture was stirred for further 3 hours. To the reaction solution was added 500 mL of methanol, and the mixture was stirred at room temperature overnight. The solvent was then removed by distillation under reduced pressure. To the residue was added 500 mL of methanol, and concentration under reduced pressure was performed 3 times. To the residue was added 4 L of water, and the mixture was stirred for an hour under ice cooling. The precipitates formed were taken out by filtration, washed sequentially with water and cold methanol and then dried to give 150.2 g of the objective compound (yield: 102%) (cf.:Org. Lett. (2004), Vol. 6, No. 15, 2555-2557).

Step 2: N-{9-[(2R,6S)-6-(hydroxymethyl)-4-morpholin-2-yl]-6-oxo-6,9-dihydro-1H-purin-2-yl}-2-phenoxyacetamide p-toluenesulfonate In 480 mL of methanol was suspended 30 g of the compound obtained in Step 1, and 130 mL of 2N hydrochloric acid was added to the suspension under ice cooling. Subsequently, 56.8 g of ammonium tetraborate tetrahydrate and 16.2 g of sodium periodate were added to the mixture in the order mentioned and stirred at room temperature for 3 hours. The reaction solution was ice cooled and the insoluble matters were removed by filtration, followed by washing with 100 mL of methanol. The filtrate and washing liquid were combined and the mixture was ice cooled. To the mixture was added 11.52 g of 2-picoline borane. After stirring for 20 minutes, 54.6 g of p-toluenesulfonic acid monohydrate was slowly added to the mixture, followed by stirring at 4° C. overnight. The precipitates were taken out by filtration and washed with 500 mL of cold methanol and dried to give 17.7 g of the objective compound (yield: 43.3%).

$^1$H NMR (δ, DMSO-d6): 9.9-9.2 (2H, br), 8.35 (1H, s), 7.55 (2H, m), 7.35 (2H, m), 7.10 (2H, d, J=7.82 Hz), 7.00 (3H, m), 5.95 (1H, dd, J=10.64, 2.42 Hz), 4.85 (2H, s), 4.00 (1H, m), 3.90-3.60 (2H, m), 3.50-3.20 (5H, m), 2.90 (1H, m), 2.25 (3H, s)

Step 3: Production of N-{9-[(2R,6S)-6-(hydroxymethyl)-4-tritylmorpholin-2-yl]-6-oxo-6,9-dihydro-1H-purin-2-yl}-2-phenoxyacetamide In 30 mL of dichloromethane was suspended 2.0 g of the compound obtained in Step 2, and 13.9 g of triethylamine and 18.3 g of trityl chloride were added to the suspension under ice cooling. The mixture was stirred at room temperature for an hour. The reaction solution was washed with saturated sodium bicarbonate aqueous solution and then with water, and dried. The organic layer was concentrated under reduced pressure. To the residue was added 40 mL of 0.2M sodium citrate buffer (pH 3)/methanol (1:4 (v/v)), and the mixture was stirred. Subsequently, 40 mL of water was added and the mixture was stirred for an hour under ice cooling. The mixture was taken out by filtration, washed with cold methanol and dried to give 1.84 g of the objective compound (yield: 82.0%).

Step 4: Production of 4-oxo-4-{[(2S,6R)-6-(6-oxo-2-[2-phenoxyacetamido]-1H-purin-9-yl)-4-tritylmorpholin-2-yl]methoxy}butanoic Acid Loaded onto Aminomethyl Polystyrene Resin The title compound was produced in a manner similar to REFERENCE EXAMPLE 1, except that N-{9-[(2R,6S)-6-(hydroxymethyl)-4-tritylmorpholin-2-yl]-6-oxo-6,9-dihydro-1H-purin-2-yl}-2-phenoxyacetamide was used in this step, instead of N-{1-[(2R,6S)-6-(hydroxymethyl)-4-tritylmorpholin-2-yl]-2-oxo-1,2-dihydropyrimidin-4-yl}benzamide used in Step 1 of REFERENCE EXAMPLE 1.

Reference Example 3

4-{[(2S,6R)-6-(5-Methyl-2,4-dioxo-3,4-dihydropyrimidin-1-yl)-4-tritylmorpholin-2-yl]methoxy}-4-oxobutanoic Acid Loaded onto Aminomethyl Polystyrene Resin The title compound was produced in a manner similar to REFERENCE EXAMPLE 1, except that 1-[(2R,6S)-6-(hydroxymethyl)-4-tritylmorpholin-2-yl]-5-methylpyrimidine-2,4 (1H,3H)-dione was used in this step, instead of N-{1-[(2R,6S)-6-(hydroxymethyl)-4-tritylmorpholin-2-yl]-2-oxo-1,2-dihydropyrimidin-4-yl}benzamide used in Step 1 of REFERENCE EXAMPLE 1.

Reference Example 4

1,12-Dioxo-1-(4-tritylpiperazin-1-yl)-2,5,8,11-tetraoxa-15-pentadecanoic Acid Loaded onto Aminomethyl Polystyrene Resin The title compound was produced in a manner similar to REFERENCE EXAMPLE 1, except that 2-[2-(2-hydroxyethoxy)ethoxy]ethyl 4-tritylpiperazine-1-carboxylic acid (the compound described in WO 2009/064471) was used in this step, instead of N-{1-[(2R,6S)-6-(hydroxymethyl)-4-tritylmorpholin-2-yl]-2-oxo-1,2-dihydropyrimidin-4-yl}benzamide.

According to the descriptions in EXAMPLES 1 to 12 and REFERENCE EXAMPLES 1 to 3 below, various types of PMO shown by PMO Nos. 1-11 and 13-16 in TABLE 2 were synthesized. The PMO synthesized was dissolved in injectable water (manufactured by Otsuka Pharmaceutical Factory, Inc.). PMO No. 12 was purchased from Gene Tools, LLC.

TABLE 2

| PMO No. | Target sequence in exon 53 | Note | SEQ ID NO: |
| --- | --- | --- | --- |
| 1 | 31-55 | 5' end: group (3) | SEQ ID NO: 4 |
| 2 | 32-53 | 5' end: group (3) | SEQ ID NO: 8 |
| 3 | 32-56 | 5' end: group (3) | SEQ ID NO: 11 |
| 4 | 33-54 | 5' end: group (3) | SEQ ID NO: 15 |
| 5 | 34-58 | 5' end: group (3) | SEQ ID NO: 25 |
| 6 | 36-53 | 5' end: group (3) | SEQ ID NO: 32 |
| 7 | 36-55 | 5' end: group (3) | SEQ ID NO: 34 |
| 8 | 36-56 | 5' end: group (3) | SEQ ID NO: 35 |
| 9 | 36-57 | 5' end: group (3) | SEQ ID NO: 36 |
| 10 | 33-57 | 5' end: group (3) | SEQ ID NO: 18 |
| 11 | 39-69 | Sequence corresponding to H53A(+39 + 69) (cf. Table 1) in Non-Patent Document 3, 5' end: group (3) | SEQ ID NO: 38 |
| 12 | 30-59 | Sequence corresponding to h53A30/1 (cf. Table 1) in Non-Patent Document 5, 5' end: group (2) | SEQ ID NO: 39 |
| 13 | 32-56 | 5' end: group (1) | SEQ ID NO: 11 |
| 14 | 36-56 | 5' end: group (1) | SEQ ID NO: 35 |
| 15 | 30-59 | Sequence corresponding to h53A30/1 (cf. Table 1) in Non-Patent Document 5 5' end: group (3) | SEQ ID NO: 39 |
| 16 | 23-47 | Sequence corresponding to SEQ ID NO: 429 described in Patent Document 4, 5' end: group (3) | SEQ ID NO: 47 |

Example 1

PMO No. 8

4-{[(2S,6R)-6-(4-Benzamido-2-oxopyrimidin-1(2H)-yl)-4-tritylmorpholin-2-yl]methoxy}-4-oxobutanoic acid, loaded onto aminomethyl polystyrene resin (REFERENCE EXAMPLE 1), 2 g (800 μmop was transferred to a reaction vessel, and 30 mL of dichloromethane was added thereto. The mixture was allowed to stand for 30 minutes. After the mixture was further washed twice with 30 mL of dichloromethane, the following synthesis cycle was started. The desired morpholino monomer compound was added in each cycle to give the nucleotide sequence of the title compound.

TABLE 3

| Step | Reagent | Volume (mL) | Time (min) |
| --- | --- | --- | --- |
| 1 | deblocking solution | 30 | 2.0 |
| 2 | deblocking solution | 30 | 2.0 |
| 3 | deblocking solution | 30 | 2.0 |
| 4 | deblocking solution | 30 | 2.0 |
| 5 | deblocking solution | 30 | 2.0 |
| 6 | deblocking solution | 30 | 2.0 |
| 7 | neutralizing solution | 30 | 1.5 |

TABLE 3-continued

| Step | Reagent | Volume (mL) | Time (min) |
|---|---|---|---|
| 8 | neutralizing solution | 30 | 1.5 |
| 9 | neutralizing solution | 30 | 1.5 |
| 10 | neutralizing solution | 30 | 1.5 |
| 11 | neutralizing solution | 30 | 1.5 |
| 12 | neutralizing solution | 30 | 1.5 |
| 13 | dichloromethane | 30 | 0.5 |
| 14 | dichloromethane | 30 | 0.5 |
| 15 | dichloromethane | 30 | 0.5 |
| 16 | coupling solution B | 20 | 0.5 |
| 17 | coupling solution A | 6-11 | 90.0 |
| 18 | dichloromethane | 30 | 0.5 |
| 19 | dichloromethane | 30 | 0.5 |
| 20 | dichloromethane | 30 | 0.5 |
| 21 | capping solution | 30 | 3.0 |
| 22 | capping solution | 30 | 3.0 |
| 23 | dichloromethane | 30 | 0.5 |
| 24 | dichloromethane | 30 | 0.5 |
| 25 | dichloromethane | 30 | 0.5 |

The deblocking solution used was a solution obtained by dissolving a mixture of trifluoroacetic acid (2 equivalents) and triethylamine (1 equivalent) in a dichloromethane solution containing 1% (v/v) ethanol and 10% (v/v) 2,2,2-trifluoroethanol to be 3% (w/v). The neutralizing solution used was a solution obtained by dissolving N,N-diisopropylethylamine in a dichloromethane solution containing 25% (v/v) 2-propanol to be 5% (v/v). The coupling solution A used was a solution obtained by dissolving the morpholino monomer compound in 1,3-dimethyl-2-imidazolidinone containing 10% (v/v) N,N-diisopropylethylamine to be 0.15M. The coupling solution B used was a solution obtained by dissolving N,N-diisopropylethylamine in 1,3-dimethyl-2-imidazolidinone to be 10% (v/v). The capping solution used was a solution obtained by dissolving 20% (v/v) acetic anhydride and 30% (v/v) 2, 6-lutidine in dichloromethane.

The aminomethyl polystyrene resin loaded with the PMO synthesized above was recovered from the reaction vessel and dried at room temperature for at least 2 hours under reduced pressure. The dried PMO loaded onto aminomethyl polystyrene resin was charged in a reaction vessel, and 200 mL of 28% ammonia water-ethanol (1/4) was added thereto. The mixture was stirred at 55° C. for 15 hours. The aminomethyl polystyrene resin was separated by filtration and washed with 50 mL of water-ethanol (1/4). The resulting filtrate was concentrated under reduced pressure. The resulting residue was dissolved in 100 mL of a solvent mixture of 20 mM acetic acid-triethylamine buffer (TEAA buffer) and acetonitrile (4/1) and filtered through a membrane filter. The filtrate obtained was purified by reversed phase HPLC. The conditions used are as follows.

TABLE 4

| | |
|---|---|
| Column | XTerra MS18 (Waters, φ50× 100 mm, 1CV = 200 mL) |
| Flow rate | 60 mL/min |
| Column temperature | room temperature |
| Solution A | 20 mM TEAA buffer |
| Solution B | $CH_3CN$ |
| Gradient | (B) conc. 20→50%/9CV |

Each fraction was analyzed and the product was recovered in 100 mL of acetonitrile-water (1/1), to which 200 mL of ethanol was added. The mixture was concentrated under reduced pressure. Further drying under reduced pressure gave a white solid. To the resulting solid was added 300 mL of 10 mM phosphoric acid aqueous solution to suspend the solid. To the suspension was added 10 mL of 2M phosphoric acid aqueous solution, and the mixture was stirred for 15 minutes. Furthermore, 15 mL of 2M sodium hydrate aqueous solution was added for neutralization. Then, 15 mL of 2M sodium hydroxide aqueous solution was added to make the mixture alkaline, followed by filtration through a membrane filter (0.45 µm). The mixture was thoroughly washed with 100 mL of 10 mM sodium hydroxide aqueous solution to give the product as an aqueous solution.

The resulting aqueous solution containing the product was purified by an anionic exchange resin column. The conditions used are as follows.

TABLE 5

| | |
|---|---|
| Column | Source 30Q (GE Healthcare, φ40× 150 mm, 1CV = 200 mL) |
| Flow rate | 80 mL/min |
| Column temp. | room temperature |
| Solution A | 10 mM sodium hydroxide aqueous solution |
| Solution B | 10 mM sodium hydroxide aqueous solution, 1M sodium chloride aqueous solution |
| Gradient | (B) conc. 5→35%/15CV |

Each fraction was analyzed (on HPLC) and the product was obtained as an aqueous solution. To the resulting aqueous solution was added 225 mL of 0.1M phosphate buffer (pH 6.0) for neutralization. The mixture was filtered through a membrane filter (0.45 µm). Next, ultrafiltration was performed under the conditions described below.

TABLE 6

| | |
|---|---|
| Filter | PELLICON2 MINI FILTER PLBC 3K Regenerated Cellulose, Screen Type C |
| Size | 0.1 m² |

The filtrate was concentrated to give approximately 250 mL of an aqueous solution. The resulting aqueous solution was filtered through a membrane filter (0.45 µm). The aqueous solution obtained was freeze-dried to give 1.5 g of the objective compound as a white cotton-like solid.

ESI-TOF-MS Calcd.: 6924.82.

Found: 6923.54.

Example 2

PMO. No. 1

The title compound was produced in accordance with the procedure of EXAMPLE 1.

MALDI-TOF-MS Calcd.: 8291.96.

Found: 8296.24.

Example 3

PMO. No. 2

The title compound was produced in accordance with the procedure of EXAMPLE 1.

ESI-TOF-MS Calcd.: 7310.13.

Found: 7309.23.

Example 4

PMO. No. 3

The title compound was produced in accordance with the procedure of EXAMPLE 1.

ESI-TOF-MS Calcd.: 8270.94.

Found: 8270.55.

Example 5

PMO. No. 4

The title compound was produced in accordance with the procedure of EXAMPLE 1, except that 4-(((2S,6R)-6-(5-methyl-2,4-dioxo-3,4-dihydropyrimidin-1(2H)-yl)-4-tritylmorpholin-2-yl)methoxy)-4-oxobutanoic acid (REFERENCE EXAMPLE 3) loaded onto aminomethyl polystyrene resin was used as the starting material.

ESI-TOF-MS Calcd.: 7310.13.
Found: 7310.17.

Example 6

PMO. No. 5

The title compound was produced in accordance with the procedure of EXAMPLE 1, except that 4-(((2S,6R)-6-(5-methyl-2,4-dioxo-3,4-dihydropyrimidin-1(2H)-yl)-4-tritylmorpholin-2-yl)methoxy)-4-oxobutanoic acid loaded onto aminomethyl polystyrene resin (REFERENCE EXAMPLE 3) was used as the starting material.

ESI-TOF-MS Calcd.: 8270.94.
Found: 8270.20.

Example 7

PMO. No. 6

The title compound was produced in accordance with the procedure of EXAMPLE 1.

ESI-TOF-MS Calcd.: 5964.01.
Found: 5963.68.

Example 8

PMO. No. 7

The title compound was produced in accordance with the procedure of EXAMPLE 1.

ESI-TOF-MS Calcd.: 6609.55.
Found: 6608.85.

Example 9

PMO. No. 9

The title compound was produced in accordance with the procedure of EXAMPLE 1, except that 4-oxo-4-(((2S,6R)-6-(6-oxo-2-(2-phenoxyacetamido)-1H-purin-9 (6H)-yl)-4-tritylmorpholin-2-yl)methoxy)butanoic acid loaded onto aminomethyl polystyrene resin (REFERENCE EXAMPLE 2) was used as the starting material.

ESI-TOF-MS Calcd.: 7280.11.
Found: 7279.42.

Example 10

PMO. No. 10

The title compound was produced in accordance with the procedure of EXAMPLE 1, except that 4-oxo-4-(((2S,6R)-6-(6-oxo-2-(2-phenoxyacetamido)-1H-purin-9 (6H)-yl)-4-tritylmorpholin-2-yl)methoxy)butanoic acid loaded onto aminomethyl polystyrene resin (REFERENCE EXAMPLE 2) was used as the starting material.

ESI-TOF-MS Calcd.: 8295.95.
Found: 8295.91.

Example 11

PMO. No. 13

The title compound was produced in accordance with the procedure of EXAMPLE 1, except that 1,12-dioxo-1-(4-tritylpiperazin-1-yl)-2,5,8,11-tetraoxa-15-pentadecanoic acid loaded onto aminomethyl polystyrene resin (REFERENCE EXAMPLE 4) was used as the starting material.

ESI-TOF-MS Calcd.: 7276.15.
Found: 7276.69.

Example 12

PMO. No. 14

The title compound was produced in accordance with the procedure of EXAMPLE 1, except that 1,12-dioxo-1-(4-tritylpiperazin-1-yl)-2,5,8,11-tetraoxa-15-pentadecanoic acid loaded onto aminomethyl polystyrene resin (REFERENCE EXAMPLE 4) was used as the starting material.

ESI-TOF-MS Calcd.: 8622.27.
Found: 8622.29.

Comparative Example 1

PMO. No. 11

The title compound was produced in accordance with the procedure of EXAMPLE 1.

ESI-TOF-MS Calcd.: 10274.63.
Found: 10273.71.

Comparative Example 2

PMO. No. 15

The title compound was produced in accordance with the procedure of EXAMPLE 1.

ESI-TOF-MS Calcd.: 9941.33.
Found: 9940.77.

Comparative Example 3

PMO. No. 16

The title compound was produced in accordance with the procedure of EXAMPLE 1.

ESI-TOF-MS Calcd.: 8238.94.
Found: 8238.69.

Test Example 1

In Vitro Assay

Using an Amaxa Cell Line Nucleofector Kit L on Nucleofector II (Lonza), 10 µM of the oligomers PMO Nos. 1 to 8 of the present invention and the antisense oligomer PMO No. 11 were transfected with $4 \times 10^5$ of RD cells (human rhabdomyosarcoma cell line). The Program T-030 was used.

After transfection, the cells were cultured overnight in 2 mL of Eagle's minimal essential medium (EMEM) (manufactured by Sigma, hereinafter the same) containing 10% fetal calf serum (FCS) (manufactured by Invitrogen) under conditions of 37° C. and 5% $CO_2$. The cells were washed twice with PBS (manufactured by Nissui, hereinafter the same) and 500 µl of ISOGEN (manufactured by Nippon Gene) was added to the cells. After the cells were allowed to stand at room temperature for a few minutes to lyse the cells, the lysate was collected in an Eppendorf tube. The total RNA was extracted according to the protocol attached to ISOGEN. The concentration of the total RNA extracted was determined using a NanoDrop ND-1000 (manufactured by LMS).

One-Step RT-PCR was performed with 400 ng of the extracted total RNA using a Titan One Tube RT-PCR Kit (manufactured by Roche). A reaction solution was prepared in accordance with the protocol attached to the kit. A PTC-100 (manufactured by MJ Research) was used as a thermal cycler. The RT-PCR program used is as follows.

50° C., 30 mins: reverse transcription
94° C., 2 mins: thermal denaturation
[94° C., 10 seconds; 58° C., 30 seconds; 68° C., 45 seconds]×30 cycles: PCR amplification
68° C., 7 mins: final extension The nucleotide sequences of the forward primer and reverse primer used for RT-PCR are given below.

```
Forward primer:
                          (SEQ ID NO: 40)
5'-AGGATTTGGAACAGAGGCGTC-3'

Reverse primer:
                          (SEQ ID NO: 41)
5'-GTCTGCCACTGGCGGAGGTC-3'
```

Next, a nested PCR was performed with the product amplified by RT-PCR above using a Taq DNA Polymerase (manufactured by Roche). The PCR program used is as follows.

94° C., 2 mins: thermal denaturation
[94° C., 15 seconds; 58° C., 30 seconds; 68° C., 45 seconds]×30 cycles: PCR amplification
68° C., 7 mins: final extension The nucleotide sequences of the forward primer and reverse primer used for the nested PCR above are given below.

```
Forward primer:
                          (SEQ ID NO: 42)
5'-CATCAAGCAGAAGGCAACAA-3'

Reverse primer:
                          (SEQ ID NO: 43)
5'-GAAGTTTCAGGGCCAAGTCA-3'
```

The reaction product, 1 µl, of the nested PCR above was analyzed using a Bioanalyzer (manufactured by Agilent Technologies, Inc.).

The polynucleotide level "A" of the band with exon 53 skipping and the polynucleotide level "B" of the band without exon 53 skipping were measured. Based on these measurement values of "A" and "B," the skipping efficiency was determined by the following equation:

Skipping efficiency(%)=$A/(A+B)\times100$

Experimental Results

The results are shown in FIG. 1. This experiment revealed that the oligomers PMO Nos. 1 to 8 of the present invention caused exon 53 skipping with a markedly high efficiency as compared to the antisense oligomer PMO No. 11. In particular, the oligomers PMO Nos. 3 and 8 of the present invention exhibited more than four times higher exon skipping efficiency than that of the antisense oligomer PMO No. 11.

Test Example 2

In Vitro Assay Using Human Fibroblasts

Human myoD gene (SEQ ID NO: 44) was introduced into TIG-119 cells (human normal tissue-derived fibroblasts, National Institute of Biomedical Innovation) or 5017 cells (human DMD patient-derived fibroblasts, Coriell Institute for Medical Research) using a ZsGreen1 coexpression retroviral vector.

After incubation for 4 to 5 days, ZsGreen-positive MyoD-transformed fibroblasts were collected by FACS and plated at $5\times10^4/cm^2$ into a 12-well plate. As a growth medium, there was used 1 mL of Dulbecco's Modified Eagle Medium: Nutrient Mixture F-12 (DMEM.F-12) (Invitrogen Corp.) containing 10% FCS and 1% Penicillin/Streptomycin (P/S) (Sigma-Aldrich, Inc.).

The medium was replaced 24 hours later by differentiation medium (DMEM/F-12 containing 2% equine serum (Invitrogen Corp.), 1% P/S and ITS Liquid Media Supplement (Sigma, Inc.)). The medium was exchanged every 2 to 3 days and incubation was continued for 12 to 14 days to differentiate into myotubes.

Subsequently, the differentiation medium was replaced by a differentiation medium containing 6 µM Endo-Porter (Gene Tools), and the morpholino oligomer was added thereto in a final concentration of 10 µM. After incubation for 48 hours, total RNA was extracted from the cells using a TRIzol (manufactured by Invitrogen Corp.). RT-PCR was performed with 50 ng of the extracted total RNA using a QIAGEN OneStep RT-PCR Kit. A reaction solution was prepared in accordance with the protocol attached to the kit. An iCycler (manufactured by Bio-Rad) was used as a thermal cycler. The RT-PCR program used is as follows.

50° C., 30 mins: reverse transcription
95° C., 15 mins: thermal denaturation
[94° C., 1 mins; 60° C., 1 mins; 72° C., 1 mins]×35 cycles: PCR amplification
72° C., 7 mins: final extension The primers used were hEX51F and hEX55R.

```
hEX51F:
                          (SEQ ID NO: 45)
5'-CGGGCTTGGACAGAACTTAC-3' hEx55R:
                          (SEQ ID NO: 46)
5'-TCCTTTACGGGTAGCATCCTG-3'
```

The reaction product of RT-PCR above was separated by 2% agarose gel electrophoresis and gel images were captured with a GeneFlash (Syngene). The polynucleotide level "A" of the band with exon 53 skipping and the polynucleotide level "B" of the band without exon 53 skipping were measured using an Image J (manufactured by National Institutes of Health). Based on these measurement values of "A" and "B," the skipping efficiency was determined by the following equation.

Skipping efficiency(%)=$A/A+B)\times100$

Experimental Results

Figure 2:
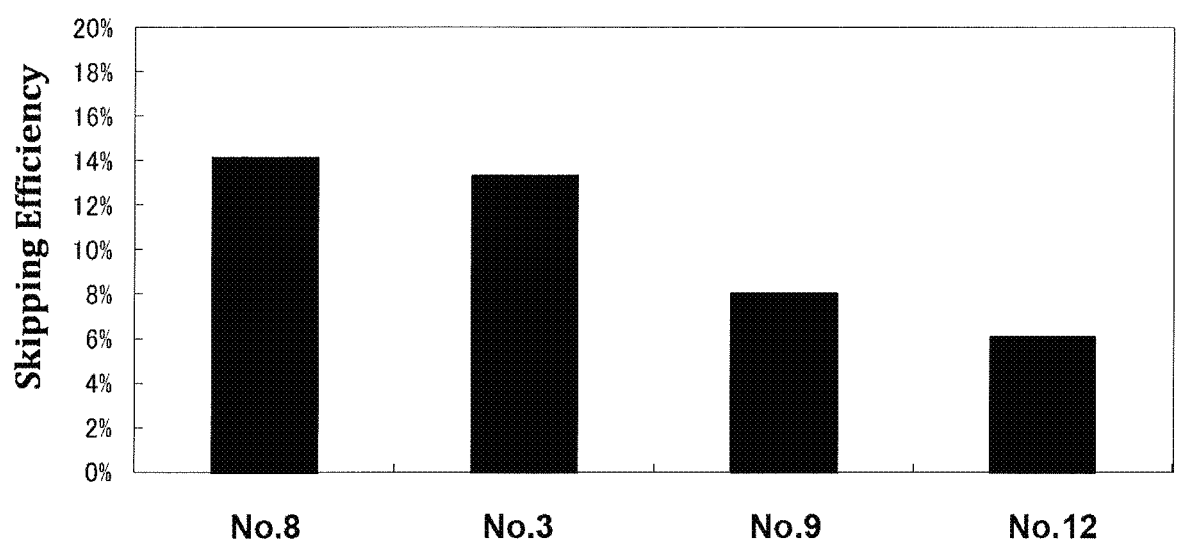
FIG. 2 shows the efficiency of exon 53 skipping in the human dystrophin gene in the cells where human myoD gene is introduced into human normal tissue-derived fibroblasts (TIG-119 cells) to induce differentiation into muscle cells.
Figure 3:
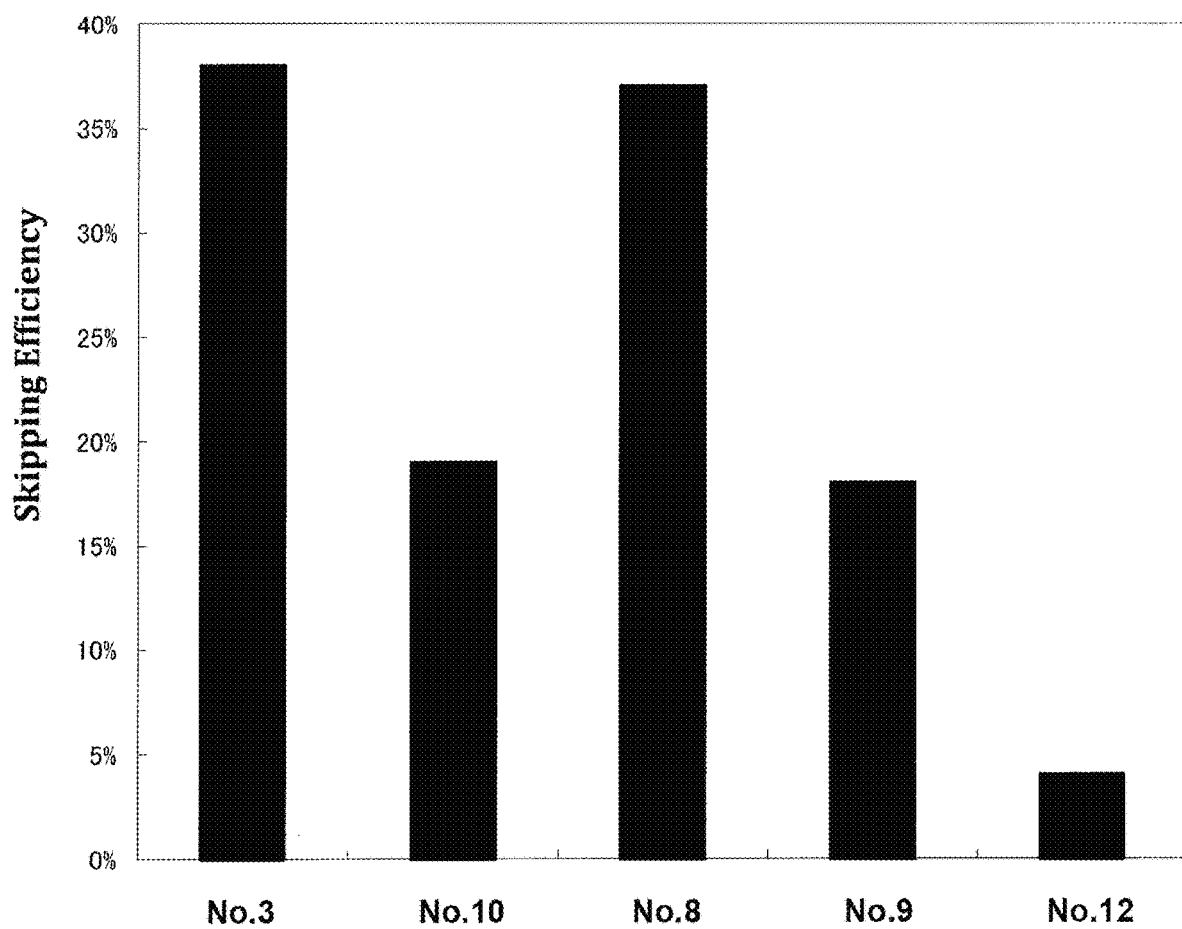
FIG. 3 shows the efficiency of exon 53 skipping in the human dystrophin gene in the cells where human myoD gene is introduced into human DMD patient-derived fibroblasts (5017 cells) to induce differentiation into muscle cells.

The results are shown in FIGS. 2 and 3. This experiment revealed that in TIG-119 cells, the oligomers PMO Nos. 3, 8 and 9 of the present invention (FIG. 2) all caused exon 53 skipping with a higher efficiency than the antisense oligomer PMO No. 12 (FIG. 2). In particular, the oligomers PMO Nos. 3 and 8 of the present invention exhibited more than twice higher exon skipping efficiency than that of the antisense oligomer PMO No. 12 (FIG. 2).

Furthermore, this experiment revealed that the oligomers PMO Nos. 3 and 8 to 10 of the present invention (FIG. 3) all caused exon 53 skipping with a higher efficiency than the antisense oligomer PMO No. 12 (FIG. 3). In particular, the oligomers PMO Nos. 3 and 8 of the present invention exhibited more than seven times higher exon skipping efficiency than that of the antisense oligomer PMO No. 12 (FIG. 3).

Test Example 3

In Vitro Assay Using Human Fibroblasts

The skin fibroblast cell line (fibroblasts from human DMD patient (exons 45-52 or exons 48-52)) was established by biopsy from the medial left upper arm of DMD patient with deletion of exons 45-52 or DMD patient with deletion of exons 48-52. Human myoD gene (SEQ ID NO: 44) was introduced into the fibroblast cells using a ZsGreen1 coexpression retroviral vector.

After incubation for 4 to 5 days, ZsGreen-positive MyoD-transformed fibroblasts were collected by FACS and plated at $5 \times 10^4/cm^2$ into a 12-well plate. As a growth medium, there was used 1 mL of Dulbecco's Modified Eagle Medium: Nutrient Mixture F-12 (DMEM/F-12) (Invitrogen Corp.) containing 10% FCS and 1% Penicillin/Streptomycin (P/S) (Sigma-Aldrich, Inc.).

The medium was replaced 24 hours later by a differentiation medium (DMEM/F-12 containing 2% equine serum (Invitrogen Corp.), 1% P/S and ITS Liquid Media Supplement (Sigma, Inc.)). The medium was exchanged every 2 to 3 days and incubation was continued for 12, 14 or 20 days to differentiate into myotubes.

Subsequently, the differentiation medium was replaced by a differentiation medium containing 6 μM Endo-Porter (Gene Tools), and a morpholino oligomer was added thereto at a final concentration of 10 μM. After incubation for 48 hours, total RNA was extracted from the cells using a TRIzol (manufactured by Invitrogen Corp.). RT-PCR was performed with 50 ng of the extracted total RNA using a QIAGEN OneStep RT-PCR Kit. A reaction solution was prepared in accordance with the protocol attached to the kit. An iCycler (manufactured by Bio-Rad) was used as a thermal cycler. The RT-PCR program used is as follows.

50° C., 30 mins: reverse transcription
95° C., 15 mins: thermal denaturation
[94° C., 1 mins; 60° C., 1 mins; 72° C., 1 mins]×35 cycles: PCR amplification
72° C., 7 mins: final extension
The primers used were hEx44F and h55R.

```
hEx44F:
                                  (SEQ ID NO: 48)
5'-TGTTGAGAAATGGCGGCGT-3' hEx55R:
                                  (SEQ ID NO: 46)
5'-TCCTTACGGGTAGCATCCTG-3'
```

The reaction product of RT-PCR above was separated by 2% agarose gel electrophoresis and gel images were captured with a GeneFlash (Syngene). The polynucleotide level "A" of the band with exon 53 skipping and the polynucleotide level "B" of the band without exon 53 skipping were measured using an Image J (manufactured by National Institutes of Health). Based on these measurement values of "A" and "B," the skipping efficiency was determined by the following equation.

Skipping efficiency(%)=$A/(A+B) \times 100$

Experimental Results

Figure 4:
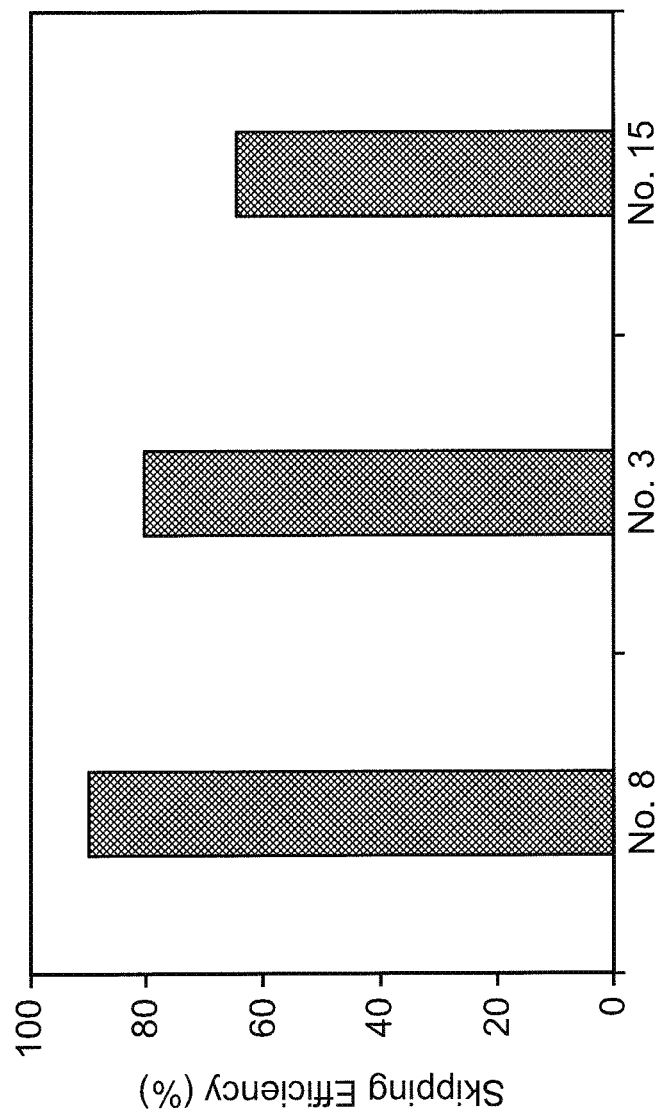
FIG. 4 shows the efficiency of exon 53 skipping in the human dystrophin gene in the cells where human myoD gene is introduced into fibroblasts from human DMD patient (with deletion of exons 45-52) to induce differentiation into muscle cells.
Figure 5:
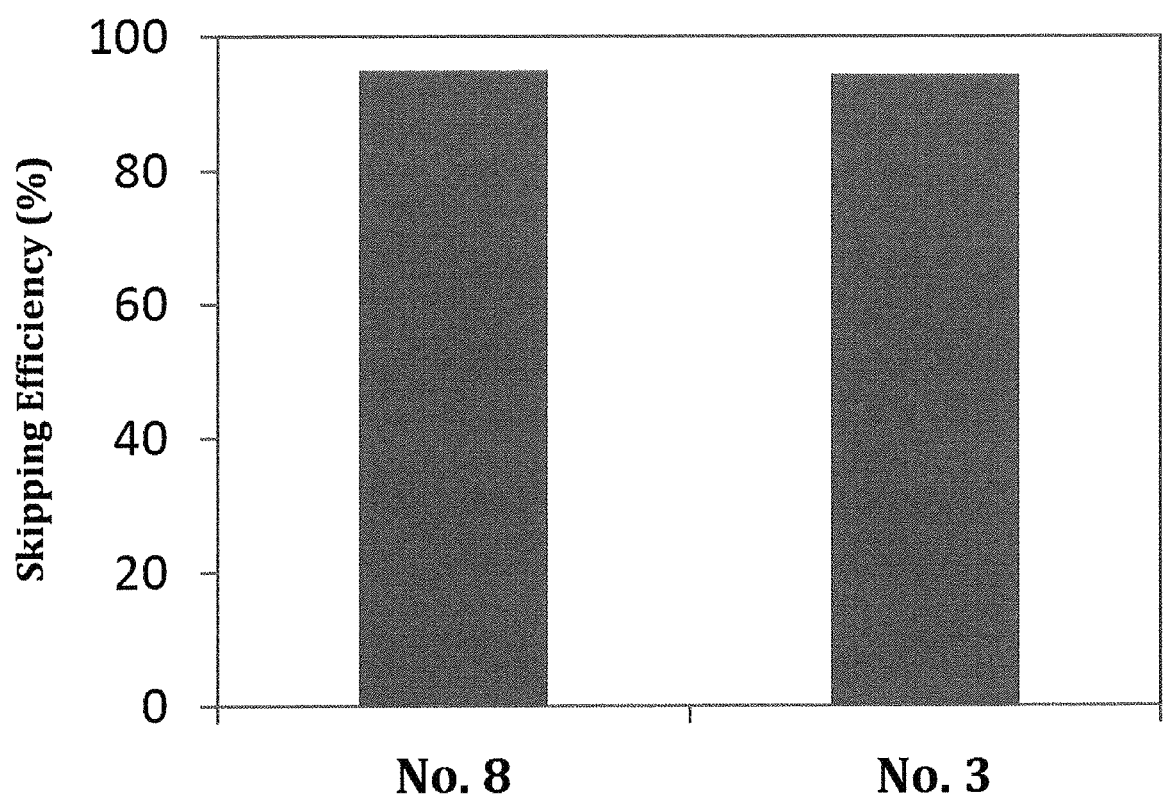
FIG. 5 shows the efficiency of exon 53 skipping in the human dystrophin gene in the cells where human myoD gene is introduced into fibroblasts from human DMD patient (with deletion of exons 48-52) to induce differentiation into muscle cells.

The results are shown in FIGS. 4 and 5. This experiment revealed that the oligomers PMO Nos. 3 and 8 of the present invention caused exon 53 skipping with an efficiency as high as more than 80% in the cells from DMD patient with deletion of exons 45-52 (FIG. 4) or deletion of exons 48-52 (FIG. 5). Also, the oligomers PMO Nos. 3 and 8 of the present invention were found to cause exon 53 skipping with a higher efficiency than that of the antisense oligomer PMO No. 15 in the cells from DMD patient with deletion of exons 45-52 (FIG. 4).

Test Example 4

Western Blotting

The oligomer PMO No. 8 of the present invention was added to the cells at a concentration of 10 μM, and proteins were extracted from the cells after 72 hours using a RIPA buffer (manufactured by Thermo Fisher Scientific) containing Complete Mini (manufactured by Roche Applied Science) and quantified using a BCA protein assay kit (manufactured by Thermo Fisher Scientific). The proteins were electrophoresed in NuPAGE Novex Tris-Acetate Gel 3-8% (manufactured by Invitrogen) at 150V for 75 minutes and transferred onto a PVDF membrane (manufactured by Millipore) using a semi-dry blotter. The PVDF membrane was blocked with a 5% ECL Blocking agent (manufactured by GE Healthcare) and the membrane was then incubated in a solution of anti-dystrophin antibody (manufactured by NCL-Dys1, Novocastra). After further incubation in a solution of peroxidase-conjugated goat-antimouse IgG (Model No. 170-6516, Bio-Rad), the membrane was stained with ECL Plus Western blotting system (manufactured by GE Healthcare).

Immunostaining

The oligomer PMO No. 3 or 8 of the present invention was added to the cells. The cells after 72 hours were fixed in 3% paraformaldehyde for 10 minutes, followed by incubation in 10% Triton-X for 10 minutes. After blocking in 10% goat serum-containing PBS, the membrane was incubated in a solution of anti-dystrophin antibody (NCL-Dys1, Novocastra). The membrane was further incubated in a solution of anti-mouse IgG antibody (manufactured by Invitrogen). The membrane was mounted with Pro Long Gold Antifade reagent (manufactured by Invitrogen) and observed with a fluorescence microscope.

Experimental Results

Figure 6:
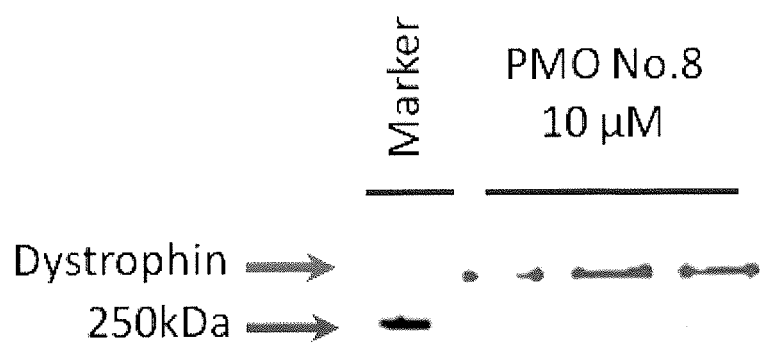
FIG. 6 shows the efficiency of exon 53 skipping in the human dystrophin gene in the cells where human myoD gene is introduced into fibroblasts from human DMD patient (with deletion of exons 48-52) to induce differentiation into muscle cells.

The results are shown in FIGS. 6 and 7. In this experiment it was confirmed by western blotting (FIG. 6) and immunostaining (FIG. 7) that the oligomers PMO Nos. 3 and 8 of the present invention induced expression of the dystrophin protein.

Test Example 5

In Vitro Assay Using Human Fibroblasts

The experiment was performed as in TEST EXAMPLE 3.

Experimental Results

Figure 8:
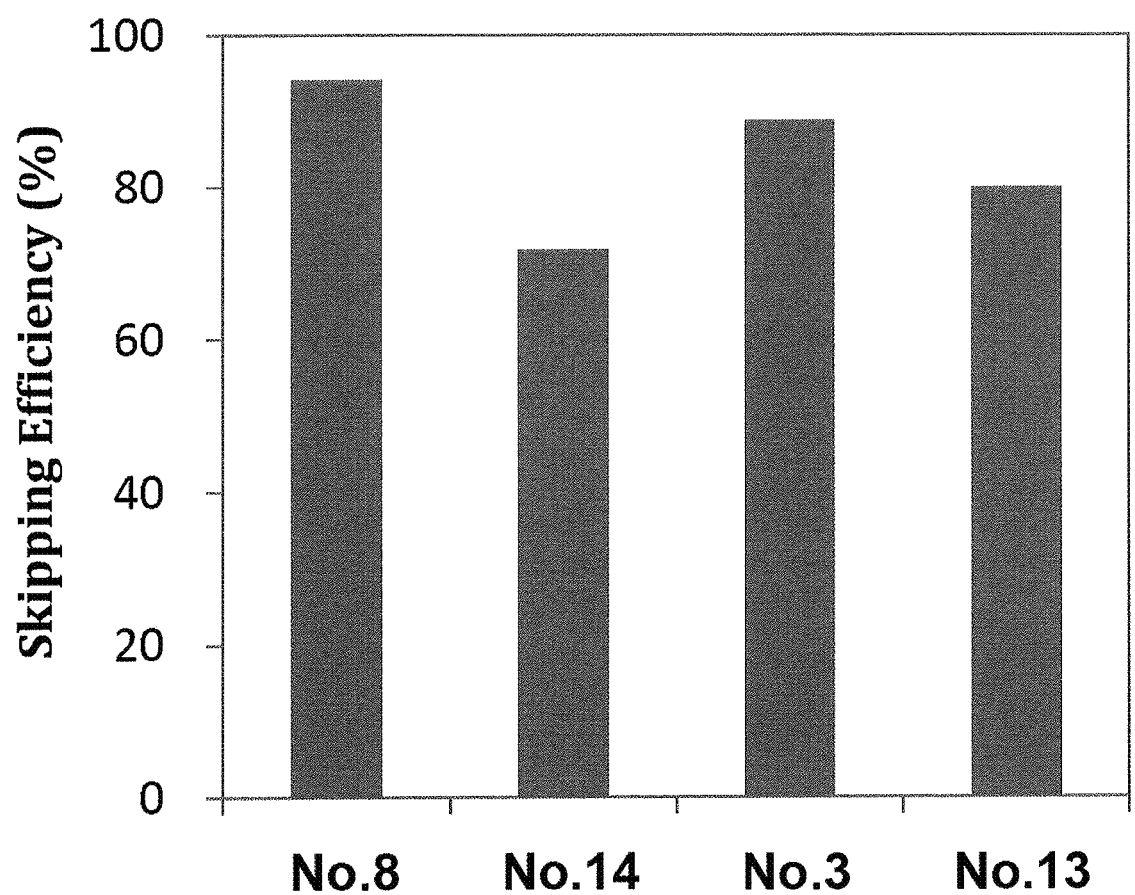
FIG. 8 shows the efficiency of exon 53 skipping in the human dystrophin gene in the cells where human myoD gene is introduced into fibroblasts from human DMD patient (with deletion of exons 45-52) to induce differentiation into muscle cells.
Figure 9:
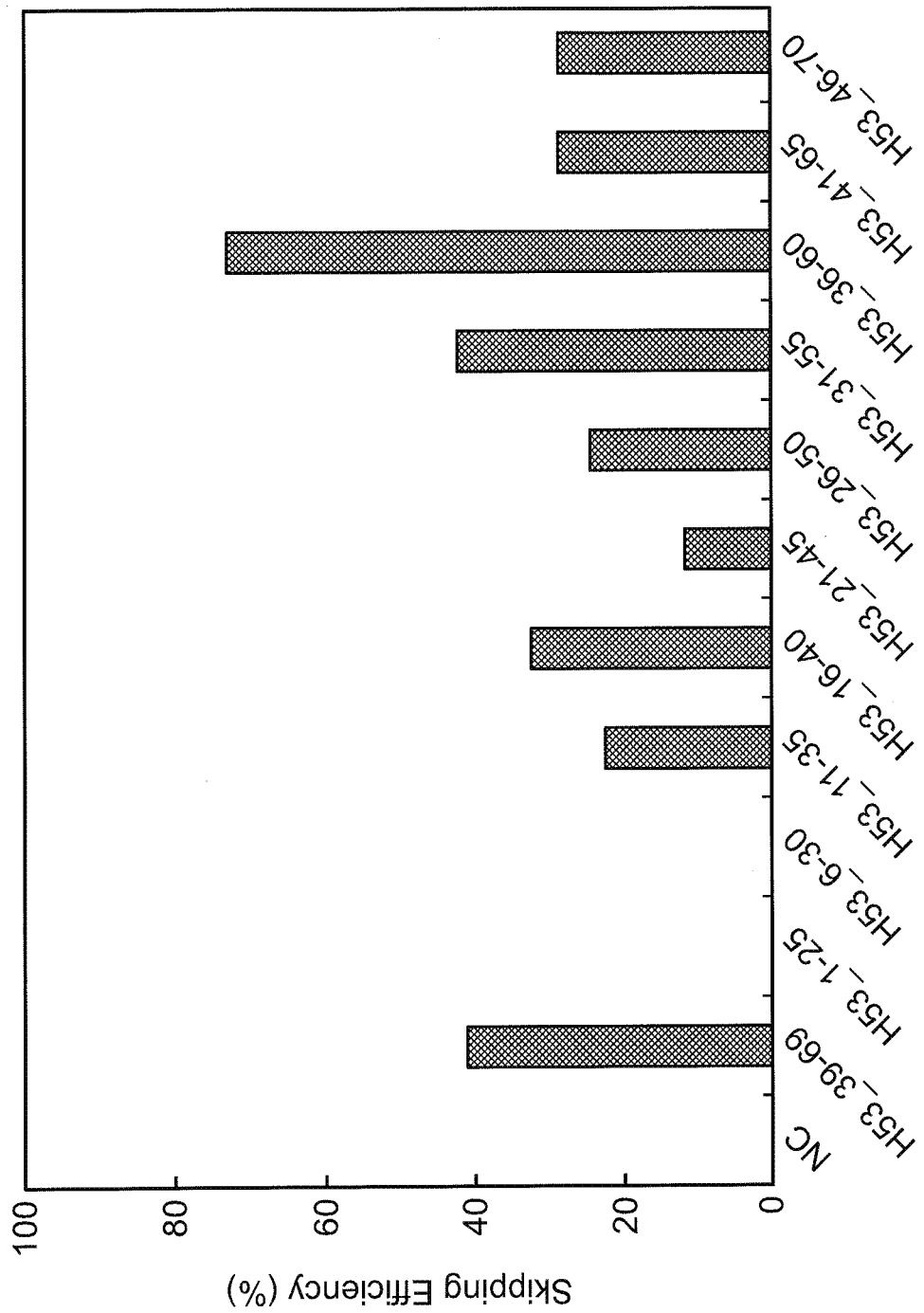
FIG. 9 shows the efficiency of exon 53 skipping (2'-OMe-S-RNA) in the human dystrophin gene in human rhabdomyosarcoma cells (RD cells).
Figure 10:
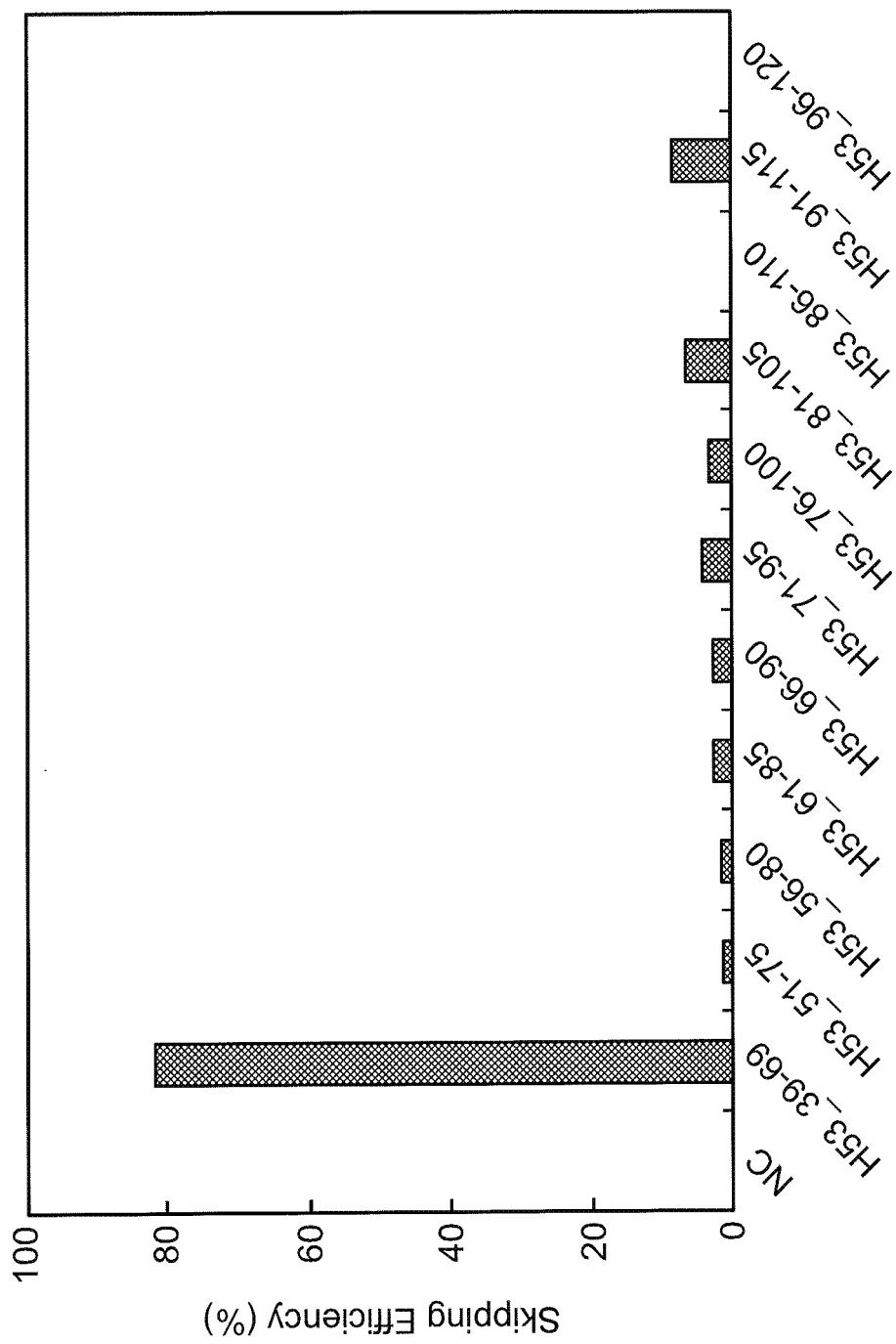
FIG. 10 shows the efficiency of exon 53 skipping (2'-OMe-S-RNA) in the human dystrophin gene in human rhabdomyosarcoma cells (RD cells).
Figure 11:
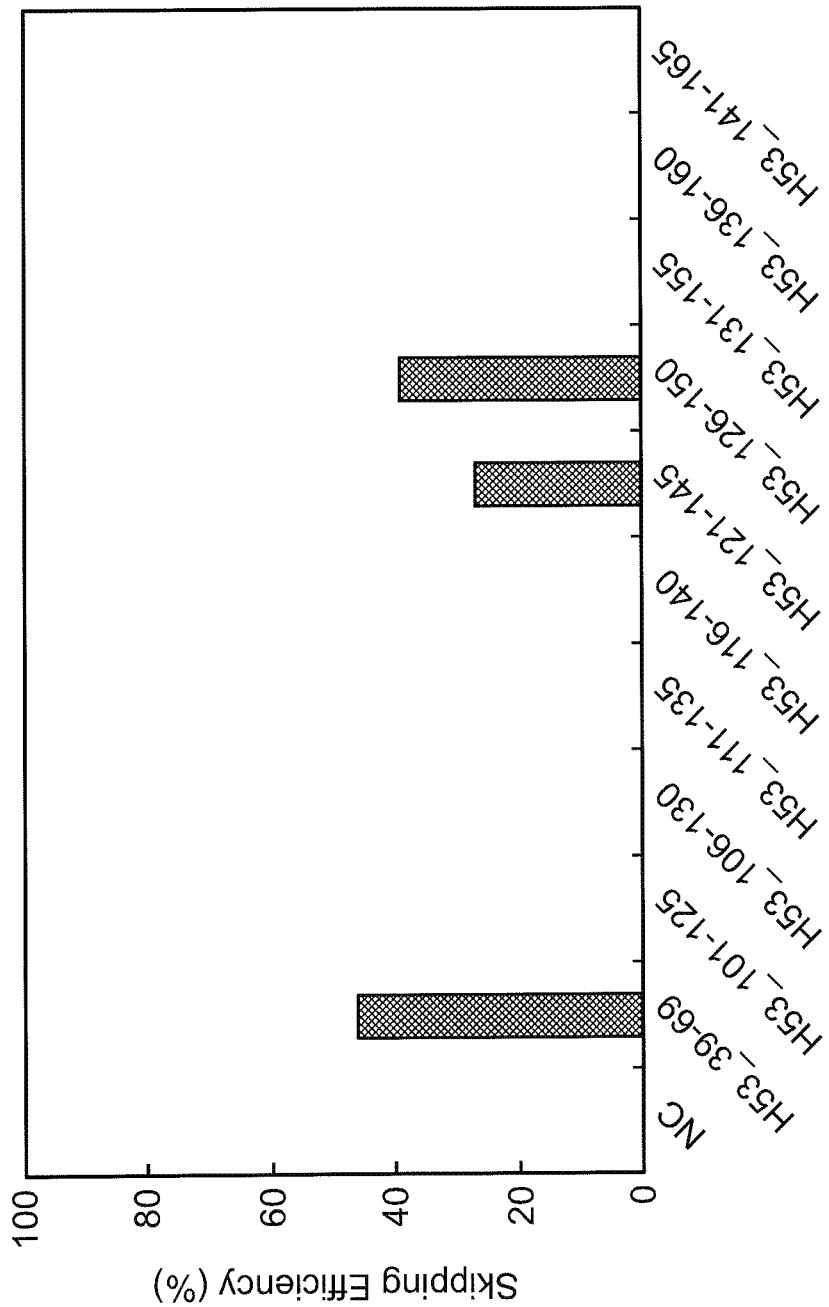
FIG. 11 shows the efficiency of exon 53 skipping (2'-OMe-S-RNA) in the human dystrophin gene in human rhabdomyosarcoma cells (RD cells).
Figure 12:
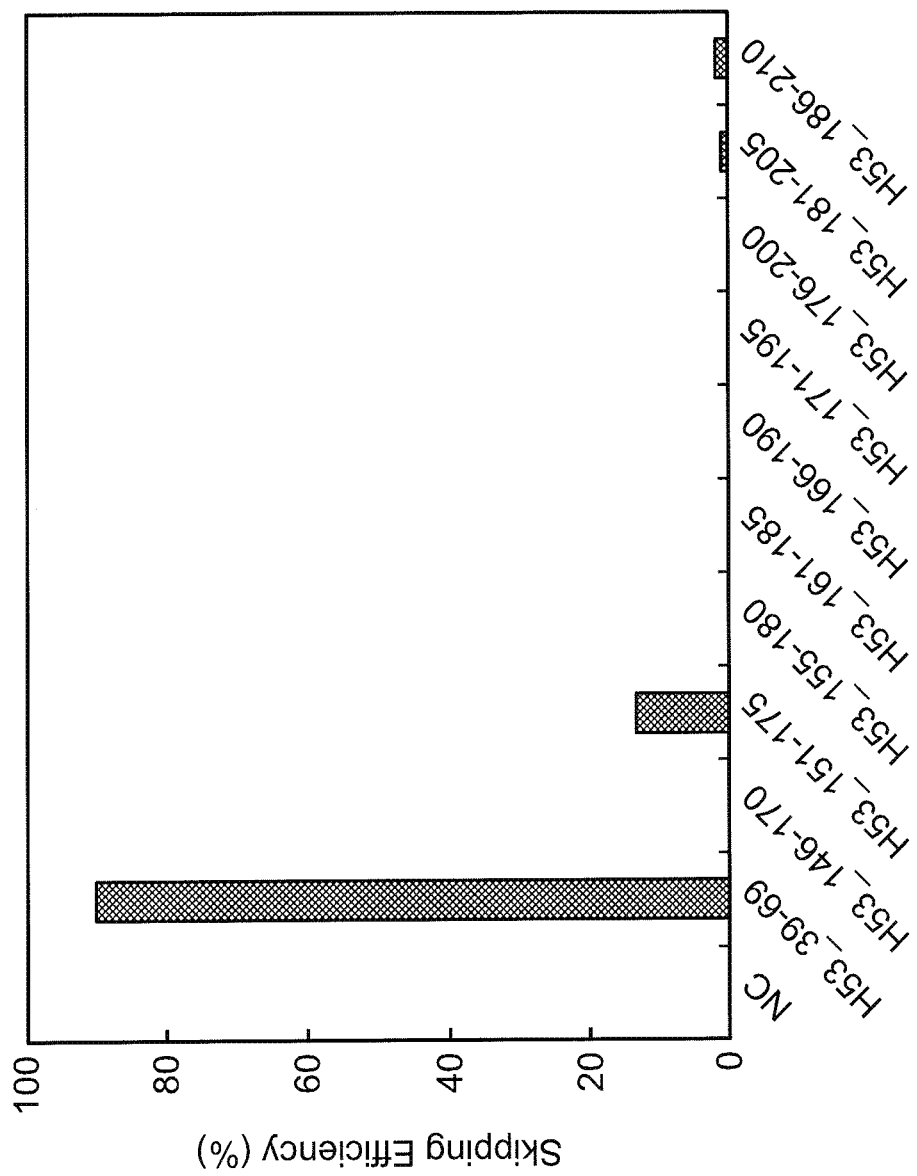
FIG. 12 shows the efficiency of exon 53 skipping (2'-OMe-S-RNA) in the human dystrophin gene in human rhabdomyosarcoma cells (RD cells).
Figure 13:
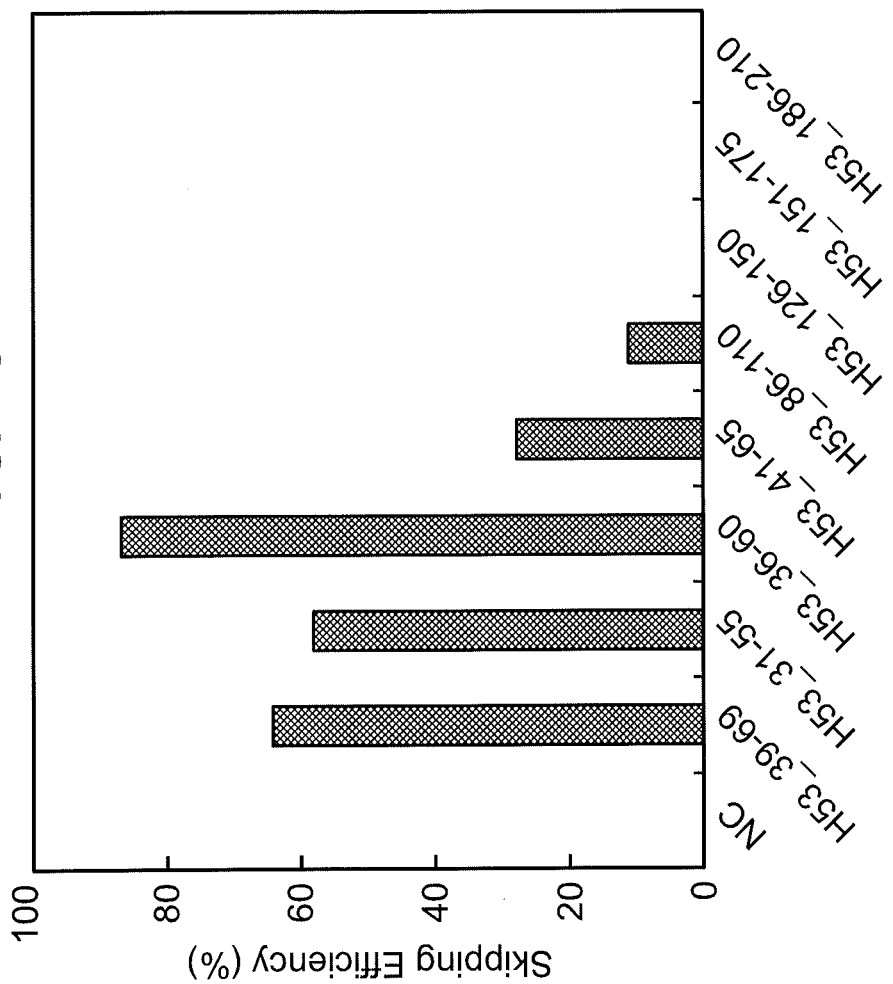
FIG. 13 shows the efficiency of exon 53 skipping (2'-OMe-S-RNA) in the human dystrophin gene in human rhabdomyosarcoma cells (RD cells).
Figure 14:
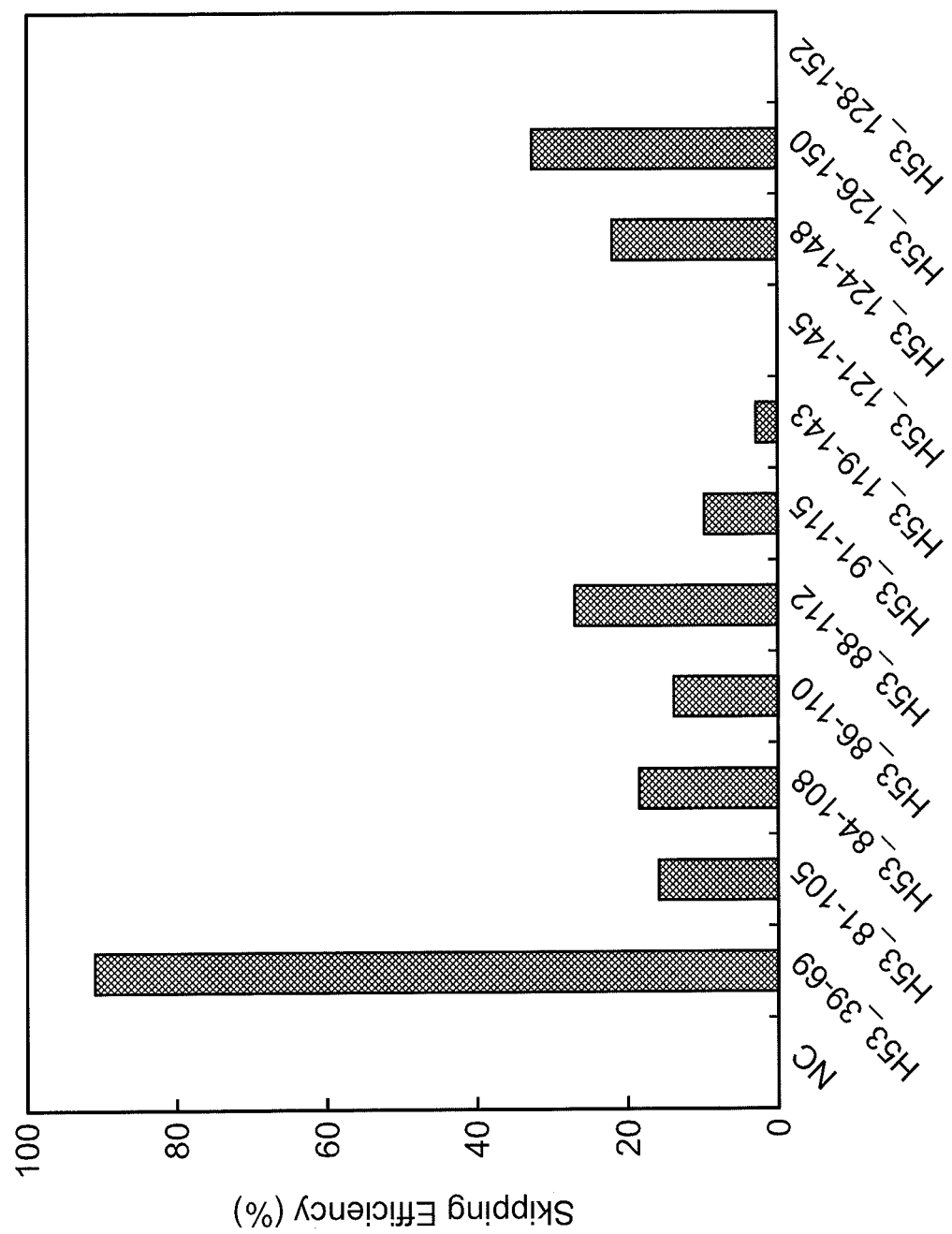
FIG. 14 shows the efficiency of exon 53 skipping (2'-OMe-S-RNA) in the human dystrophin gene in human rhabdomyosarcoma cells (RD cells).
Figure 15:
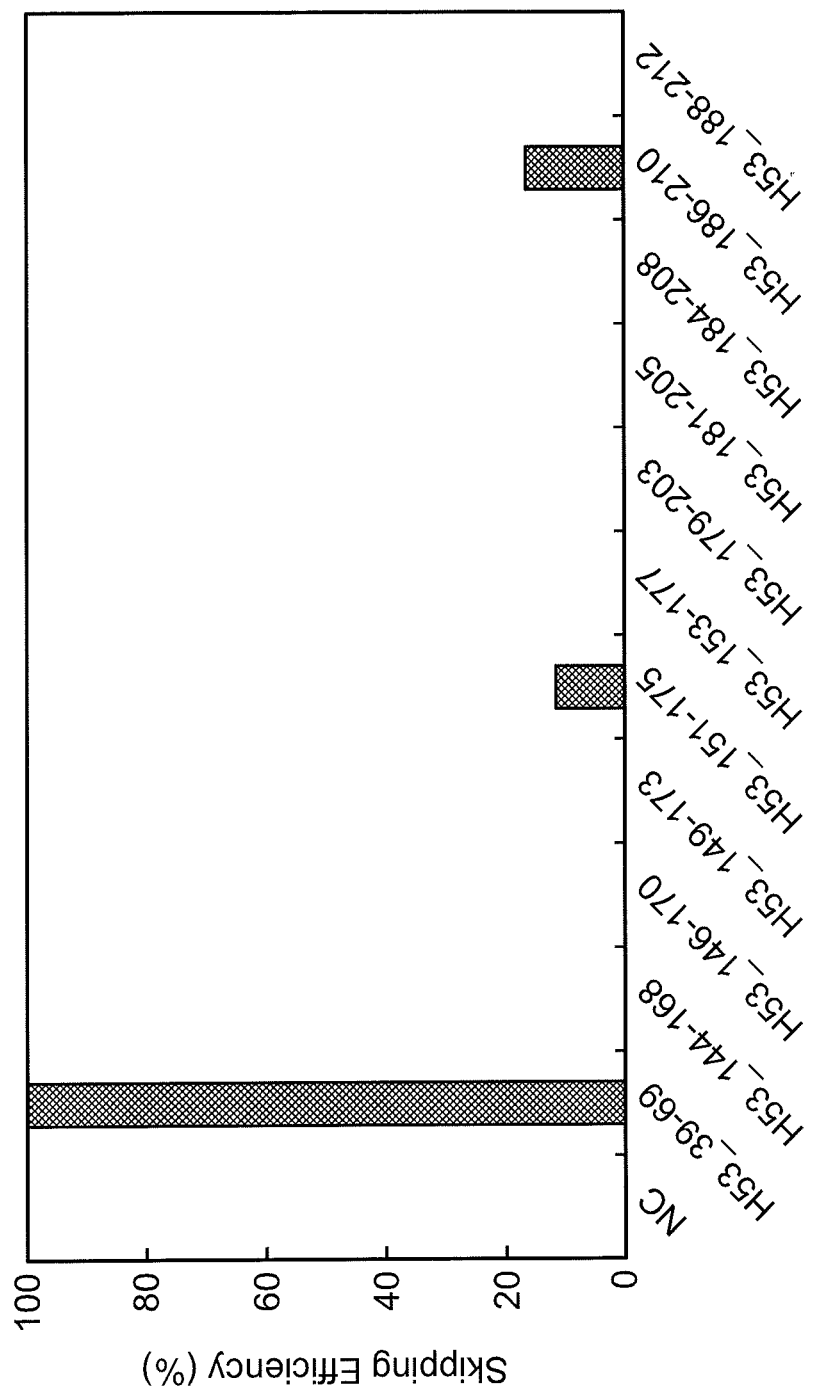
FIG. 15 shows the efficiency of exon 53 skipping (2'-OMe-S-RNA) in the human dystrophin gene in human rhabdomyosarcoma cells (RD cells).
Figure 16:
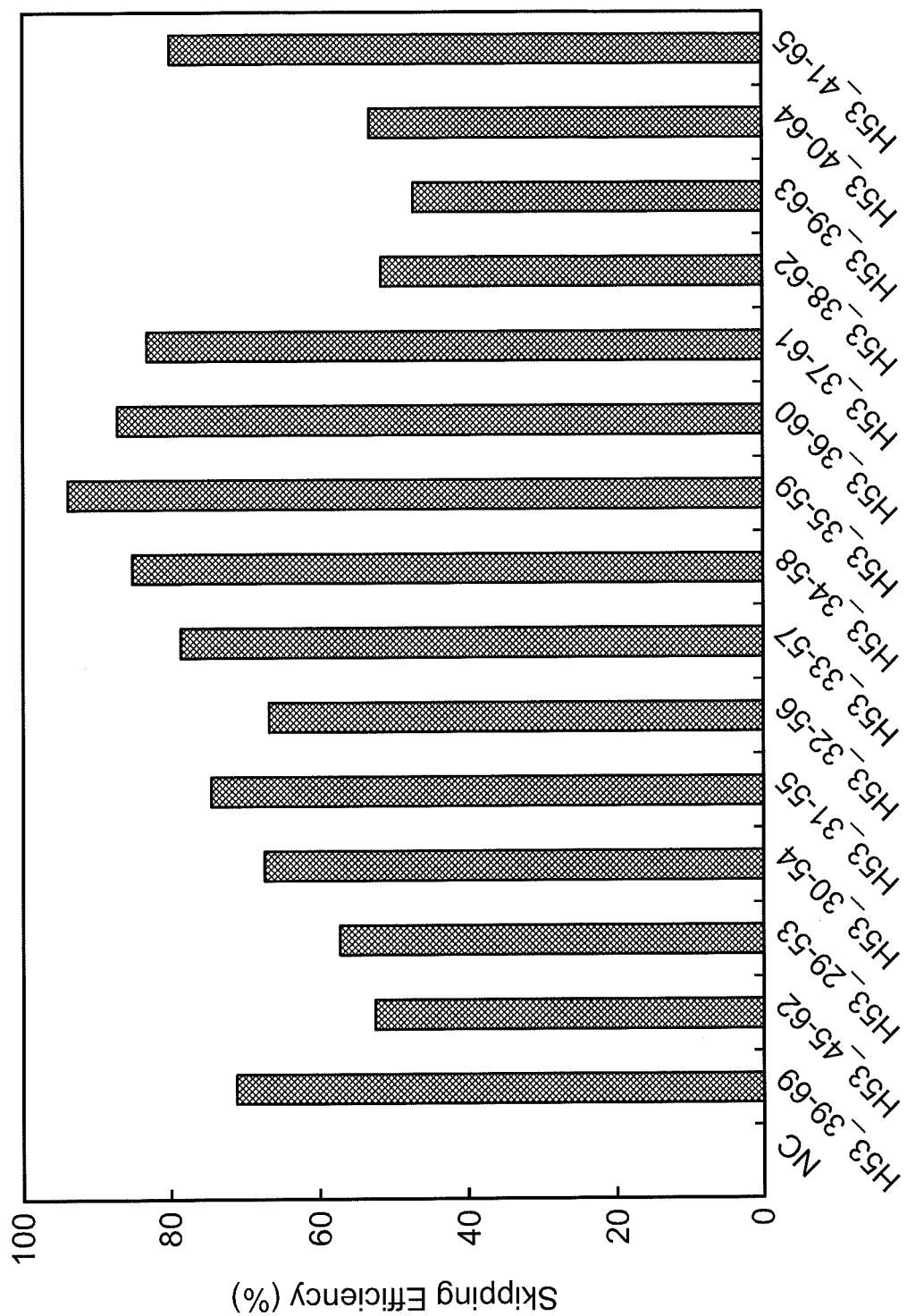
FIG. 16 shows the efficiency of exon 53 skipping (2'-OMe-S-RNA) in the human dystrophin gene in human rhabdomyosarcoma cells (RD cells).
Figure 17:
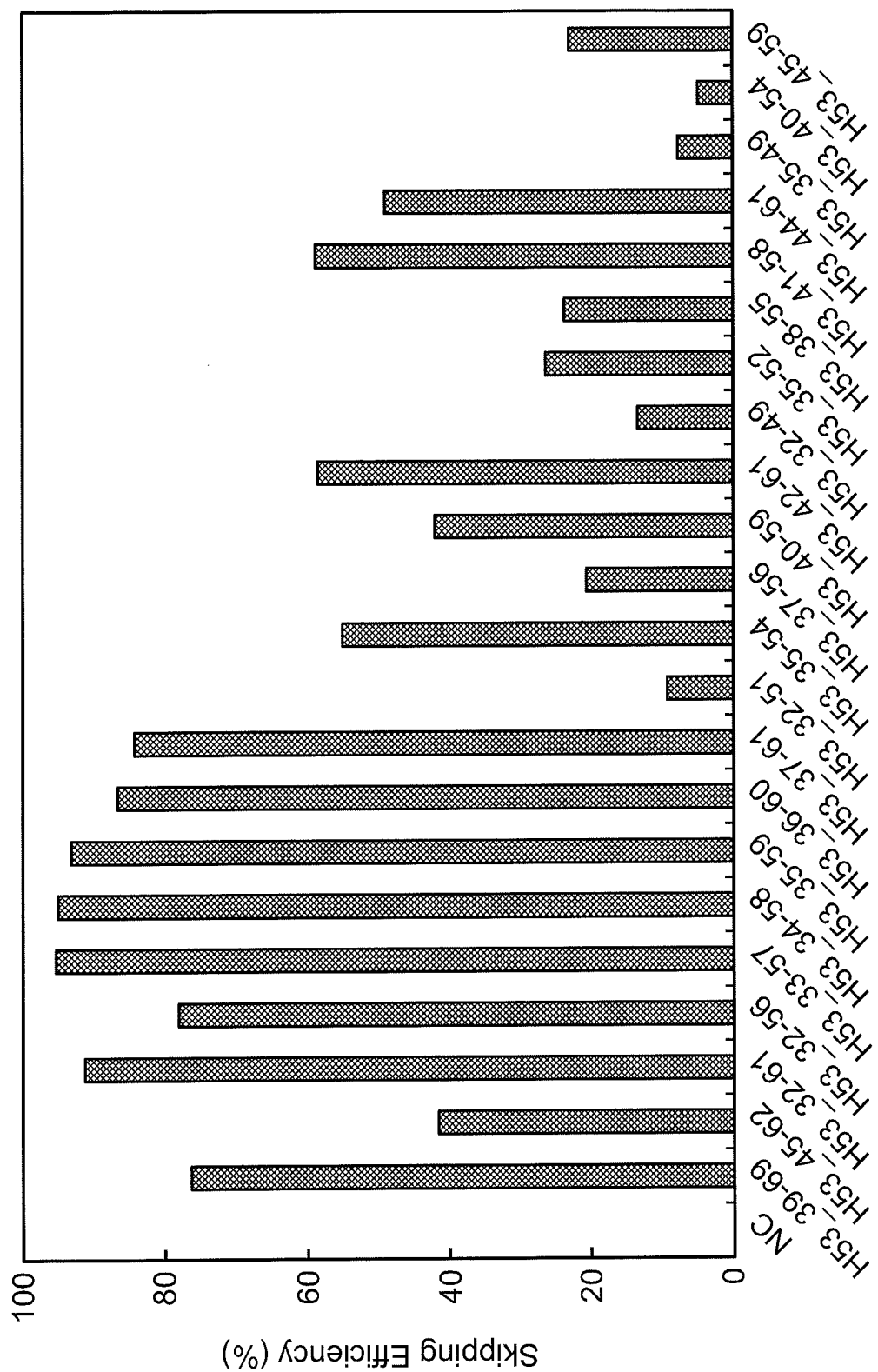
FIG. 17 shows the efficiency of exon 53 skipping (2'-OMe-S-RNA) in the human dystrophin gene in human rhabdomyosarcoma cells (RD cells).

The results are shown in FIG. 8. This experiment revealed that in the cells from DMD patients with deletion of exons 45-52, the oligomers PMO Nos. 3 to 8 of the present invention caused exon 53 skipping with a higher efficiency than the oligomers PMO Nos. 13 and 14 of the present invention (FIG. 8).

Test Example 6

In Vitro Assay

Experiments were performed using the antisense oligomers of 2'-O-methoxy-phosphorothioates (2-OMe-S-RNA) shown by SEQ ID NO: 49 to SEQ ID NO: 123. Various antisense oligomers used for the assay were purchased from Japan Bio Services. The sequences of various antisense oligomers are given below.

TABLE 7

| Antisense oligomer | Nucleotide sequence | SEQ ID NO: |
|---|---|---|
| H53_39-69 | CAUUCAACUGUUGCCUCCGGUUCUGAAGGUG | 49 |
| H53_1-25 | UCCCACUGAUUCUGAAUUCUUUCAA | 50 |
| H53_6-30 | CUUCAUCCCACUGAUUCUGAAUUCU | 51 |
| H53_11-35 | UUGUACUUCAUCCCACUGAUUCUGA | 52 |
| H53_16-40 | UGUUCUUGUACUUCAUCCCACUGAU | 53 |
| H53_21-45 | GAAGGUGUUCUUGUACUUCAUCCCA | 54 |
| H53_26-50 | GUUCUGAAGGUGUUCUUGUACUUCA | 55 |
| H53_31-55 | CUCCGGUUCUGAAGGUGUUCUUGUA | 56 |
| H53_36-60 | GUUGCCUCCGGUUCUGAAGGUGUUC | 57 |
| H53_41-65 | CAACUGUUGCCUCCGGUUCUGAAGG | 58 |
| H53_46-70 | UCAUUCAACUGUUGCCUCCGGUUCU | 59 |
| H53_51-75 | ACAUUCAUUCAACUGUUGCCUCCG | 60 |
| H53_56-80 | CUUUAACAUUUCAUUCAACUGUUGC | 61 |
| H53_61-85 | GAAUCCUUUAACAUUUCAUUCAACU | 62 |
| H53_66-90 | GUGUUGAAUCCUUUAACAUUUCAUU | 63 |
| H53_71-95 | CCAUUGUGUUGAAUCCUUUAACAUU | 64 |
| H53_76-100 | UCCAGCCAUUGUGUUGAAUCCUUUA | 65 |
| H53_81-105 | UAGCUUCCAGCCAUUGUGUUGAAUC | 66 |
| H53_86-110 | UUCCUUAGCUUCCAGCCAUUGUGUU | 67 |
| H53_91-115 | GCUUCUUCCUUAGCUUCCAGCCAUU | 68 |
| H53_96-120 | GCUCAGCUUCUUCCUUAGCUUCCAG | 69 |
| H53_101-125 | GACCUGCUCAGCUUCUUCCUUAGCU | 70 |
| H53_106-130 | CCUAAGACCUGCUCAGCUUCUUCCU | 71 |
| H53_111-135 | CCUGUCCUAAGACCUGCUCAGCUUC | 72 |
| H53_116-140 | UCUGGCCUGUCCUAAGACCUGCUCA | 73 |
| H53_121-145 | UUGGCUCUGGCCUGUCCUAAGACCU | 74 |
| H53_126-150 | CAAGCUUGGCUCUGGCCUGUCCUAA | 75 |
| H53_131-155 | UGACUCAAGCUUGGCUCUGGCCUGU | 76 |
| H53_136-160 | UUCCAUGACUCAAGCUUGGCUCUGG | 77 |
| H53_141-165 | CCUCCUUCCAUGACUCAAGCUUGGC | 78 |
| H53_146-170 | GGGACCCUCCUUCCAUGACUCAAGC | 79 |
| H53_151-175 | GUAUAGGGACCCUCCUUCCAUGACU | 80 |

TABLE 7-continued

| Antisense oligomer | Nucleotide sequence | SEQ ID NO: |
|---|---|---|
| H53_156-180 | CUACUGUAUAGGGACCCUCCUUCCA | 81 |
| H53_161-185 | UGCAUCUACUGUAUAGGGACCCUCC | 82 |
| H53_166-190 | UGGAUUGCAUCUACUGUAUAGGGAC | 83 |
| H53_171-195 | UCUUUUGGAUUGCAUCUACUGUAUA | 84 |
| H53_176-200 | GAUUUCUUUUGGAUUGCAUCUACU | 85 |
| H53_181-205 | UCUGUGAUUUCUUUUGGAUUGCAU | 86 |
| H53_186-210 | UGGUUUCUGUGAUUUCUUUUGGAU | 87 |
| H53_84-108 | CCUUAGCUUCCAGCCAUUGUGUUGA | 88 |
| H53_88-112 | UCUUCCUUAGCUUCCAGCCAUUGUG | 89 |
| H53_119-143 | GGCUCUGGCCUGUCCUAAGACCUGC | 90 |
| H53_124-148 | AGCUUGGCUCUGGCCUGUCCUAAGA | 91 |
| H53_128-152 | CUCAAGCUUGGCUCUGGCCUGUCCU | 92 |
| H53_144-168 | GACCCUCCUUCCAUGACUCAAGCUU | 93 |
| H53_149-173 | AUAGGGACCCUCCUUCCAUGACUCA | 94 |
| H53_153-177 | CUGUAUAGGGACCCUCCUUCCAUGA | 95 |
| H53_179-203 | UGUGAUUUCUUUUGGAUUGCAUCU | 96 |
| H53_184-208 | GUUUCUGUGAUUUCUUUUGGAUUG | 97 |
| H53_188-212 | CUUGGUUUCUGUGAUUUCUUUUGG | 98 |
| H53_29-53 | CCGGUUCUGAAGGUGUUCUUGUACU | 99 |
| H53_30-54 | UCCGGUUCUGAAGGUGUUCUUGUAC | 100 |
| H53_32-56 | CCUCCGGUUCUGAAGGUGUUCUUGU | 101 |
| H53_33-57 | GCCUCCGGUUCUGAAGGUGUUCUUG | 102 |
| H53_34-58 | UGCCUCCGGUUCUGAAGGUGUUCUU | 103 |
| H53_35-59 | UUGCCUCCGGUUCUGAAGGUGUUCU | 104 |
| H53_37-61 | UGUUGCCUCCGGUUCUGAAGGUGUU | 105 |
| H53_38-62 | CUGUUGCCUCCGGUUCUGAAGGUGU | 106 |
| H53_39-63 | ACUGUUGCCUCCGGUUCUGAAGGUG | 107 |
| H53_40-64 | AACUGUUGCCUCCGGUUCUGAAGGU | 108 |
| H53_32-61 | UGUUGCCUCCGGUUCUGAAGGUGUUCUUGU | 109 |
| H53_32-51 | GGUUCUGAAGGUGUUCUUGU | 110 |
| H53_35-54 | UCCGGUUCUGAAGGUGUUCU | 111 |
| H53_37-56 | CCUCCGGUUCUGAAGGUGUU | 112 |
| H53_40-59 | UUGCCUCCGGUUCUGAAGGU | 113 |
| H53_42-61 | UGUUGCCUCCGGUUCUGAAG | 114 |
| H53_32-49 | UUCUGAAGGUGUUCUUGU | 115 |
| H53_35-52 | CGGUUCUGAAGGUGUUCU | 116 |
| H53_38-55 | CUCCGGUUCUGAAGGUGU | 117 |

TABLE 7-continued

| Antisense oligomer | Nucleotide sequence | SEQ ID NO: |
|---|---|---|
| H53_41-58 | UGCCUCCGGUUCUGAAGG | 118 |
| H53_44-61 | UGUUGCCUCCGGUUCUGA | 119 |
| H53_35-49 | UUCUGAAGGUGUUCU | 120 |
| H53_40-54 | UCCGGUUCUGAAGGU | 121 |
| H53_45-59 | UUGCCUCCGGUUCUG | 122 |
| H53_45-62 | CUGUUGCCUCCGGUUCUG | 123 |

RD cells (human rhabdomyosarcoma cell line) were plated at 3×10$^5$ in a 6-well plate and cultured in 2 mL of Eagle's minimal essential medium (EMEM) (manufactured by Sigma, Inc., hereinafter the same) containing 10% fetal calf serum (FCS) (manufactured by Invitrogen Corp.) under conditions of 37° C. and 5% $CO_2$ overnight. Complexes of various antisense oligomers (Japan Bio Services) (1 µM) for exon 53 skipping and Lipofectamine 2000 (manufactured by Invitrogen Corp.) were prepared and 200 µl was added to RD cells where 1.8 mL of the medium was exchanged, to reach the final concentration of 100 nM.

After completion of the addition, the cells were cultured overnight. The cells were washed twice with PBS (manufactured by Nissui, hereafter the same) and then 500 µl of ISOGEN (manufactured by Nippon Gene) were added to the cells. After the cells were allowed to stand at room temperature for a few minutes for cell lysis, the lysate was collected in an Eppendorf tube. The total RNA was extracted according to the protocol attached to ISOGEN. The concentration of the total RNA extracted was determined using a NanoDrop ND-1000 (manufactured by LMS).

One-Step RT-PCR was performed with 400 ng of the extracted total RNA using a Titan One Tube RT-PCR Kit (manufactured by Roche). A reaction solution was prepared in accordance with the protocol attached to the kit. A PTC-100 (manufactured by MJ Research) was used as a thermal cycler. The RT-PCR program used is as follows.

50° C., 30 mins: reverse transcription
94° C., 2 mins: thermal denaturation
[94° C., 10 seconds; 58° C., 30 seconds; 68° C., 45 seconds]×30 cycles: PCR amplification
68° C., 7 mins: final extension The nucleotide sequences of the forward primer and reverse primer used for RT-PCR are given below.

```
Forward primer:
                                    (SEQ ID NO: 42)
5'-CATCAAGCAGAAGGCAACAA-3'

Reverse primer:
                                    (SEQ ID NO: 43)
5'-GAAGTTTCAGGGCCAAGTCA-3'
```

Subsequently, a nested PCR was performed with the amplified product of RT-PCR above using a Taq DNA Polymerase (manufactured by Roche). The PCR program used is as follows.

94° C., 2 mins: thermal denaturation
[94° C., 15 seconds; 58° C., 30 seconds; 68° C., 45 seconds]×30 cycles: PCR amplification
68° C., 7 mins: final extension The nucleotide sequences of the forward primer and reverse primer used for the nested PCR above are given below.

```
Forward primer:
                                    (SEQ ID NO: 40)
5'-AGGATTTGGAACAGAGGCGTC-3'

Reverse primer:
                                    (SEQ ID NO: 41)
5'-GTCTGCCACTGGCGGAGGTC-3'
```

The reaction product, 1 µl, of the nested PCR above was analyzed using a Bioanalyzer (manufactured by Agilent Technologies, Inc.).

The polynucleotide level "A" of the band with exon 53 skipping and the polynucleotide level "B" of the band without exon 53 skipping were measured. Based on these measurement values of "A" and "B," the skipping efficiency was determined by the following equation:

Skipping efficiency(%)=$A/(A+B)\times100$

Experimental Results

The results are shown in FIGS. 9 to 17. These experiments revealed that, when the antisense oligomers were designed at exons 31-61 from the 5' end of exon 53 in the human dystrophin gene, exon 53 skipping could be caused with a high efficiency.

Test Example 7

Using an Amaxa Cell Line Nucleofector Kit L on Nucleofector II (Lonza), 0.3 to 30 µM of the antisense oligomers were transfected with 3.5×10$^5$ of RD cells (human rhabdomyosarcoma cell line). The Program T-030 was used.

After the transfection, the cells were cultured overnight in 2 mL of Eagle's minimal essential medium (EMEM) (manufactured by Sigma, Inc., hereinafter the same) containing 10% fetal calf serum (FCS) (manufactured by Invitrogen Corp.) under conditions of 37° C. and 5% $CO_2$. The cells were washed twice with PBS (manufactured by Nissui, hereinafter the same) and 500 µl of ISOGEN (manufactured by Nippon Gene) was then added to the cells. After the cells were allowed to stand at room temperature for a few minutes to lyse the cells, the lysate was collected in an Eppendorf tube. The total RNA was extracted according to the protocol attached to ISOGEN. The concentration of the total RNA extracted was determined using a NanoDrop ND-1000 (manufactured by LMS).

One-Step RT-PCR was performed with 400 ng of the extracted total RNA using a QIAGEN OneStep RT-PCR Kit (manufactured by Qiagen, Inc.). A reaction solution was prepared in accordance with the protocol attached to the kit. The thermal cycler used was a PTC-100 (manufactured by MJ Research). The RT-PCR program used is as follows.

50° C., 30 mins: reverse transcription
95° C., 15 mins: thermal denaturation
[94° C., 30 seconds; 60° C., 30 seconds; 72° C., 1 mins]×35 cycles: PCR amplification
72° C., 10 mins: final extension The nucleotide sequences of the forward primer and reverse primer used for RT-PCR are given below.

```
Forward primer:
                                    (SEQ ID NO: 42)
5'-CATCAAGCAGAAGGCAACAA-3'
```

-continued

Reverse primer:
(SEQ ID NO: 43)
5'-GAAGTTTCAGGGCCAAGTCA-3'

The reaction product, 1 μl, of the PCR above was analyzed using a Bioanalyzer (manufactured by Agilent Technologies, Inc.).

The polynucleotide level "A" of the band with exon 53 skipping and the polynucleotide level "B" of the band without exon 53 skipping were measured. Based on these measurement values of "A" and "B," the skipping efficiency was determined by the following equation:

Skipping efficiency(%)=$A/(A+B)\times 100$

Experimental Results

Figure 18:
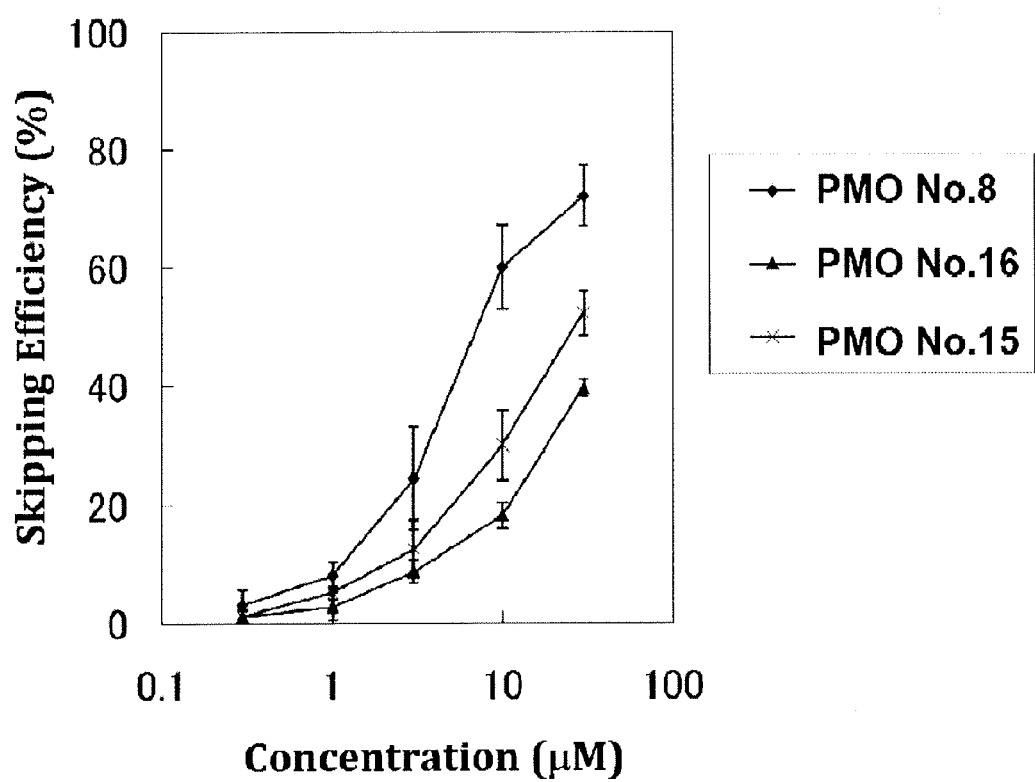
FIG. 18 shows the efficiency of exon 53 skipping in the human dystrophin gene in human rhabdomyosarcoma cells (RD cells) at the respective concentrations of the oligomers.
Figure 19:
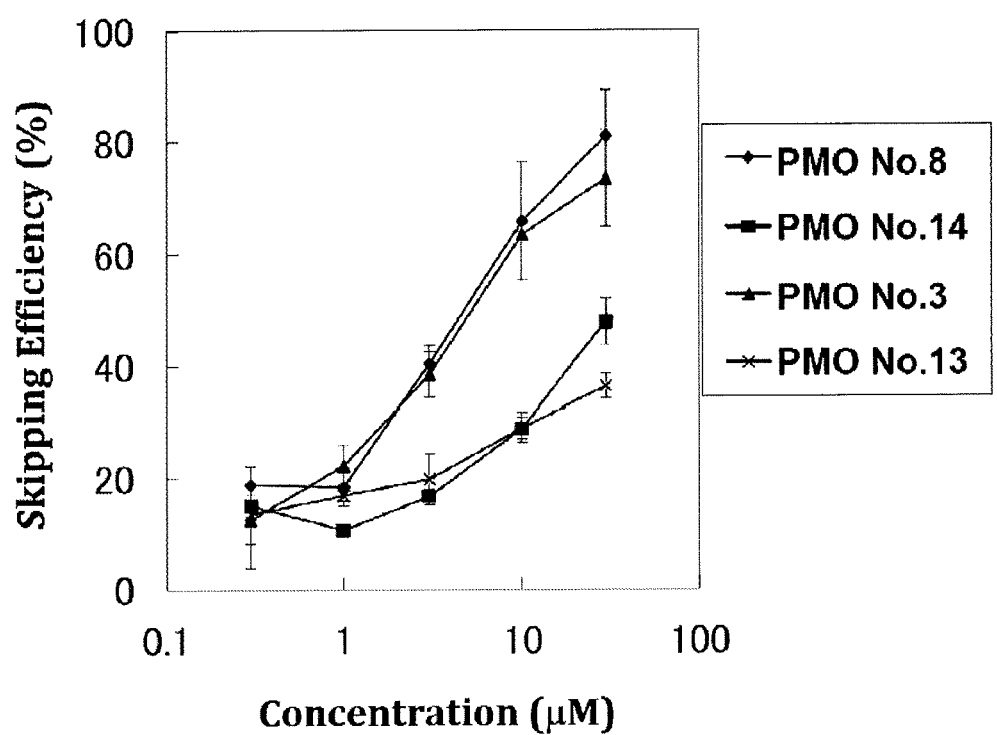
FIG. 19 shows the efficiency of exon 53 skipping in the human dystrophin gene in human rhabdomyosarcoma cells (RD cells) at the respective concentrations of the oligomers.

The results are shown in FIGS. 18 and 19. These experiments revealed that the oligomer PMO No. 8 of the present invention caused exon 53 skipping with a markedly high efficiency as compared to the antisense oligomers PMO Nos. 15 and 16 (FIG. 18). It was also revealed that the oligomers PMO Nos. 3 and 8 of the present invention caused exon 53 skipping with a markedly high efficiency as compared to the oligomers PMO Nos. 13 and 14 of the present invention (FIG. 19). These results showed that the sequences with —OH group at the 5' end provide a higher skipping efficiency even in the same sequences.

INDUSTRIAL APPLICABILITY

Experimental results in TEST EXAMPLES demonstrate that the oligomers of the present invention (PMO Nos. 1 to 10) all caused exon 53 skipping with a markedly high efficiency under all cell environments, as compared to the oligomers (PMO Nos. 11, 12, 15 and 16) in accordance with the prior art. The 5017 cells used in TEST EXAMPLE 2 are the cells isolated from DMD patients, and the fibroblasts used in TEST EXAMPLES 3 and 5 are exon 53 skipping target cells from DMD patients. Particularly in TEST EXAMPLES 3 and 5, the oligomers of the present invention show the exon 53 skipping efficiency of 90% or higher in the cells from DMD patients that are the target for exon 53 skipping. Consequently, the oligomers of the present invention can induce exon 53 skipping with a high efficiency, when DMD patients are administered.

Therefore, the oligomers of the present invention are extremely useful for the treatment of DMD.

Sequence Listing Free Text

SEQ ID NO: 2: synthetic nucleic acid
SEQ ID NO: 3: synthetic nucleic acid
SEQ ID NO: 4: synthetic nucleic acid
SEQ ID NO: 5: synthetic nucleic acid
SEQ ID NO: 6: synthetic nucleic acid
SEQ ID NO: 7: synthetic nucleic acid
SEQ ID NO: 8: synthetic nucleic acid
SEQ ID NO: 9: synthetic nucleic acid
SEQ ID NO: 10: synthetic nucleic acid
SEQ ID NO: 11: synthetic nucleic acid
SEQ ID NO: 12: synthetic nucleic acid
SEQ ID NO: 13: synthetic nucleic acid
SEQ ID NO: 14: synthetic nucleic acid
SEQ ID NO: 15: synthetic nucleic acid
SEQ ID NO: 16: synthetic nucleic acid
SEQ ID NO: 17: synthetic nucleic acid
SEQ ID NO: 18: synthetic nucleic acid
SEQ ID NO: 19: synthetic nucleic acid
SEQ ID NO: 20: synthetic nucleic acid
SEQ ID NO: 21: synthetic nucleic acid
SEQ ID NO: 22: synthetic nucleic acid
SEQ ID NO: 23: synthetic nucleic acid
SEQ ID NO: 24: synthetic nucleic acid
SEQ ID NO: 25: synthetic nucleic acid
SEQ ID NO: 26: synthetic nucleic acid
SEQ ID NO: 27: synthetic nucleic acid
SEQ ID NO: 28: synthetic nucleic acid
SEQ ID NO: 29: synthetic nucleic acid
SEQ ID NO: 30: synthetic nucleic acid
SEQ ID NO: 31: synthetic nucleic acid
SEQ ID NO: 32: synthetic nucleic acid
SEQ ID NO: 33: synthetic nucleic acid
SEQ ID NO: 34: synthetic nucleic acid
SEQ ID NO: 35: synthetic nucleic acid
SEQ ID NO: 36: synthetic nucleic acid
SEQ ID NO: 37: synthetic nucleic acid
SEQ ID NO: 38: synthetic nucleic acid
SEQ ID NO: 39: synthetic nucleic acid
SEQ ID NO: 40: synthetic nucleic acid
SEQ ID NO: 41: synthetic nucleic acid
SEQ ID NO: 42: synthetic nucleic acid
SEQ ID NO: 43: synthetic nucleic acid
SEQ ID NO: 45: synthetic nucleic acid
SEQ ID NO: 46: synthetic nucleic acid
SEQ ID NO: 47: synthetic nucleic acid
SEQ ID NO: 48: synthetic nucleic acid
SEQ ID NO: 49: synthetic nucleic acid
SEQ ID NO: 50: synthetic nucleic acid
SEQ ID NO: 51: synthetic nucleic acid
SEQ ID NO: 52: synthetic nucleic acid
SEQ ID NO: 53: synthetic nucleic acid
SEQ ID NO: 54: synthetic nucleic acid
SEQ ID NO: 55: synthetic nucleic acid
SEQ ID NO: 56: synthetic nucleic acid
SEQ ID NO: 57: synthetic nucleic acid
SEQ ID NO: 58: synthetic nucleic acid
SEQ ID NO: 59: synthetic nucleic acid
SEQ ID NO: 60: synthetic nucleic acid
SEQ ID NO: 61: synthetic nucleic acid
SEQ ID NO: 62: synthetic nucleic acid
SEQ ID NO: 63: synthetic nucleic acid
SEQ ID NO: 64: synthetic nucleic acid
SEQ ID NO: 65: synthetic nucleic acid
SEQ ID NO: 66: synthetic nucleic acid
SEQ ID NO: 67: synthetic nucleic acid
SEQ ID NO: 68: synthetic nucleic acid
SEQ ID NO: 69: synthetic nucleic acid
SEQ ID NO: 70: synthetic nucleic acid
SEQ ID NO: 71: synthetic nucleic acid
SEQ ID NO: 72: synthetic nucleic acid
SEQ ID NO: 73: synthetic nucleic acid
SEQ ID NO: 74: synthetic nucleic acid
SEQ ID NO: 75: synthetic nucleic acid
SEQ ID NO: 76: synthetic nucleic acid
SEQ ID NO: 77: synthetic nucleic acid
SEQ ID NO: 78: synthetic nucleic acid
SEQ ID NO: 79: synthetic nucleic acid
SEQ ID NO: 80: synthetic nucleic acid
SEQ ID NO: 81: synthetic nucleic acid
SEQ ID NO: 82: synthetic nucleic acid
SEQ ID NO: 83: synthetic nucleic acid
SEQ ID NO: 84: synthetic nucleic acid
SEQ ID NO: 85: synthetic nucleic acid
SEQ ID NO: 86: synthetic nucleic acid
SEQ ID NO: 87: synthetic nucleic acid
SEQ ID NO: 88: synthetic nucleic acid
SEQ ID NO: 89: synthetic nucleic acid SEQ ID NO: 90: synthetic nucleic acid
SEQ ID NO: 91: synthetic nucleic acid
SEQ ID NO: 92: synthetic nucleic acid
SEQ ID NO: 93: synthetic nucleic acid
SEQ ID NO: 94: synthetic nucleic acid
SEQ ID NO: 95: synthetic nucleic acid
SEQ ID NO: 96: synthetic nucleic acid
SEQ ID NO: 97: synthetic nucleic acid
SEQ ID NO: 98: synthetic nucleic acid
SEQ ID NO: 99: synthetic nucleic acid
SEQ ID NO: 100: synthetic nucleic acid
SEQ ID NO: 101: synthetic nucleic acid
SEQ ID NO: 102: synthetic nucleic acid
SEQ ID NO: 103: synthetic nucleic acid
SEQ ID NO: 104: synthetic nucleic acid
SEQ ID NO: 105: synthetic nucleic acid
SEQ ID NO: 106: synthetic nucleic acid
SEQ ID NO: 107: synthetic nucleic acid
SEQ ID NO: 108: synthetic nucleic acid
SEQ ID NO: 109: synthetic nucleic acid
SEQ ID NO: 110: synthetic nucleic acid
SEQ ID NO: 111: synthetic nucleic acid
SEQ ID NO: 112: synthetic nucleic acid
SEQ ID NO: 113: synthetic nucleic acid
SEQ ID NO: 114: synthetic nucleic acid
SEQ ID NO: 115: synthetic nucleic acid
SEQ ID NO: 116: synthetic nucleic acid
SEQ ID NO: 117: synthetic nucleic acid
SEQ ID NO: 118: synthetic nucleic acid
SEQ ID NO: 119: synthetic nucleic acid
SEQ ID NO: 120: synthetic nucleic acid
SEQ ID NO: 121: synthetic nucleic acid
SEQ ID NO: 122: synthetic nucleic acid
SEQ ID NO: 123: synthetic nucleic acid

The invention claimed is:

1. A method of treating Duchenne muscular dystrophy (DMD) in a patient in need thereof comprising administering an antisense oligomer, or a pharmaceutically acceptable salt or hydrate thereof, wherein the antisense oligomer consists of a nucleotide sequence complementary to the sequence consisting of the 36th to the 56th nucleotides from the 5' end of the 53rd exon in a human dystrophin pre-mRNA, and wherein the 53rd exon in the human dystrophin pre-mRNA consists of a nucleotide sequence corresponding to SEQ ID NO: 1.

2. A method of treating Duchenne muscular dystrophy (DMD) in a patient in need thereof comprising administering a pharmaceutical composition comprising as an active ingredient an antisense oligomer, or a pharmaceutically acceptable salt or hydrate thereof, wherein the antisense oligomer consists of a nucleotide sequence complementary to the sequence consisting of the 36th to the 56th nucleotides from the 5' end of the 53rd exon in a human dystrophin pre-mRNA, and wherein the 53rd exon in the human dystrophin pre-mRNA consists of a nucleotide sequence corresponding to SEQ ID NO: 1.

3. The method according to claim 1, wherein the antisense oligomer is an oligonucleotide.

4. The method according to claim 3, wherein the oligonucleotide comprises at least one nucleotide having a modified sugar moiety or having a modified phosphate-binding region.

5. The method according to claim 4, wherein the modified sugar moiety is a ribose in which the 2'-OH group is replaced by any one selected from the group consisting of: OR, R, R'OR, SH, SR, $NH_2$, NHR, $NR_2$, $N_3$, CN, F, Cl, Br, and I (wherein R is an alkyl or an aryl and R' is an alkylene).

6. The method according to claim 4, wherein the modified phosphate-binding region is any one selected from the group consisting of: a phosphorothioate bond, a phosphorodithioate bond, an alkylphosphonate bond, a phosphoramidate bond, and a boranophosphate bond.

7. The method according to claim 1, wherein the antisense oligomer is a morpholino oligomer.

8. The method according to claim 7, wherein the antisense oligomer is a phosphorodiamidate morpholino oligomer.

9. The method according to claim 8, wherein the 5' end of the antisense oligomer is any one of the groups of chemical formulae (1) to (3) below:

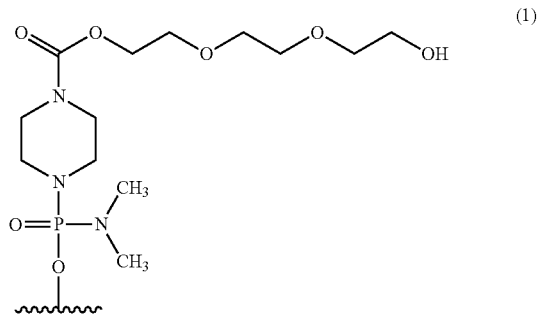

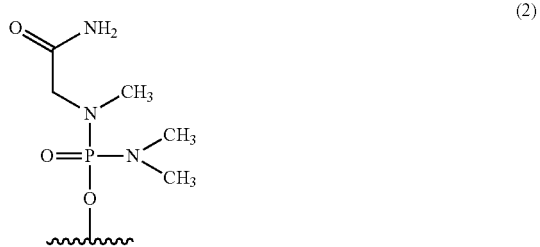

(3) 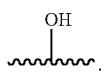

10. The method according to claim 1, wherein the antisense oligomer, or the pharmaceutically acceptable salt or hydrate thereof, is administered intravenously.

11. The method according to claim 2, wherein the antisense oligomer is an oligonucleotide.

12. The method according to claim 11, wherein the oligonucleotide comprises at least one nucleotide having a modified sugar moiety or having a modified phosphate-binding region.

13. The method according to claim 12, wherein the modified sugar moiety is a ribose in which the 2'-OH group is replaced by any one selected from the group consisting of: OR, R, R'OR, SH, SR, $NH_2$, NHR, $NR_2$, $N_3$, CN, F, Cl, Br, and I (wherein R is an alkyl or an aryl and R' is an alkylene).

14. The method according to claim 12, wherein the modified phosphate-binding region is any one selected from the group consisting of: a phosphorothioate bond, a phosphorodithioate bond, an alkylphosphonate bond, a phosphoramidate bond, and a boranophosphate bond.

15. The method according to claim 2, wherein the antisense oligomer is a morpholino oligomer.

16. The method according to claim 15, wherein the antisense oligomer is a phosphorodiamidate morpholino oligomer.

17. The method according to claim 16, wherein the 5' end of the antisense oligomer is any one of the groups of chemical formulae (1) to (3) below:

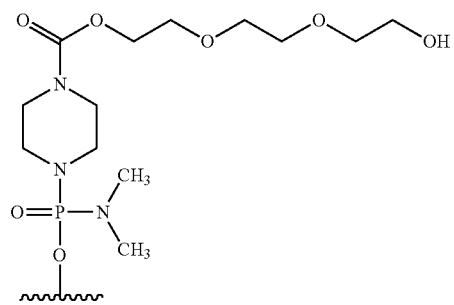

(1)

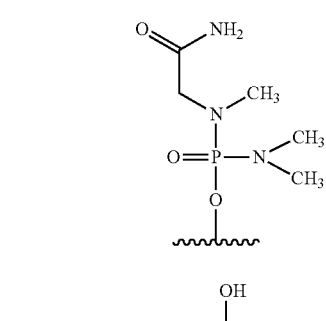

(2)

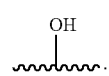

(3)

18. The method according to claim 2, wherein the pharmaceutical composition is administered intravenously.

\* \* \* \* \*